United States Patent
Liu et al.

(10) Patent No.: US 12,319,689 B2
(45) Date of Patent: Jun. 3, 2025

(54) METHYL- AND TRIFLUOROMETHYL-CONTAINING DISUBSTITUTED SULFONAMIDE SELECTIVE BCL-2 INHIBITOR

(71) Applicant: CHIA TAI TIANQING PHARMACEUTICAL GROUP CO., LTD., Lianyungang (CN)

(72) Inventors: Fei Liu, Lianyungang (CN); Yanlong Liu, Lianyungang (CN); Hongjiang Xu, Lianyungang (CN); Xiquan Zhang, Lianyungang (CN); Shanchun Wang, Lianyungang (CN); Jianqing Zhang, Lianyungang (CN); Weiwei Feng, Lianyungang (CN); Bin Wang, Lianyungang (CN); Jinan Wang, Lianyungang (CN); Yubing Wang, Lianyungang (CN); Xujing Tang, Lianyungang (CN); Quandeng Nie, Lianyungang (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 786 days.

(21) Appl. No.: 17/613,910

(22) PCT Filed: May 22, 2020

(86) PCT No.: PCT/CN2020/091741
§ 371 (c)(1),
(2) Date: Nov. 23, 2021

(87) PCT Pub. No.: WO2020/238785
PCT Pub. Date: Dec. 3, 2020

(65) Prior Publication Data
US 2022/0220110 A1    Jul. 14, 2022

(30) Foreign Application Priority Data
May 24, 2019 (CN) .......... 201910439955.X
Sep. 29, 2019 (CN) .......... 201910933552.0

(51) Int. Cl.
*C07D 471/04* (2006.01)
(52) U.S. Cl.
CPC ................. *C07D 471/04* (2013.01)
(58) Field of Classification Search
None
See application file for complete search history.

(56) References Cited

FOREIGN PATENT DOCUMENTS

| | | |
|---|---|---|
| CN | 102307872 A | 1/2012 |
| CN | 103167867 A | 6/2013 |
| CN | 104876927 A | 9/2015 |
| WO | 2010065824 A2 | 6/2010 |
| WO | 2010065865 | 6/2010 |
| WO | 2010138588 | 12/2010 |
| WO | 2012058392 A1 | 5/2012 |
| WO | 2012071374 | 5/2012 |
| WO | 2019185025 A1 | 10/2019 |
| WO | 2020088442 A1 | 5/2020 |

OTHER PUBLICATIONS

Chinese Office Action dated Jul. 7, 2021 as received in application No. 201980021318.9.
Chinese Office Action dated Dec. 5, 2022 as received in application No. 202080034896.9.

*Primary Examiner* — Samantha L Shterengarts
(74) *Attorney, Agent, or Firm* — Maschoff Brennan

(57) ABSTRACT

Disclosed is a methyl- and trifluoromethyl-containing disubstituted sulfonamide selective BCL-2 inhibitor; specifically disclosed are a compound of formula I, a stereoisomer or pharmaceutically acceptable salt of same, a preparation method therefor, and a pharmaceutical composition comprising the compound. Also disclosed are uses of the compound and of the pharmaceutical composition comprising the compound in treating anti-apoptotic protein BCL-2-related diseases such as cancer.

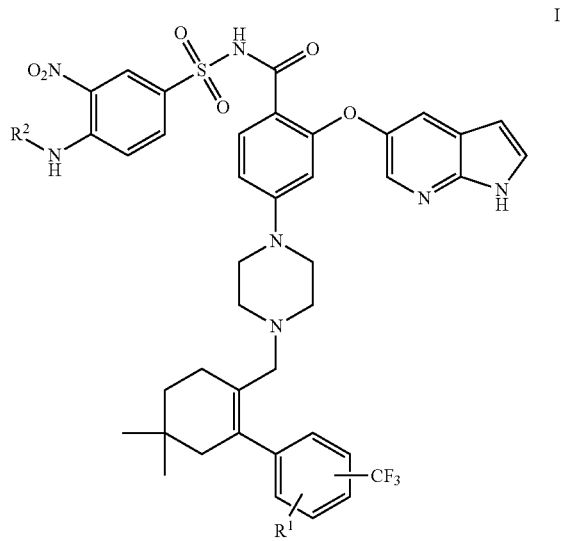

20 Claims, No Drawings

METHYL- AND TRIFLUOROMETHYL-CONTAINING DISUBSTITUTED SULFONAMIDE SELECTIVE BCL-2 INHIBITOR

CROSS-REFERENCE TO RELATED APPLICATIONS

The present application claims benefit and priority to the Chinese Patent No. 201910439955.X filed with the National Intellectual Property Administration, PRC on May 24, 2019 and the Chinese Patent No. 201910933552.0 filed with the National Intellectual Property Administration, PRC on Sep. 29, 2019, the content of each of which is incorporated herein by reference in its entirety.

TECHNICAL FIELD

The present application relates to compounds that selectively inhibit anti-apoptotic protein BCL-2, a method for preparing the same, a pharmaceutical composition containing the same and use of the same in treating an anti-apoptotic protein BCL-2-related disease, e.g., cancer.

BACKGROUND

BCL-2 proteins are classified into three families: BCL-2 family (including members such as BCL-2 and BCL-XL), BAX family and BH3-only family. Among them, the BCL-2 family plays an anti-apoptotic role, while members of the other two families play a pro-apoptotic role.

Anti-apoptotic proteins of the BCL-2 family are associated with many diseases and are being investigated as potential targets of therapeutic drugs. Such targets for interventional therapy include, for example, proteins BCL-2 and BCL-XL of the BCL-2 family, etc. Recently, inhibitors for proteins of BCL-2 family have been reported in WO2012071374, WO2010138588 and WO2010065865. Although inhibitors that bind to a target protein with high affinity are introduced therein, binding affinity of compounds is only one of many parameters to be considered. One objective is to produce a compound that preferentially binds to, i.e., has selectivity for, one protein over another. The manifestation of this selectivity, as is well known, is high binding affinity for a specific protein and lower binding affinity for another.

Disclosed BCL-2 inhibitors are less selective for anti-apoptotic BCL-XL and BCL-2 proteins, and thus have a greater probability of causing side effects. They are characterized by inhibiting anti-apoptotic BCL-XL protein and causing side effects such as thrombocytopenia.

The present application includes a series of compounds that exhibit higher selectivity for anti-apoptotic BCL-2 and BCL-XL proteins, and also have better performance in inhibiting the activity of anti-apoptotic BCL-2 protein. Meanwhile, these compounds have better stability of liver microsomes and optimized pharmacokinetic parameters, showing more promising druggability.

DETAILED DESCRIPTION

In one aspect, the present application relates to a compound of formula I, a stereoisomer thereof or a pharmaceutically acceptable salt thereof,

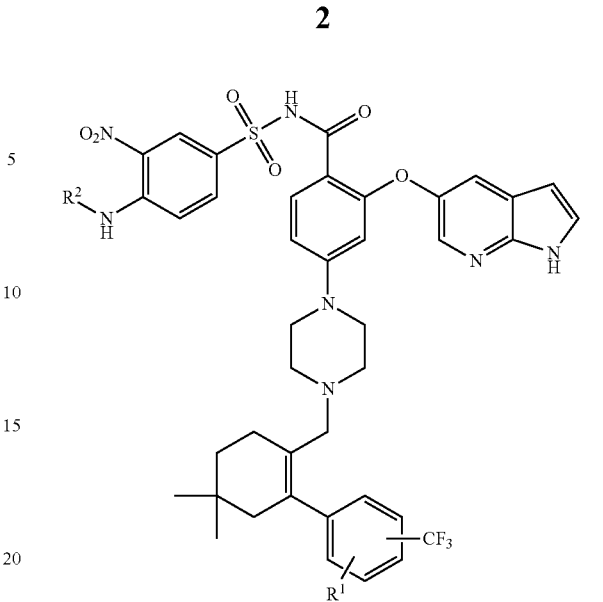

wherein, $R^1$ is selected from $C_{1-6}$ alkyl;

$R^2$ is selected from the group consisting of $R^3$ and $-C_{1-6}$ alkylene-$R^3$;

$R^3$ is selected from 5-6 membered heterocycloalkyl, wherein the 5-6 membered heterocycloalkyl is optionally substituted with one or two groups selected from the group consisting of 3-6 membered heterocycloalkyl, $C_{3-6}$ cycloalkyl, $-COR^a$, $-SO_2R^b$, and $C_{1-6}$ alkyl optionally substituted with halogen;

$R^a$ or $R^b$ is each independently selected from the group consisting of H, 3-6 membered heterocycloalkyl, $C_{3-6}$ cycloalkyl and $C_{1-6}$ alkyl, wherein the $C_{1-6}$ alkyl is optionally substituted with halogen, $-CN$, $-N(C_{1-6}$ alkyl)$_2$, $-NHC_{1-6}$ alkyl or $-OC_{1-6}$ alkyl.

In some embodiments, the structural fragment

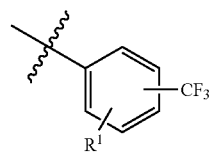

is selected from

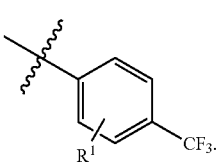

In some embodiments, the structural fragment

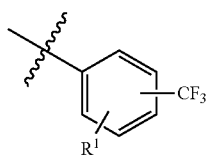

is selected from the group consisting of

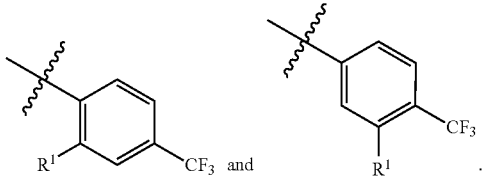

In some embodiments, the structural fragment

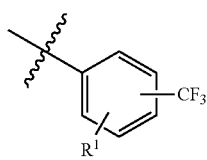

is selected from

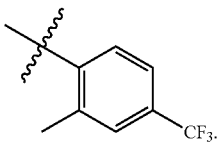 [SMILES: *c1ccc(C(F)(F)F)cc1C]

In some embodiments, the structural fragment

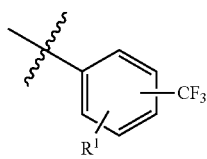

is selected from

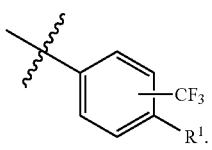

In some embodiments, the structural fragment

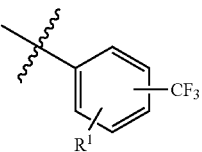

is selected from the group consisting of

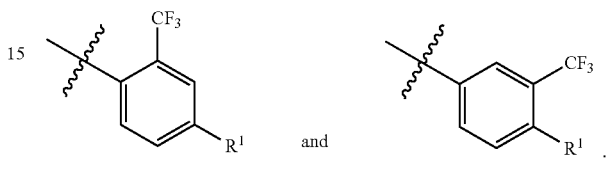

In some embodiments, $R^1$ is selected from $C_{1-4}$ alkyl. In some embodiments, $R^1$ is selected from the group consisting of methyl, ethyl, n-propyl, isopropyl and tert-butyl. In some embodiments, $R^1$ is selected from the group consisting of methyl and ethyl. In some embodiments, $R^1$ is selected from methyl.

In some embodiments, $R^2$ is selected from the group consisting of $R^3$ and $-(CH_2)_n-R^3$, wherein n is selected from the group consisting of 1, 2, 3 and 4; or n is selected from the group consisting of 1, 2 and 3; or n is selected from the group consisting of 1 and 2.

In some embodiments, $R^2$ is selected from $-(CH_2)_n-R^3$, and n is selected from the group consisting of 1 and 2. In some embodiments, $R^2$ is selected from $-CH_2R^3$.

In some embodiments, $R^3$ is selected from 5-6 membered heterocycloalkyl, wherein the 5-6 membered heterocycloalkyl is optionally substituted with one or two groups.

In some embodiments, the heteroatom in the 5-6 membered heterocycloalkyl is selected from the group consisting of oxygen and nitrogen, wherein the number of the heteroatom is preferably 1 or 2.

In some embodiments, the heteroatom in the 5-6 membered heterocycloalkyl is selected from oxygen, wherein the number of the heteroatom is preferably 1 or 2.

In some embodiments, the heteroatom in the 5-6 membered heterocycloalkyl is selected from nitrogen, wherein the number of the heteroatom is preferably 1 or 2.

In some embodiments, $R^3$ is selected from 5-6 membered heterocycloalkyl, wherein the 5-6 membered heterocycloalkyl is optionally substituted with one or two groups at the ring N atom.

In some embodiments, $R^3$ is selected from 5-6 membered heterocycloalkyl, wherein the 5-6 membered heterocycloalkyl is optionally substituted with one or two groups selected from the group consisting of 3-6 membered heterocycloalkyl, $-COR^a$, $-SO_2R^b$, and $C_{1-6}$ alkyl optionally substituted with halogen.

In some embodiments, $R^3$ is selected from 5-6 membered heterocycloalkyl, wherein the 5-6 membered heterocycloalkyl is optionally substituted with one or two groups selected from the group consisting of $-COR^a$, $-SO_2R^b$, and $C_{1-6}$ alkyl optionally substituted with halogen.

In some embodiments, $R^3$ is selected from 5-6 membered heterocycloalkyl, wherein the 5-6 membered heterocycloalkyl is optionally substituted with 3-6 membered heterocycloalkyl.

In some embodiments, $R^3$ is selected from 5-6 membered heterocycloalkyl, wherein the 5-6 membered heterocycloalkyl is optionally substituted with $-COR^a$.

In some embodiments, R³ is selected from 5-6 membered heterocycloalkyl, wherein the 5-6 membered heterocycloalkyl is optionally substituted with —SO₂R$^b$.

In some embodiments, R³ is selected from 5-6 membered heterocycloalkyl, wherein the 5-6 membered heterocycloalkyl is optionally substituted with $C_{1-6}$ alkyl, wherein the $C_{1-4}$ alkyl is optionally substituted with halogen. In some embodiments, the $C_{1-6}$ alkyl is optionally substituted with fluorine. In some embodiments, R³ is selected from 5-6 membered heterocycloalkyl, wherein the 5-6 membered heterocycloalkyl is optionally substituted with $C_{1-3}$ alkyl, wherein the $C_{1-3}$ alkyl is optionally substituted with fluorine. In some embodiments, the 5-6 membered heterocycloalkyl is optionally substituted with methyl, ethyl, methyl substituted with fluorine, or ethyl substituted with fluorine. In some embodiments, the 5-6 membered heterocycloalkyl is optionally substituted with methyl, ethyl, trifluoromethyl, or ethyl substituted with 1 or 5 fluorine.

In some embodiments, R$^a$ or R$^b$ is each independently selected from the group consisting of H, 3-6 membered heterocycloalkyl, $C_{3-6}$ cycloalkyl and $C_{1-4}$ alkyl, wherein the $C_{1-4}$ alkyl is optionally substituted with halogen, —CN, —N($C_{1-4}$ alkyl)₂, —NHC$_{1-4}$ alkyl or —OC$_{1-4}$ alkyl. In some embodiments, R$^a$ is selected from the group consisting of H, 3-6 membered heterocycloalkyl, $C_{3-6}$ cycloalkyl and $C_{1-4}$ alkyl, wherein the $C_{1-4}$ alkyl is optionally substituted with halogen, —CN, —N($C_{1-4}$ alkyl)₂ or —OC$_{1-4}$ alkyl. In some embodiments, R$^b$ is selected from the group consisting of 3-6 membered heterocycloalkyl, $C_{3-6}$ cycloalkyl and $C_{1-4}$ alkyl, wherein the $C_{1-4}$ alkyl is optionally substituted with halogen.

In some embodiments, R$^a$ or R$^b$ is each independently selected from the group consisting of H, methyl, ethyl, isopropyl, tert-butyl, cyclopropyl, cyclobutyl and monooxacyclobutyl, wherein the methyl or ethyl is optionally substituted with fluorine, —CN, —OCH₃ or —N(CH₃)₂. In some embodiments, R$^a$ is selected from the group consisting of H, methyl, isopropyl, tert-butyl, cyclopropyl and monooxacyclobutyl, wherein the methyl is optionally substituted with fluorine, —CN, —OCH₃ or —N(CH₃)₂. In some embodiments, R$^b$ is selected from the group consisting of methyl, ethyl, cyclopropyl, cyclobutyl and monooxacyclobutyl, wherein the methyl or ethyl is optionally substituted with fluorine.

In some embodiments, R$^a$ or R$^b$ is each independently selected from the group consisting of H, methyl, ethyl, isopropyl, tert-butyl, trifluoromethyl, pentafluoroethyl, —CH₂OCH₃, —CH₂CN, —CH₂N(CH₃)₂, cyclopropyl, cyclobutyl and monooxacyclobutyl. In some embodiments, R$^a$ is selected from the group consisting of H, methyl, isopropyl, tert-butyl, trifluoromethyl, —CH₂OCH₃, —CH₂CN, —CH₂N(CH₃)₂, cyclopropyl and monooxacyclobutyl. In some embodiments, R$^b$ is selected from the group consisting of methyl, ethyl, trifluoromethyl, pentafluoroethyl, cyclopropyl, cyclobutyl and monooxacyclobutyl.

In some embodiments, R$^a$ or R$^b$ is each independently selected from $C_{1-4}$ alkyl optionally substituted with —OC$_{1-4}$ alkyl.

In some embodiments, R$^a$ or R$^b$ is each independently selected from the group consisting of methyl, isopropyl and —CH₂OCH₃.

In some embodiments, R$^a$ is selected from $C_{1-4}$ alkyl optionally substituted with —OC$_{1-4}$ alkyl. In some embodiments, R$^a$ is selected from the group consisting of methyl, isopropyl and —CH₂OCH₃.

In some embodiments, R$^b$ is selected from $C_{1-4}$ alkyl. In some embodiments, R$^b$ is selected from methyl.

In some embodiments, R³ is selected from 5-6 membered heterocycloalkyl, wherein the 5-6 membered heterocycloalkyl is optionally substituted with —C(O)H, —COCH₃, —COCH(CH₃)₂, —COC(CH₃)₃, —COCF₃, —COCH₂CN, —COCH₂OCH₃, —COCH₂N(CH₃)₂, —SO₂CH₃, —SO₂CH₂CH₃, —SO₂CF₃, —SO₂C₂F₅, methyl, ethyl, —CF₃, —CH₂CH₂F, —C₂F₅, tetrahydropyran, monooxacyclobutane, —SO₂-cyclopropane, —CO-cyclopropane, —CO-monooxacyclobutane, —SO₂-monooxacyclobutane or —SO₂-cyclobutane.

In some embodiments, R³ is selected from 5-6 membered heterocycloalkyl, wherein the 5-6 membered heterocycloalkyl is optionally substituted with —COCH₃, —COCH(CH₃)₂, —COCH₂OCH₃, —SO₂CH₃, methyl, ethyl or —CH₂CH₂F.

In some embodiments, R³ is selected from 5-6 membered heterocycloalkyl, wherein the 5-6 membered heterocycloalkyl is optionally substituted with —C(O)H, —COC(CH₃)₃, —COCF₃, —COCH₂CN, —COCH₂N(CH₃)₂, —SO₂CH₂CH₃, —SO₂CF₃, —SO₂C₂F₅, —CF₃, —C₂F₅, tetrahydropyran, monooxacyclobutane, —SO₂-cyclopropane, —CO-cyclopropane, —CO-monooxacyclobutane, —SO₂-monooxacyclobutane or —SO₂-cyclobutane.

In some embodiments, R³ is selected from the group consisting of tetrahydropyran, piperidine, morpholine and dioxane, wherein the tetrahydropyran, piperidine, morpholine or dioxane is optionally substituted with —COCH₃, —COCH(CH₃)₂, —COCH₂OCH₃, —SO₂CH₃, methyl, ethyl or —CH₂CH₂F.

In some embodiments, R³ is selected from 5-6 membered heterocycloalkyl, wherein the 5-6 membered heterocycloalkyl is optionally substituted with —COCH₃, —COCH(CH₃)₂, —COCH₂OCH₃, or —SO₂CH₃.

In some embodiments, R³ is selected from the group consisting of tetrahydrofuran, tetrahydropyran, dioxane and morpholine, wherein the morpholine is optionally substituted with —COCH₃, —COCH(CH₃)₂, —COCH₂OCH₃ or —SO₂CH₃.

In some embodiments, R³ is selected from the group consisting of tetrahydrofuran, tetrahydropyran, dioxane and morpholine.

In some embodiments, R³ is selected from the group consisting of tetrahydropyran and dioxane.

In some embodiments, R³ is selected from the group consisting of piperidine and morpholine, wherein the piperidine or morpholine is optionally substituted with —COCH₃, —COCH(CH₃)₂, —COCH₂OCH₃, —SO₂CH₃, methyl, ethyl or —CH₂CH₂F.

In some embodiments, R³ is selected from the group consisting of

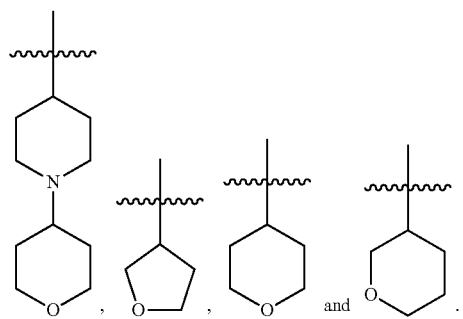

In some embodiments, $R^3$ is selected from the group consisting of
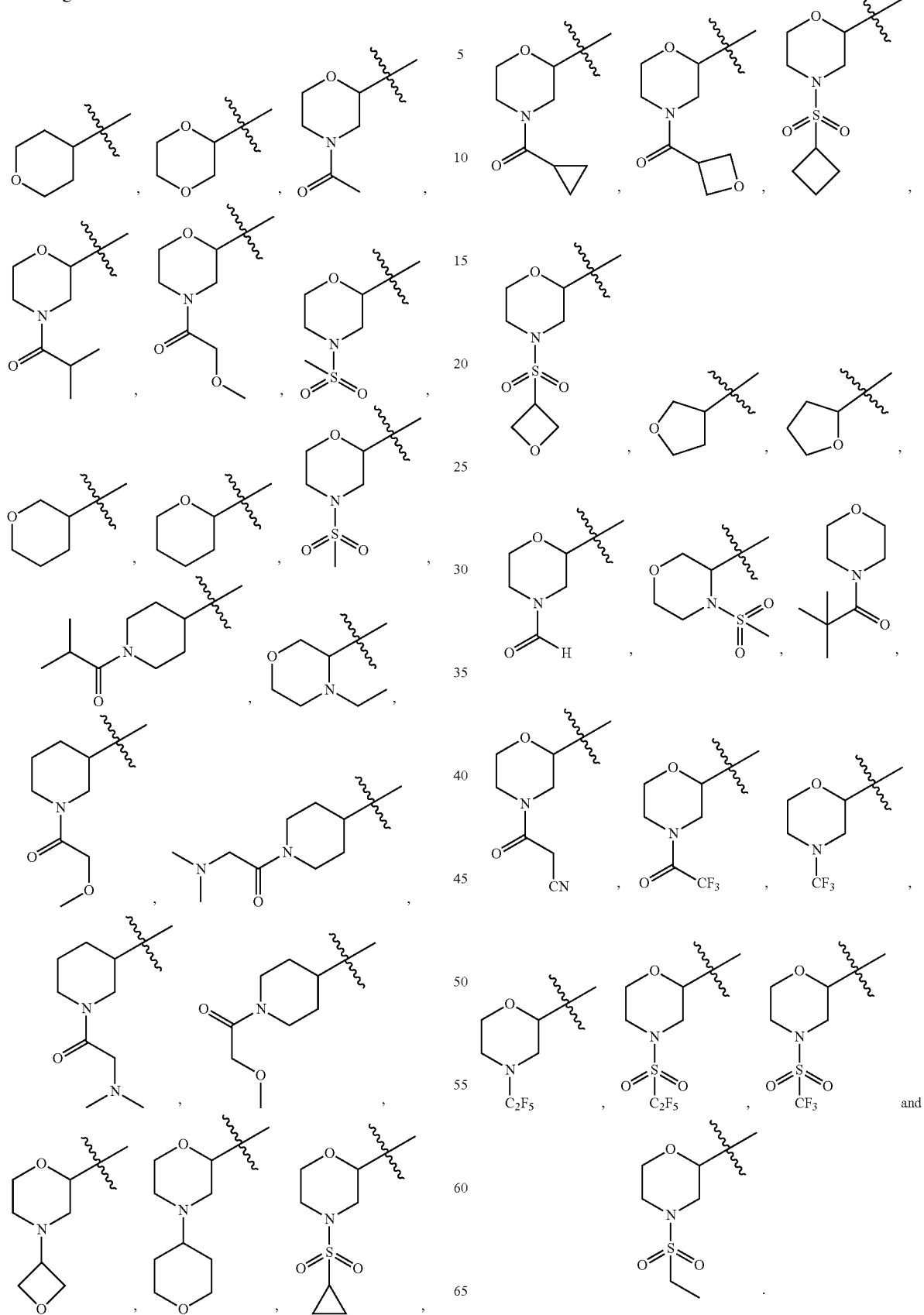

In some embodiments, $R^3$ is selected from the group consisting of
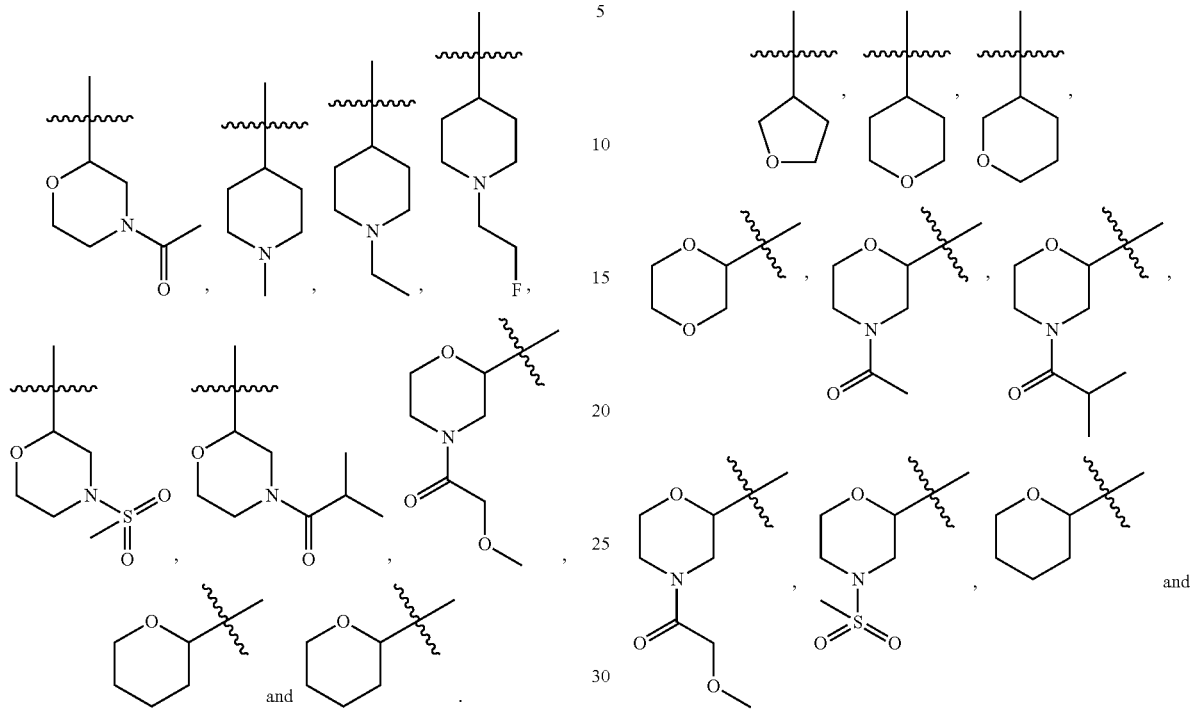
In some embodiments, $R^3$ is selected from the group consisting of
In some embodiments, $R^3$ is selected from the group consisting of
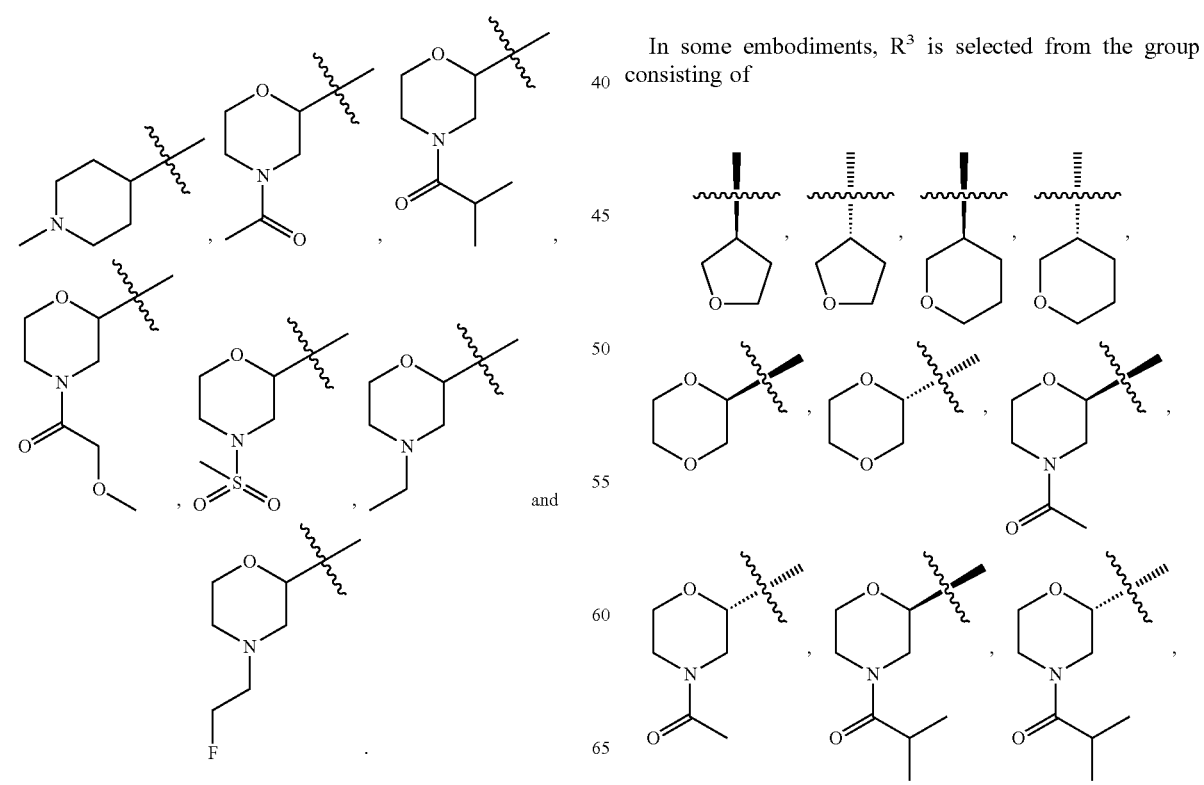
In some embodiments, $R^3$ is selected from the group consisting of

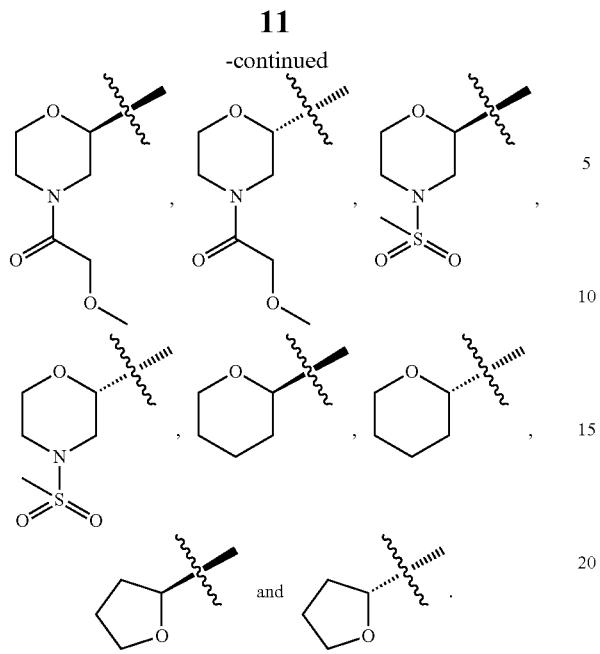

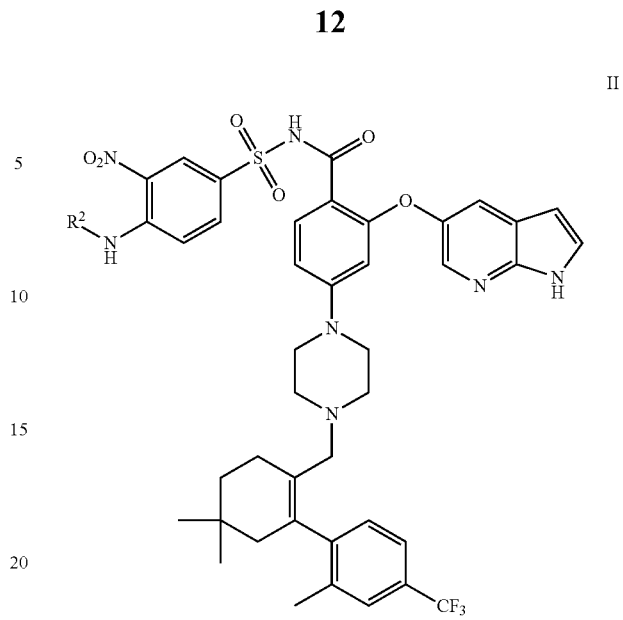

In some embodiments, the heteroatom in the 5-6 membered heterocycloalkyl is selected from the group consisting of N and O, and the number of the heteroatom is selected from the group consisting of 1 and 2.

In some embodiments, the 5-6 membered heterocycloalkyl is selected from the group consisting of dioxanyl, morpholinyl, tetrahydropyranyl, piperidinyl and tetrahydrofuranyl.

In some embodiments, the 5-6 membered heterocycloalkyl is selected from 6 membered heterocycloalkyl.

In some embodiments, the 5-6 membered heterocycloalkyl is selected from the group consisting of dioxanyl, morpholinyl, tetrahydropyranyl and piperidinyl.

In some embodiments, the 5-6 membered heterocycloalkyl is selected from dioxanyl.

In some embodiments, the 5-6 membered heterocycloalkyl is selected from morpholinyl.

In some embodiments, the 5-6 membered heterocycloalkyl is selected from tetrahydropyranyl.

In some embodiments, the 5-6 membered heterocycloalkyl is selected from tetrahydrofuranyl.

In some embodiments, the heteroatom in the 3-6 membered heterocycloalkyl is selected from the group consisting of N and O, and the number of the heteroatom is selected from the group consisting of 1 and 2. In some embodiments, the heteroatom in the 3-6 membered heterocycloalkyl is selected from O, and the number of the heteroatom is selected from the group consisting of 1 and 2. In some embodiments, the 3-6 membered heterocycloalkyl is selected from 4-6 membered heterocycloalkyl. In some embodiments, the 3-6 membered heterocycloalkyl is selected from the group consisting of 4-membered heterocycloalkyl and 6-membered heterocycloalkyl.

In some embodiments, the 3-6 membered heterocycloalkyl is selected from the group consisting of monooxacyclobutyl, tetrahydrofuranyl and tetrahydropyranyl.

In some embodiments, the $C_{3-6}$ cycloalkyl is selected from the group consisting of cyclopropyl, cyclobutyl and cyclopentyl. In some embodiments, the $C_{3-6}$ cycloalkyl is selected from $C_{3-4}$ cycloalkyl.

In another aspect, the present application relates to a compound of formula II, a stereoisomer thereof or a pharmaceutically acceptable salt thereof:

wherein $R^2$ is defined as in the compound of formula I.

The present application relates to a compound of a formula selected from the group consisting of the following formulas, a stereoisomer thereof or a pharmaceutically acceptable salt thereof:

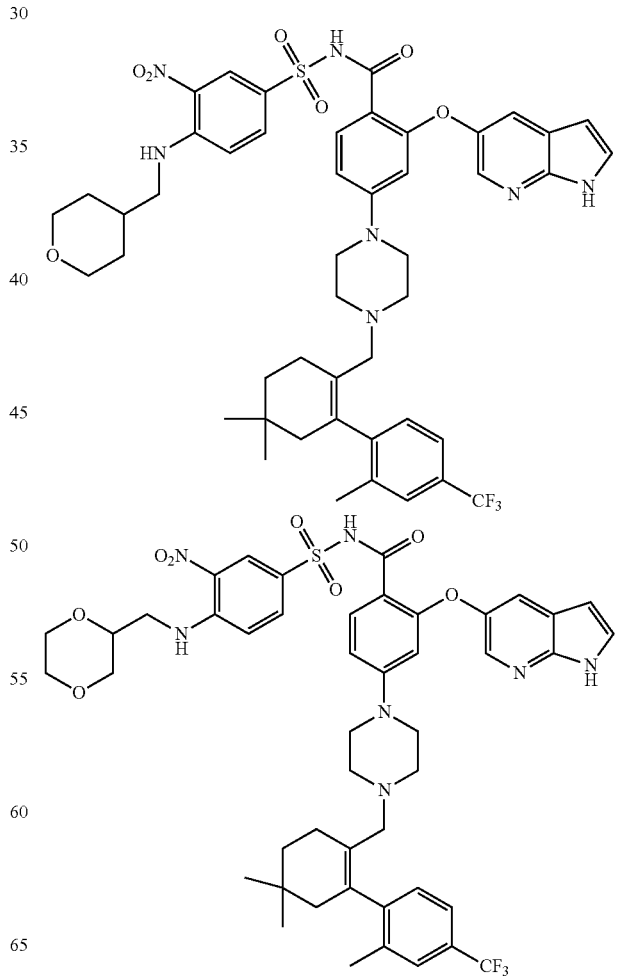

13
-continued
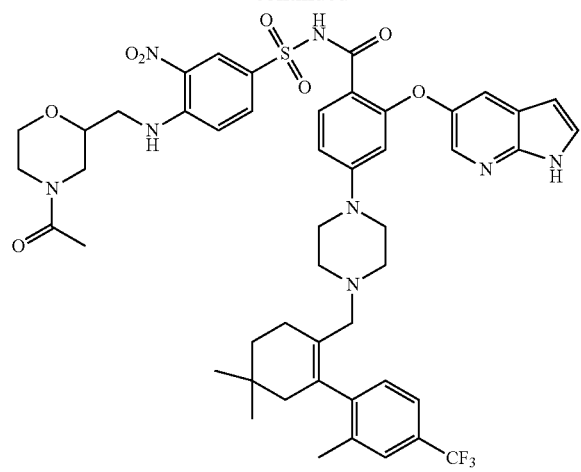
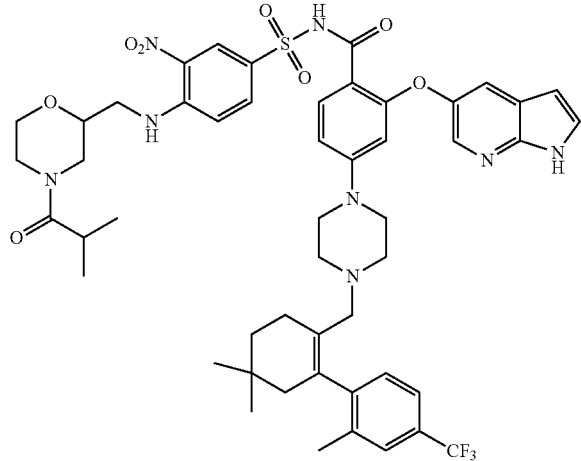
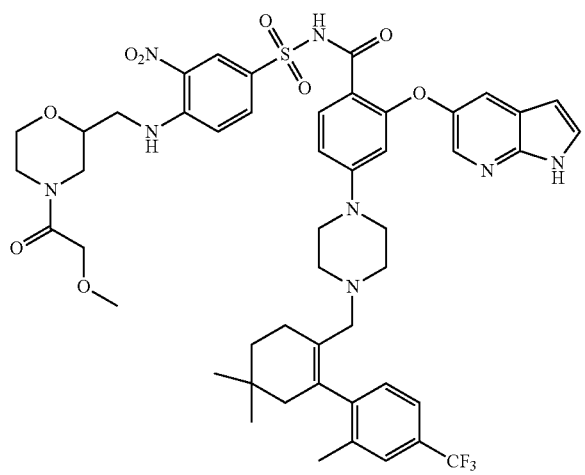
14
-continued
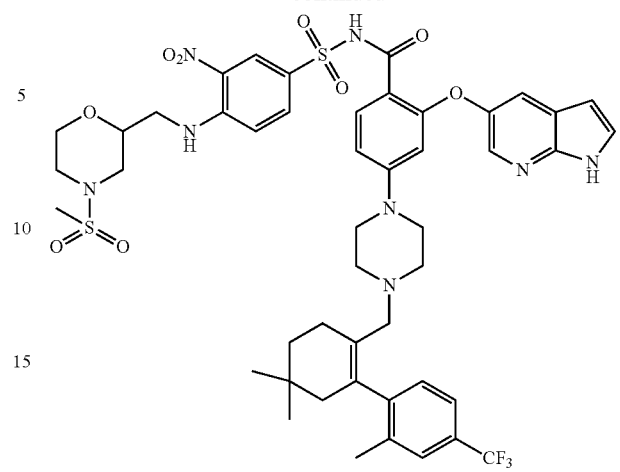
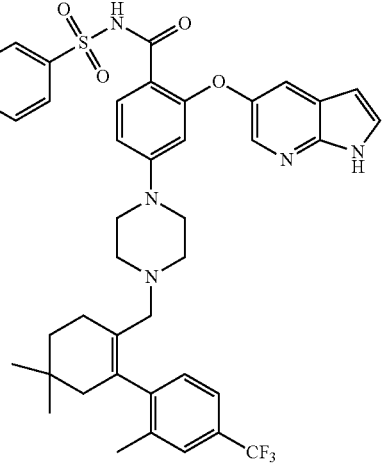
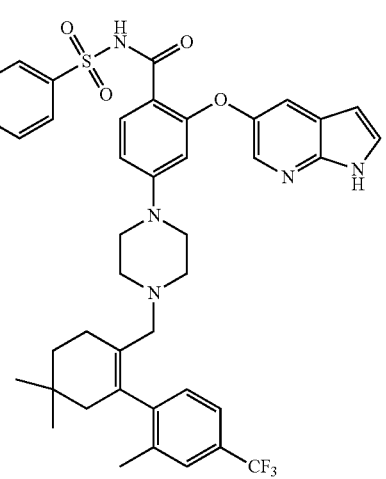

15
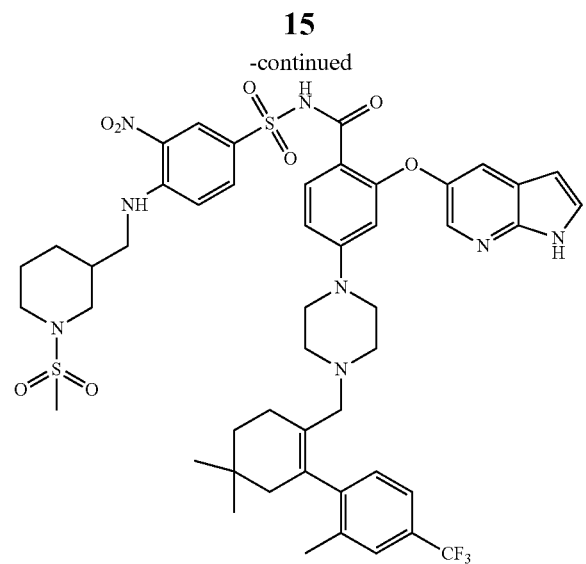
16
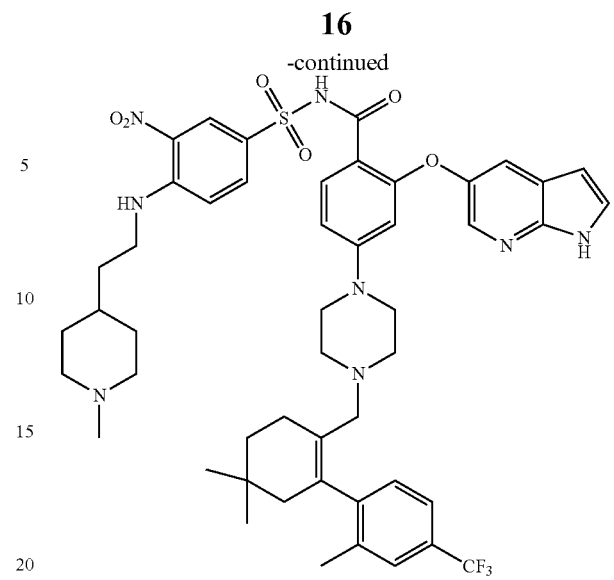
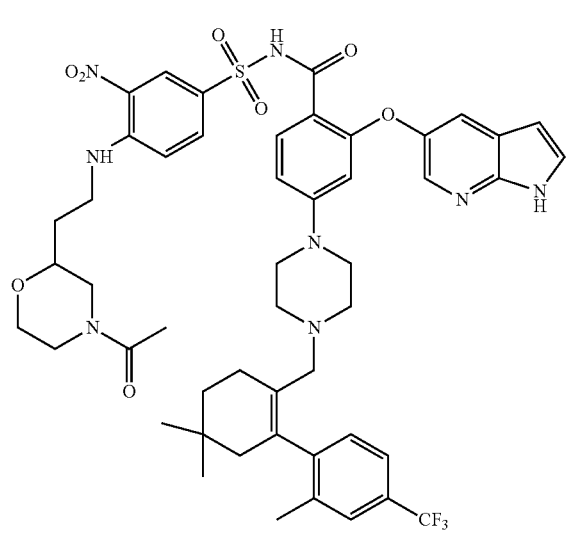
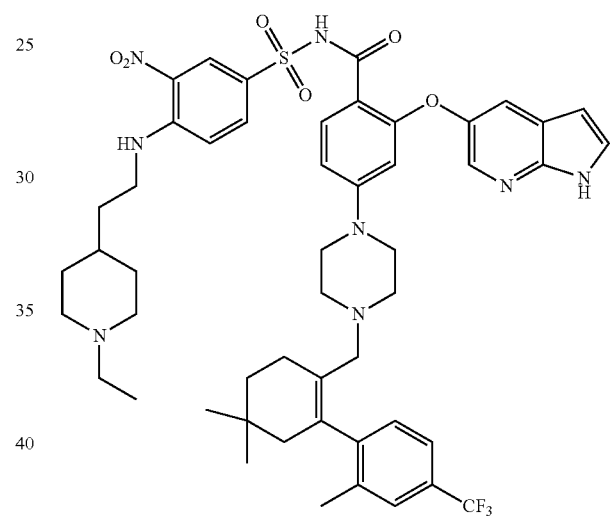
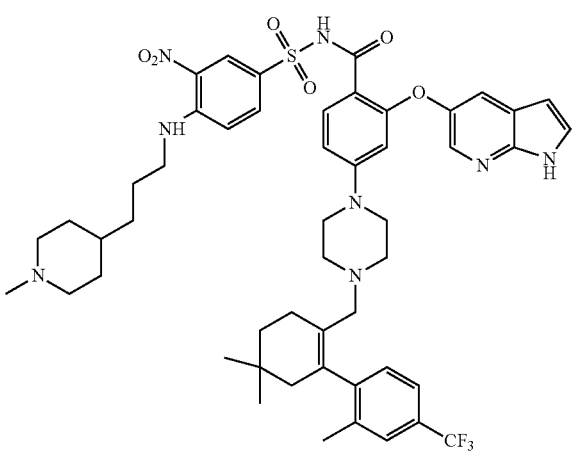
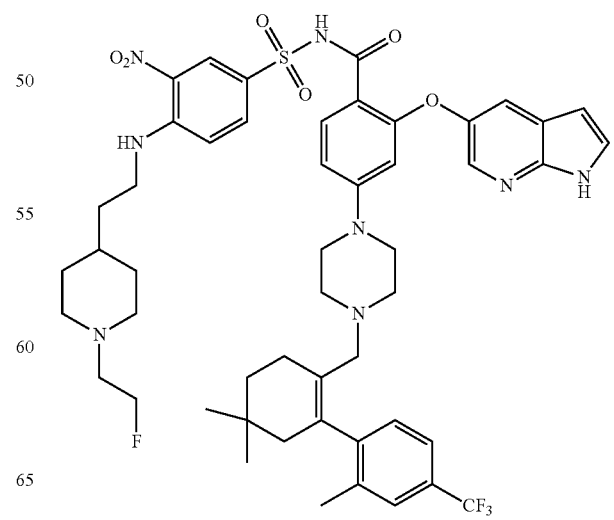

17
-continued
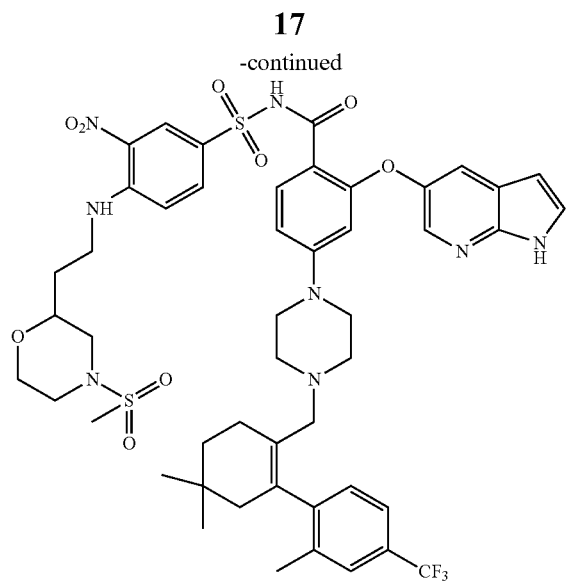
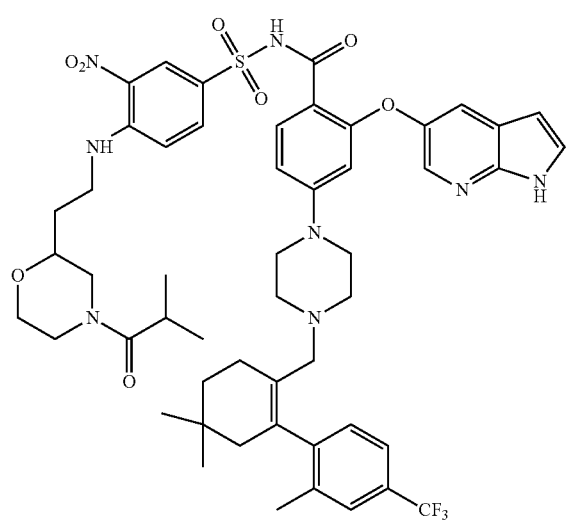
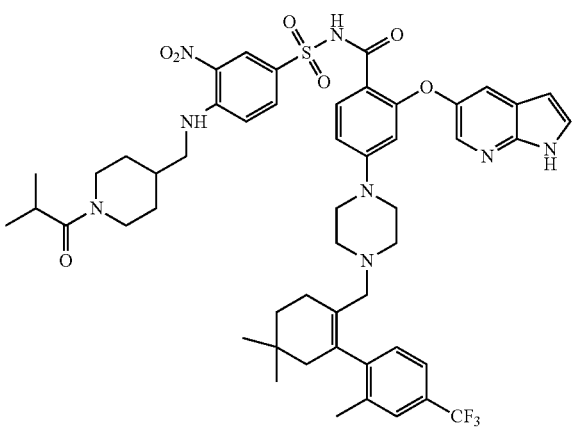
18
-continued
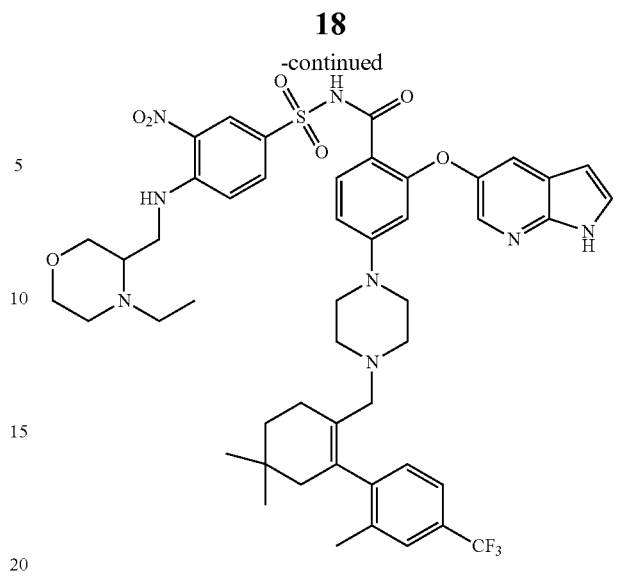
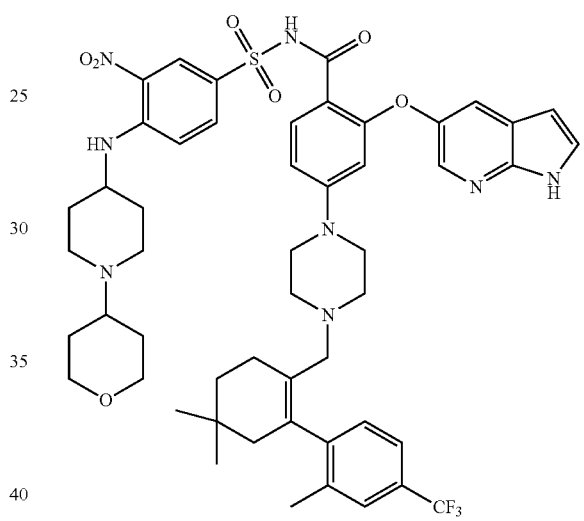
or a compound of the following formula, a stereoisomer thereof or a pharmaceutically acceptable salt thereof:
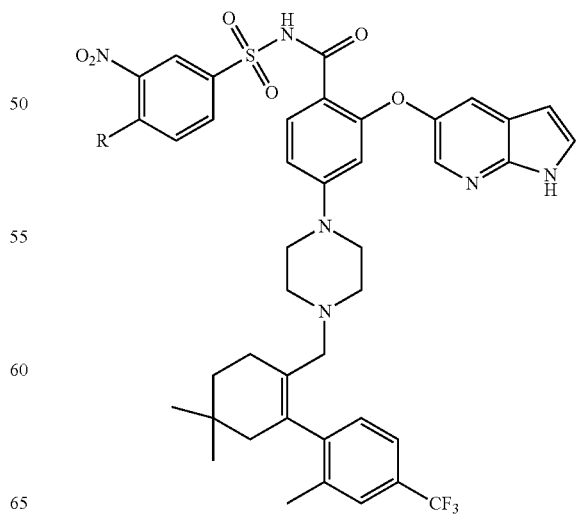

wherein R is independently selected from the group consisting of:
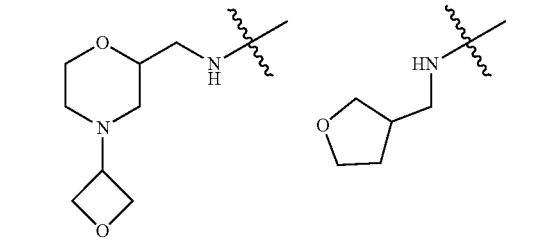
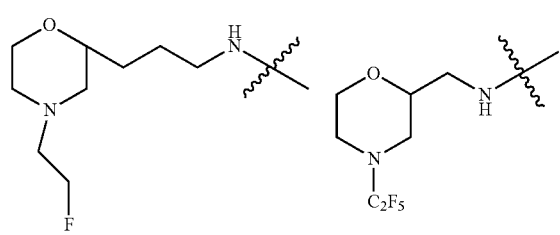
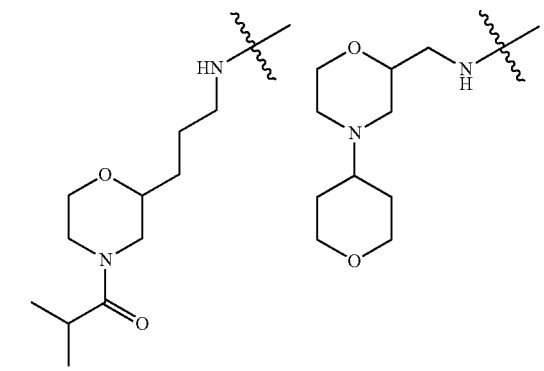
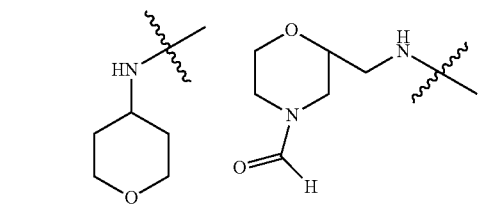
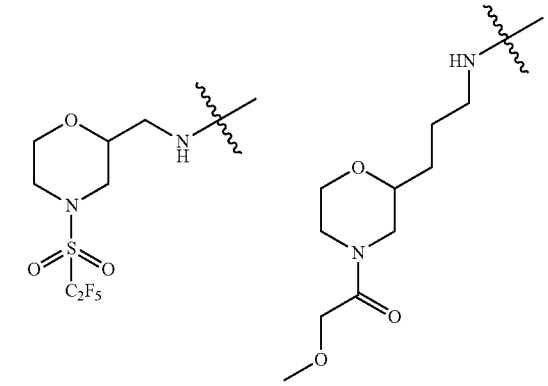
-continued
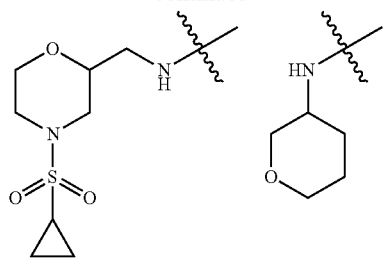
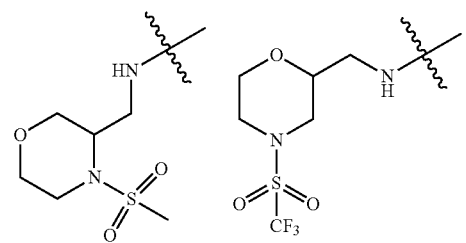

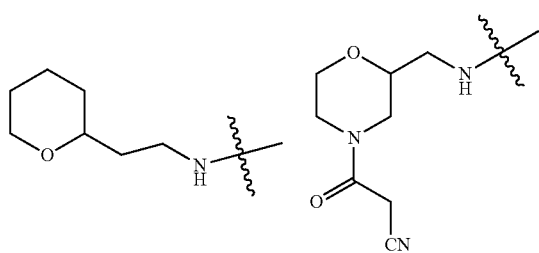
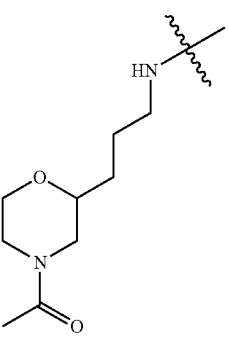
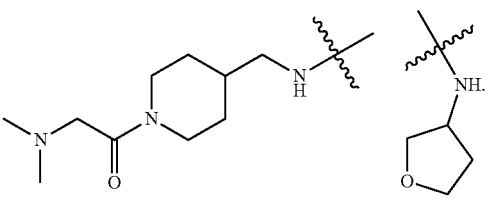
The present application relates to a compound of a formula selected from the group consisting of the following formulas or a pharmaceutically acceptable salts thereof:
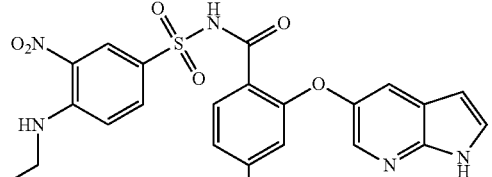
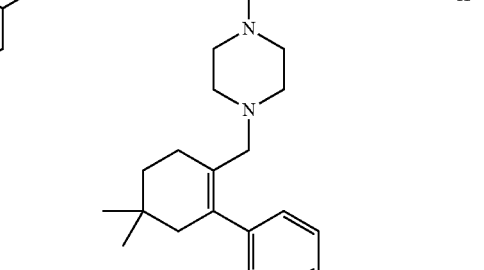
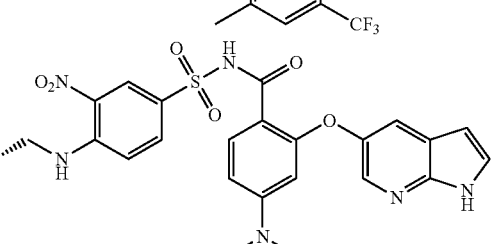
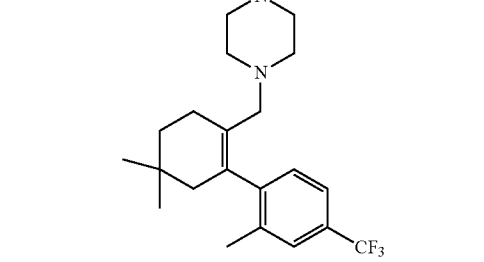

23
-continued
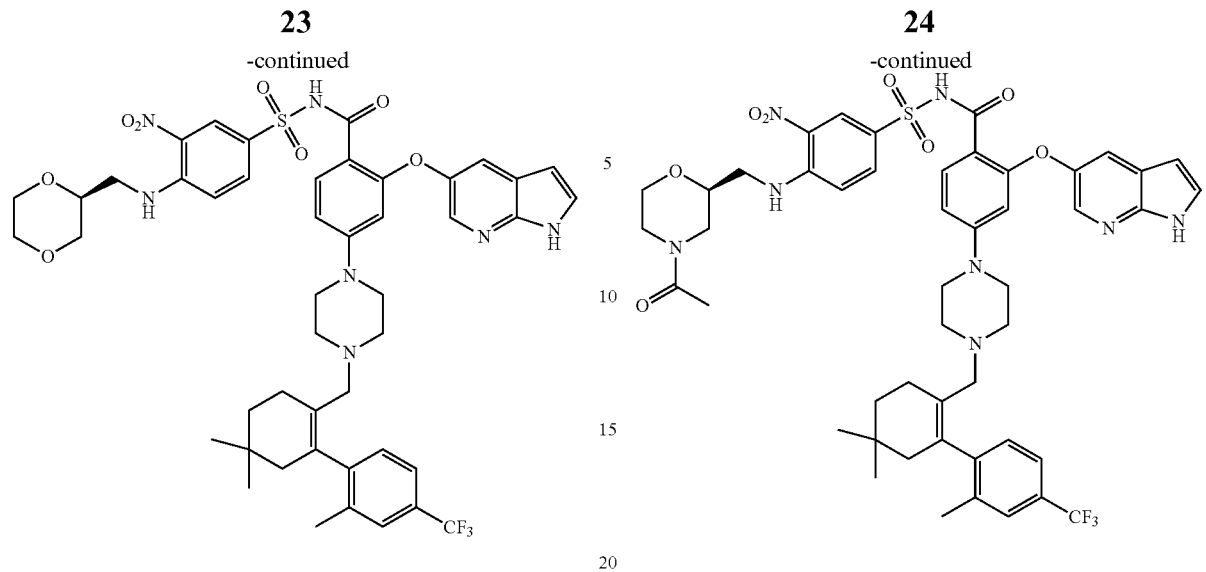
24
-continued
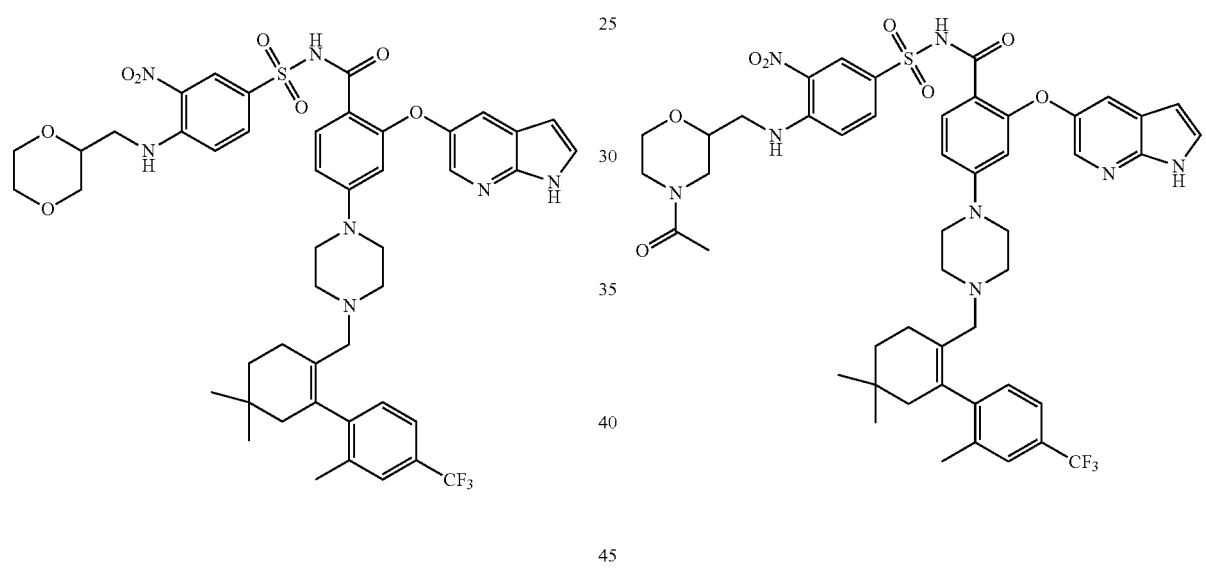
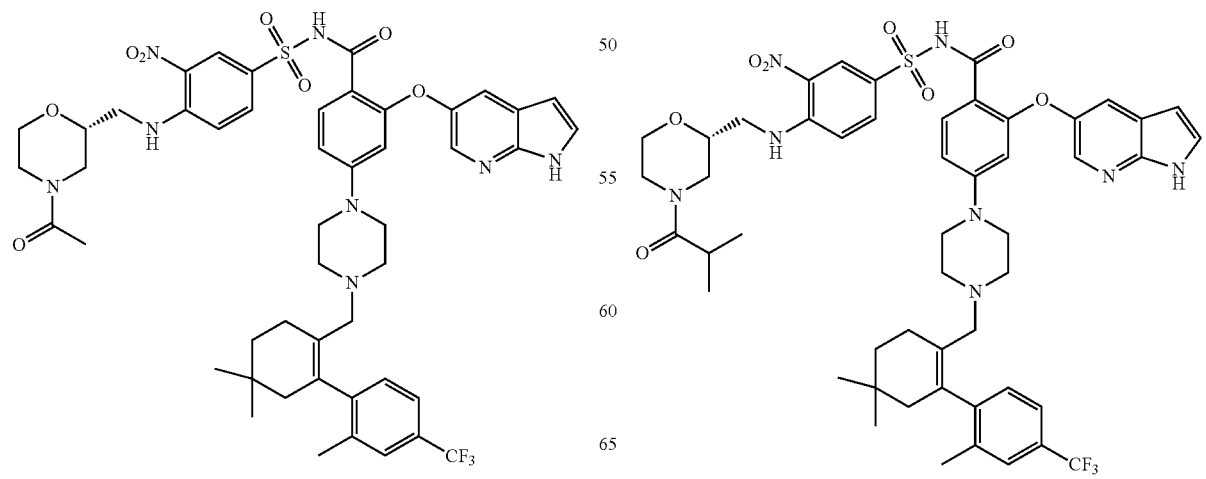

25
-continued
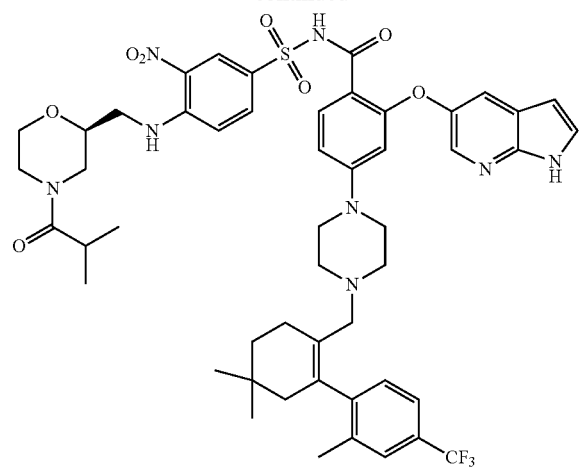
26
-continued
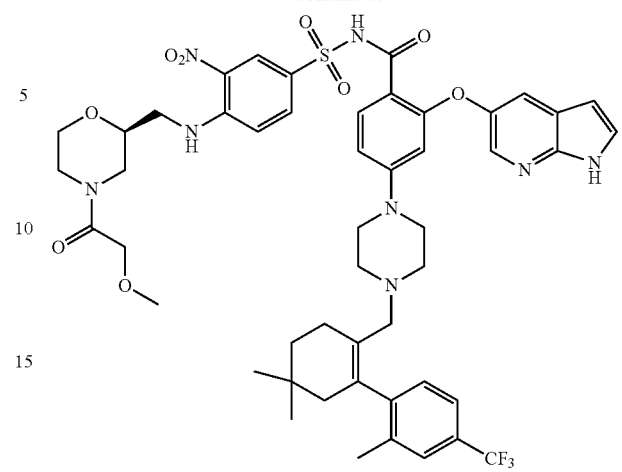
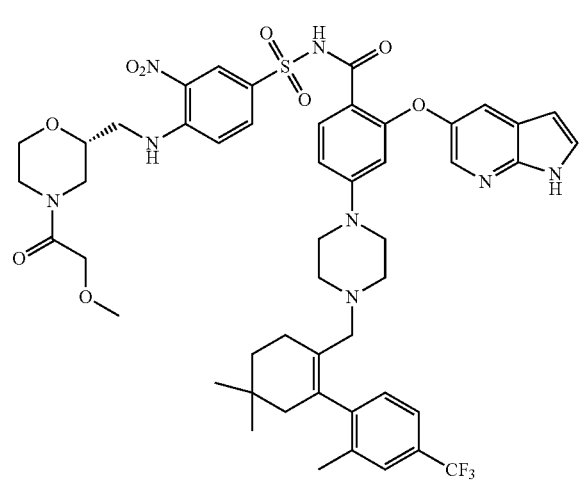

27
-continued
28
-continued
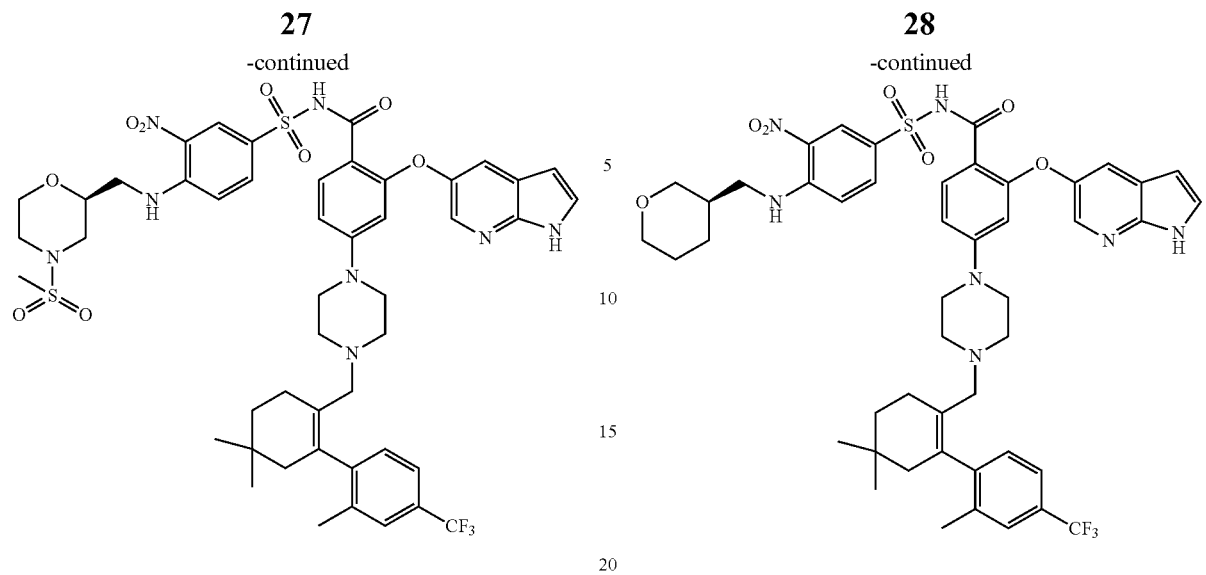
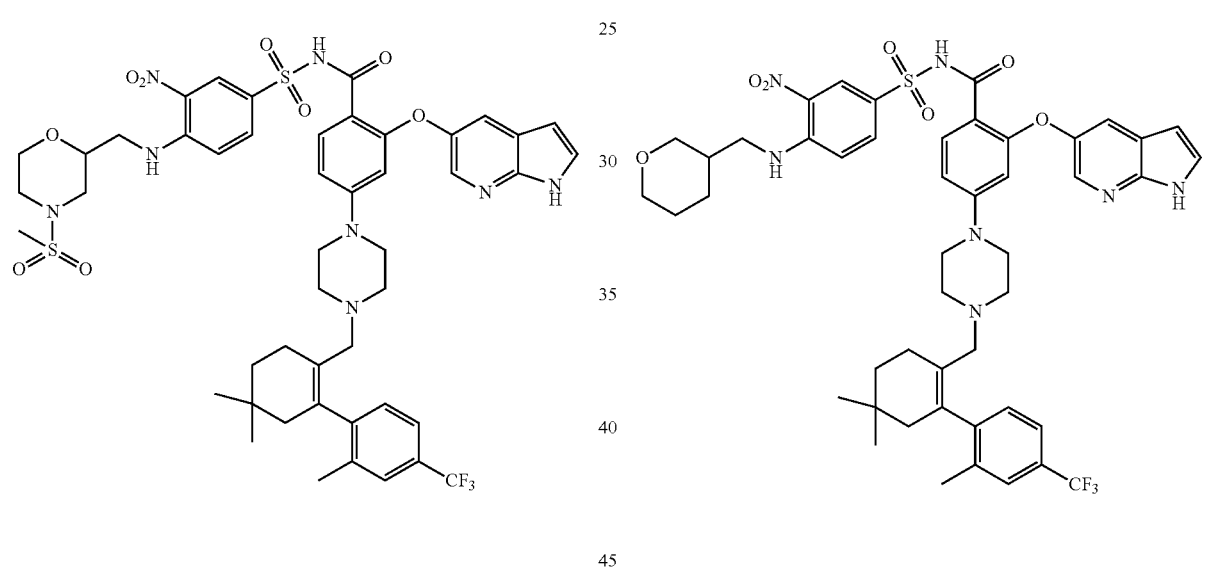
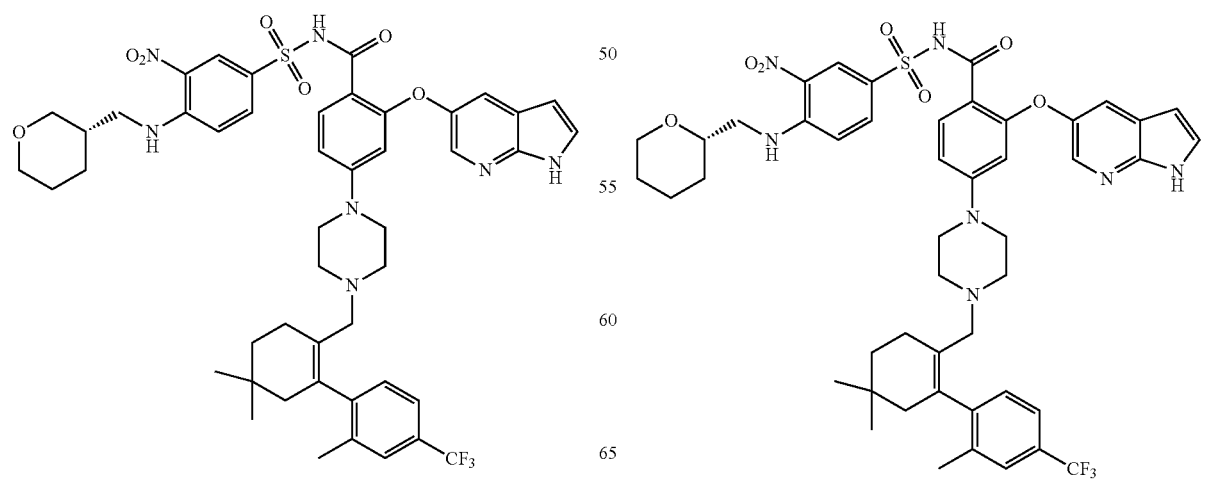

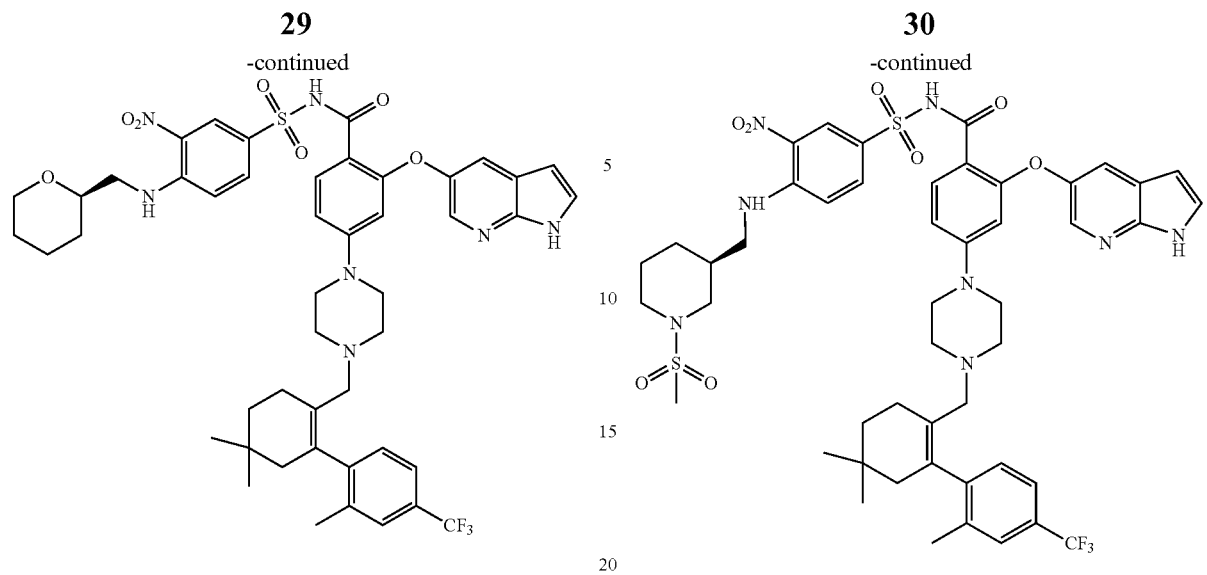
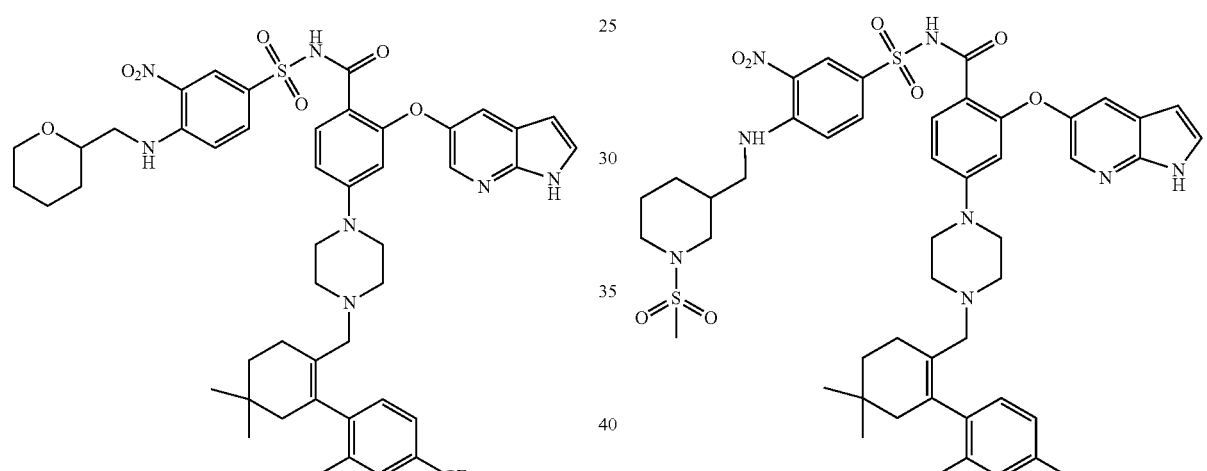
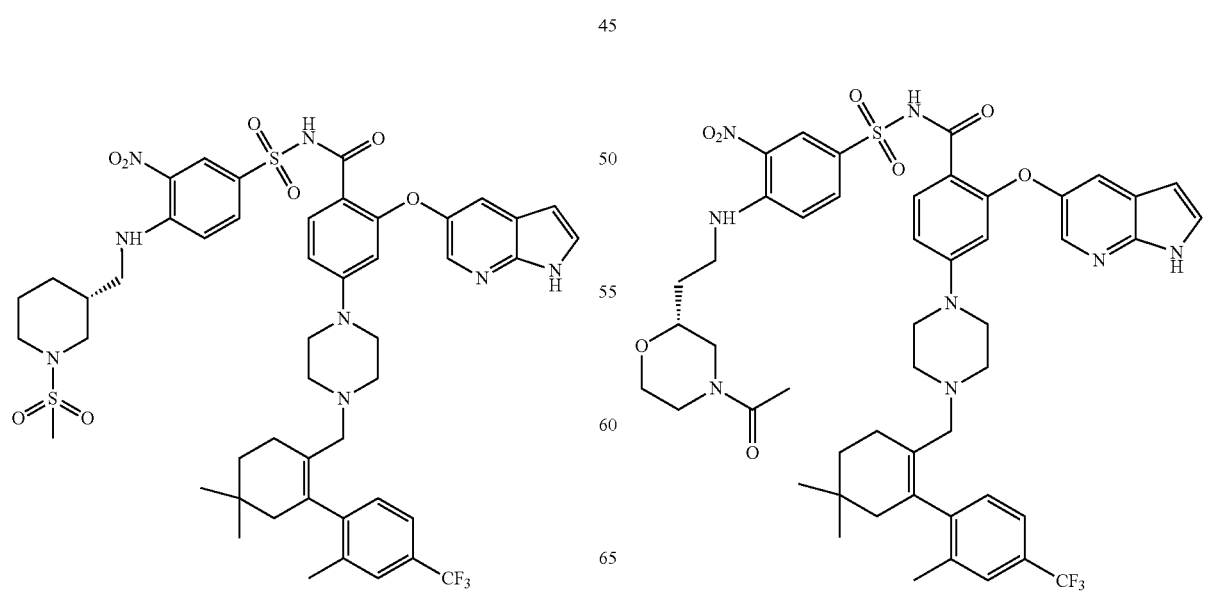

31
-continued
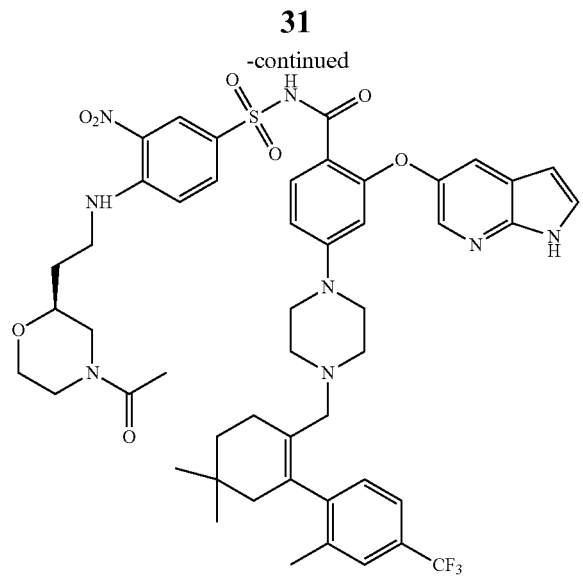
32
-continued
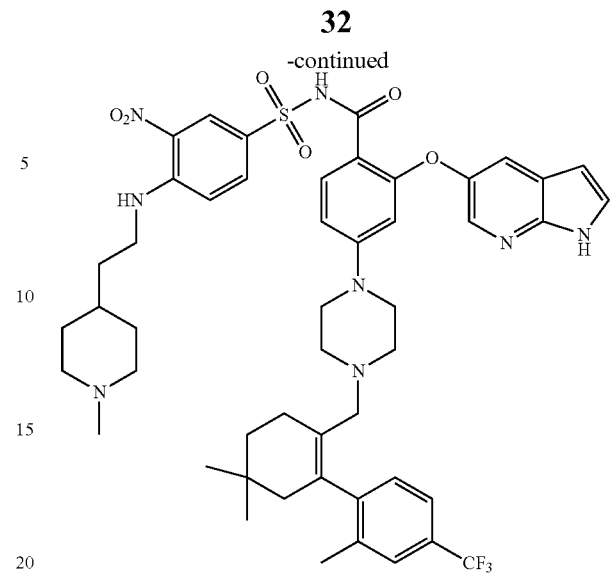
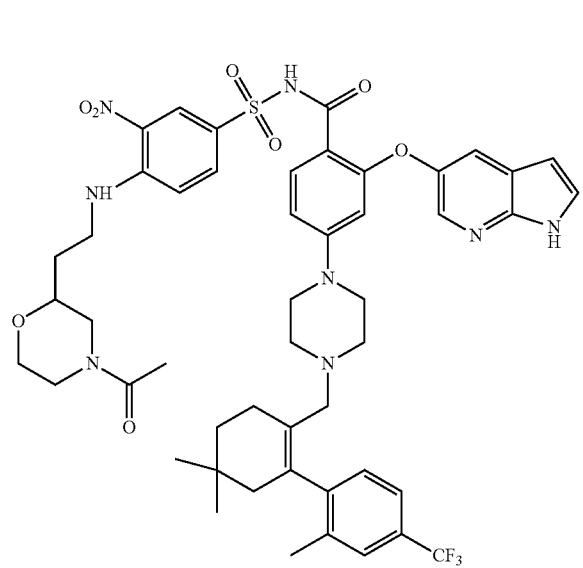
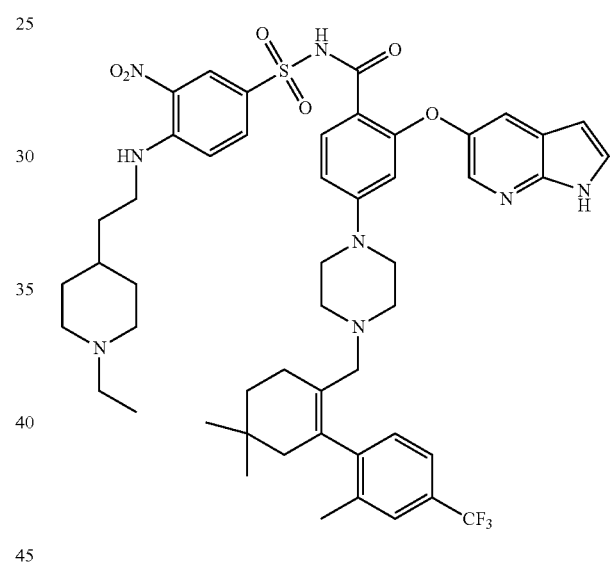
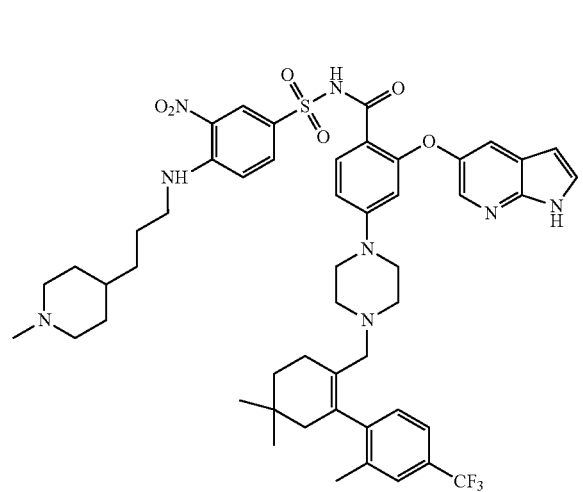
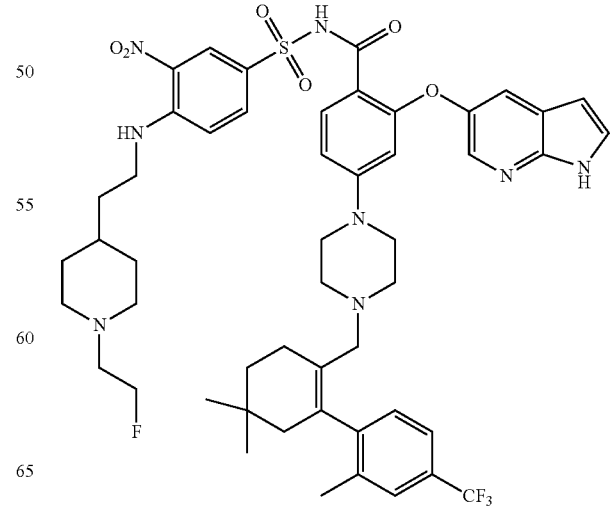

33 -continued
34 -continued
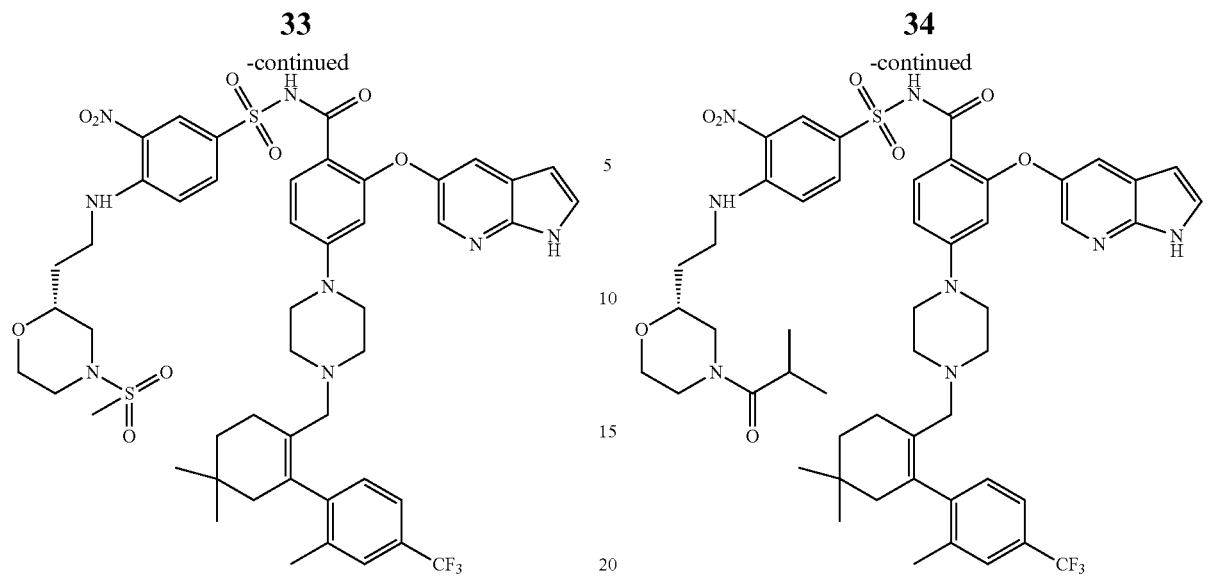
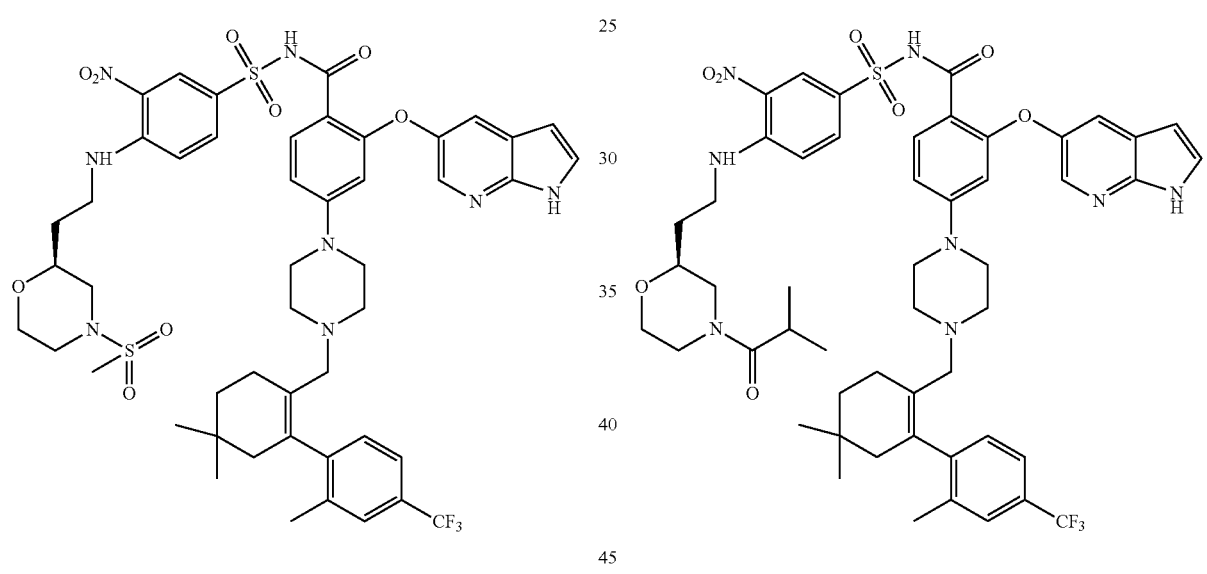
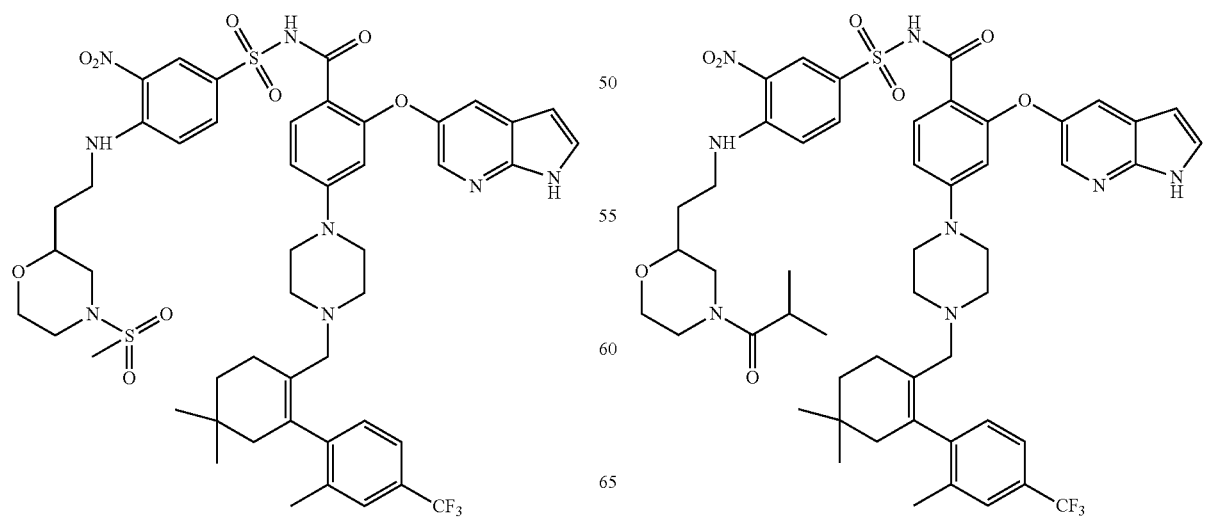

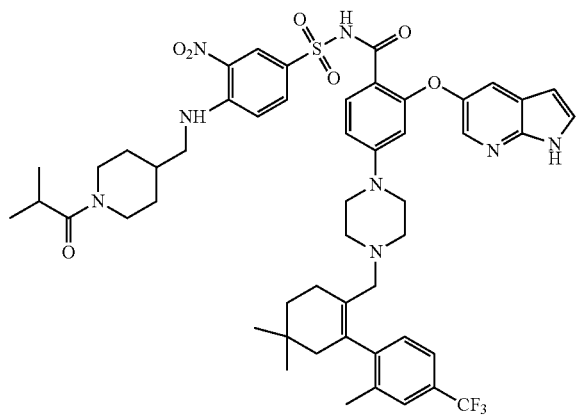
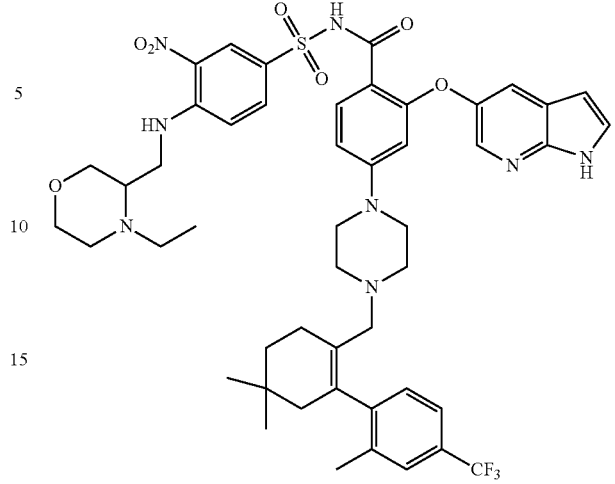
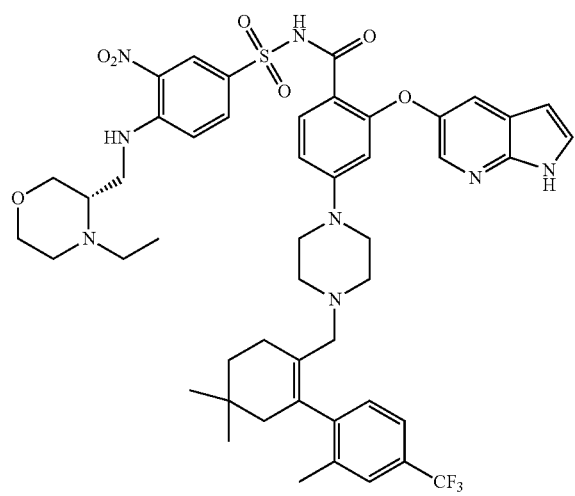
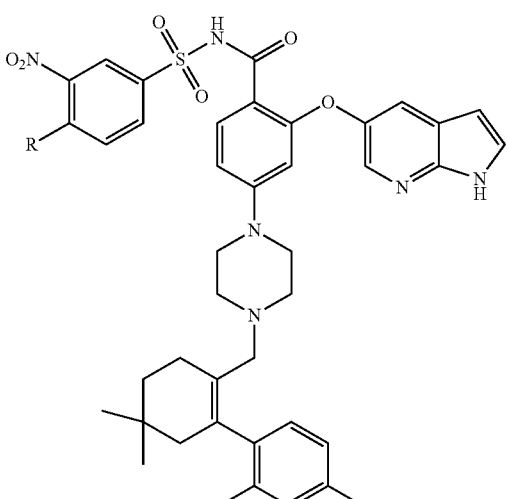
or the following formulas or a pharmaceutically acceptable salts thereof:
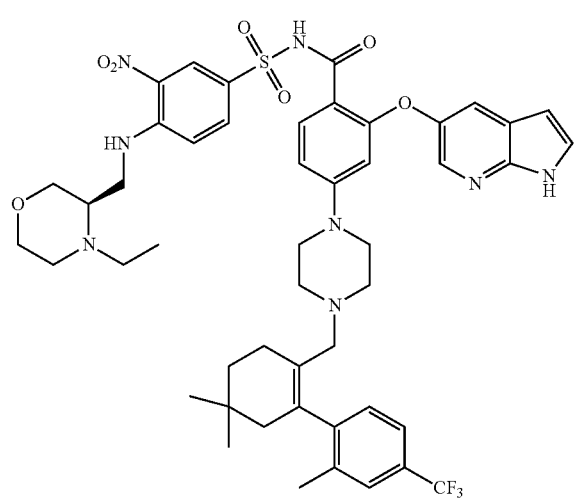

wherein R is independently selected from the group consisting of:
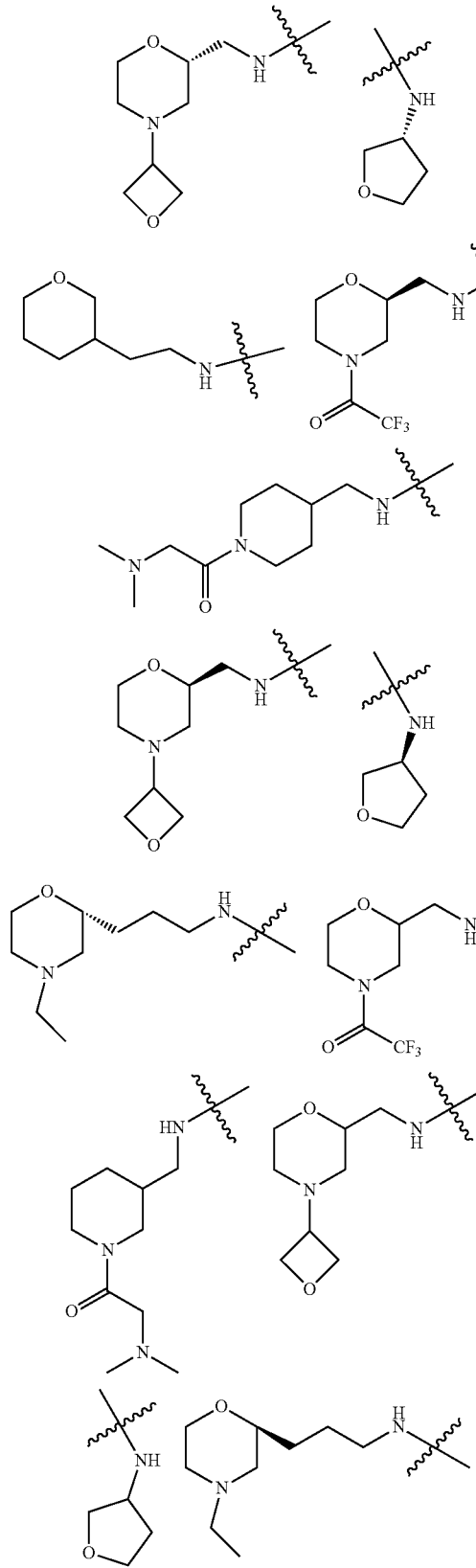
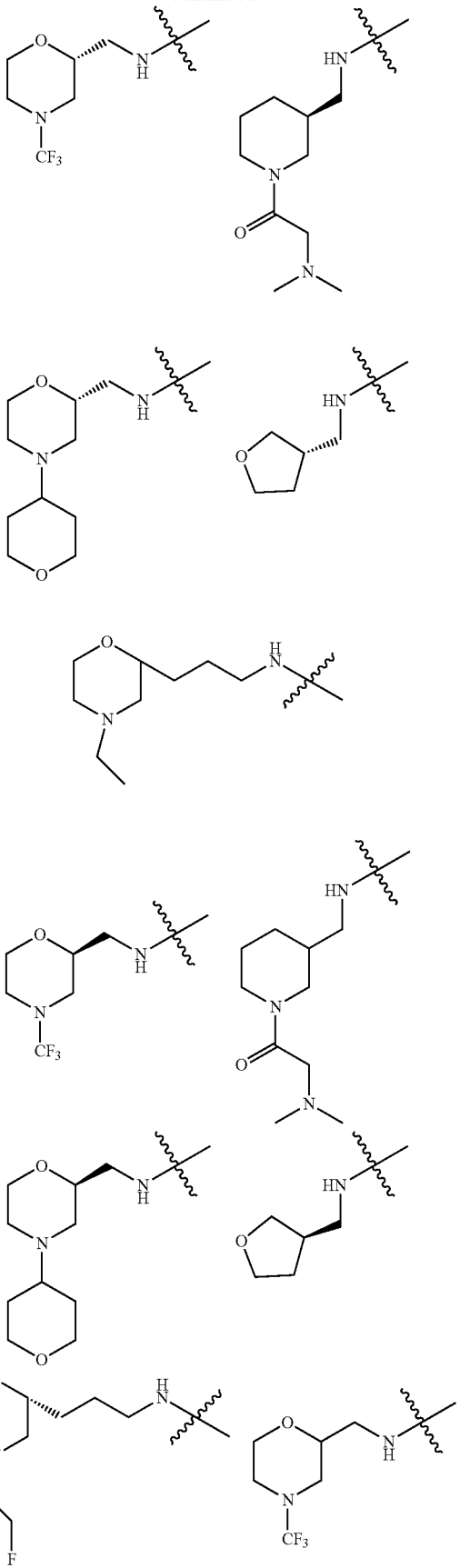

-continued
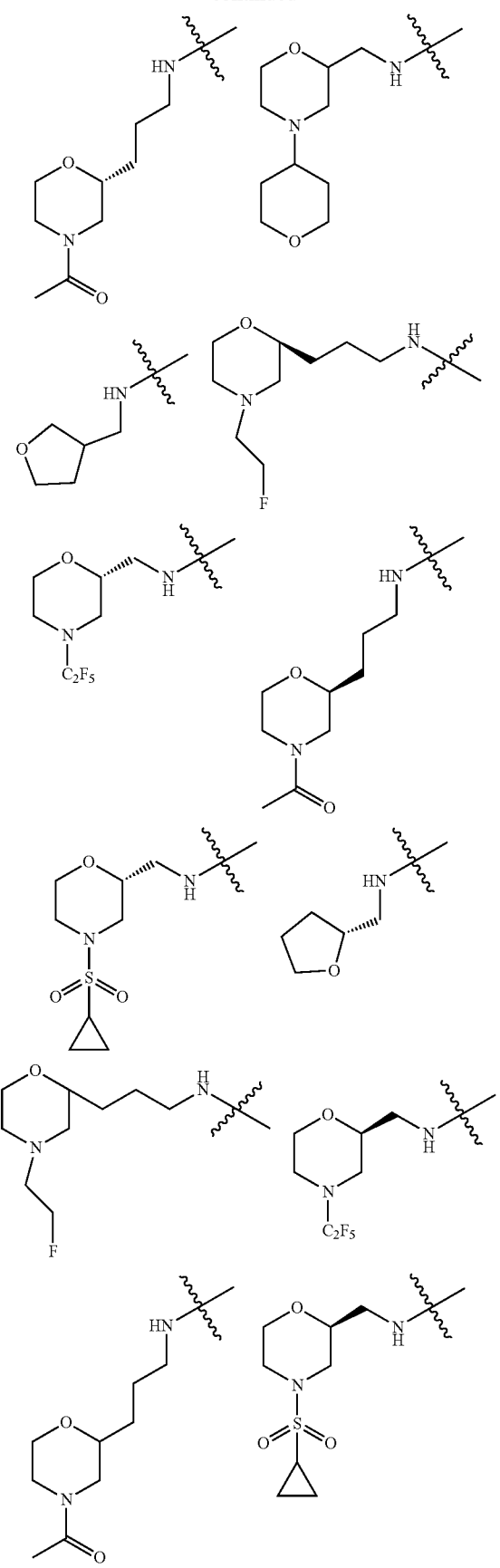
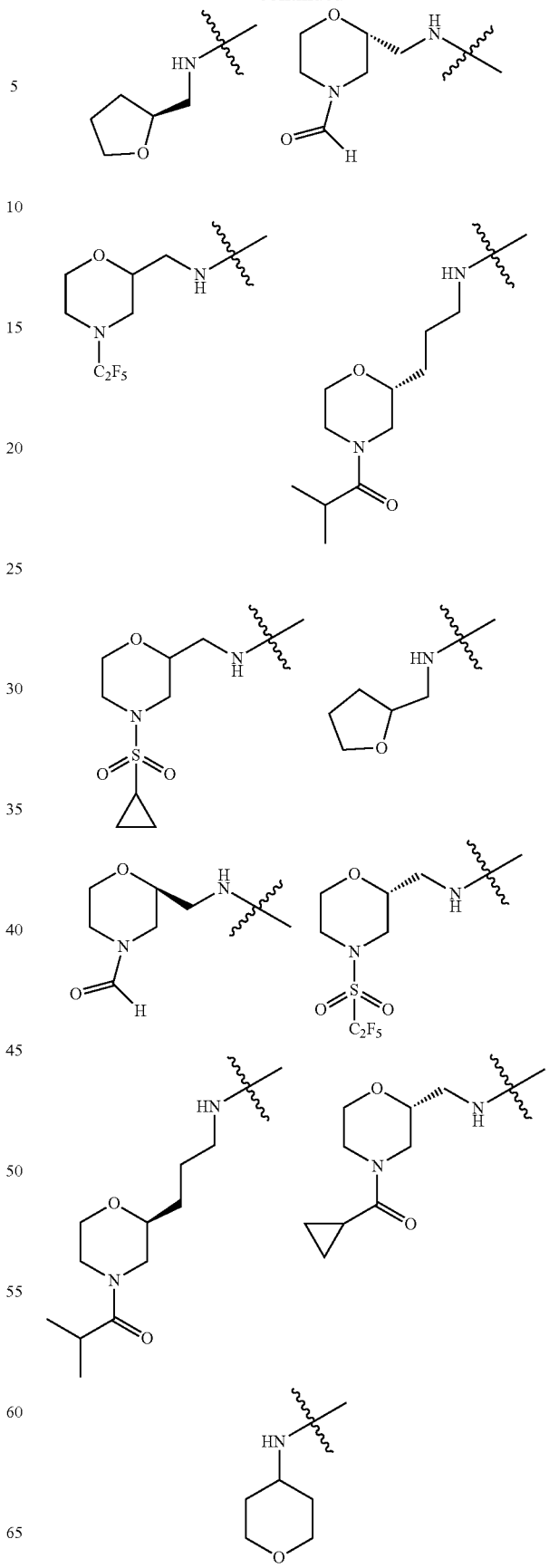

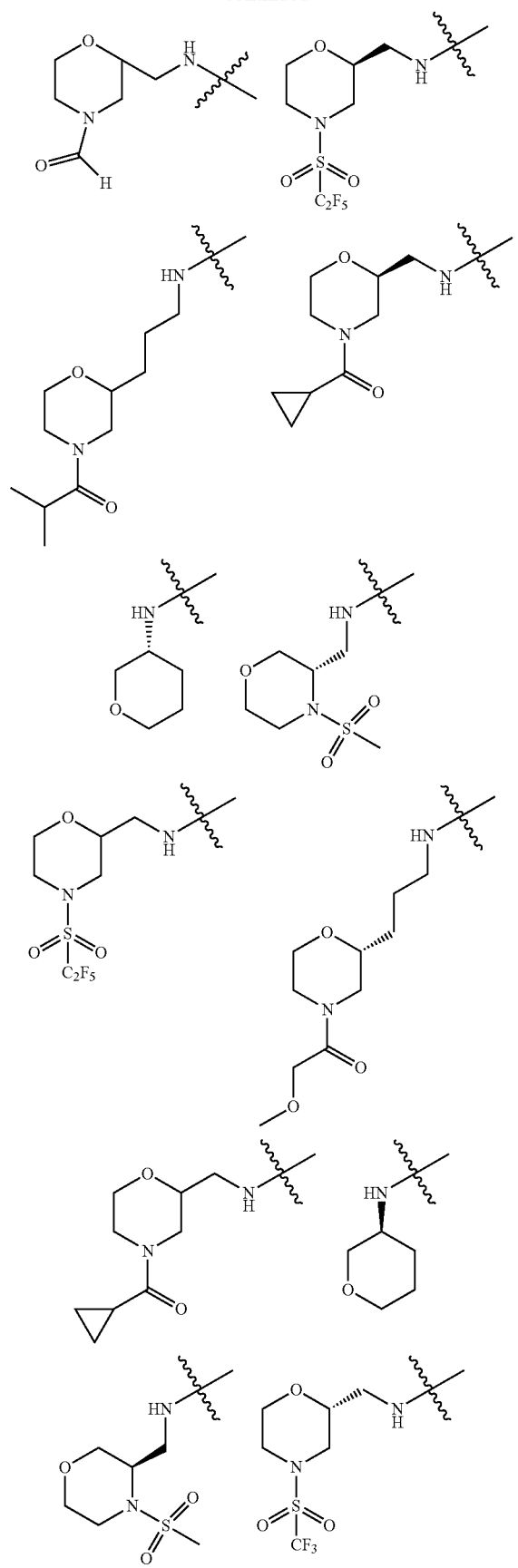
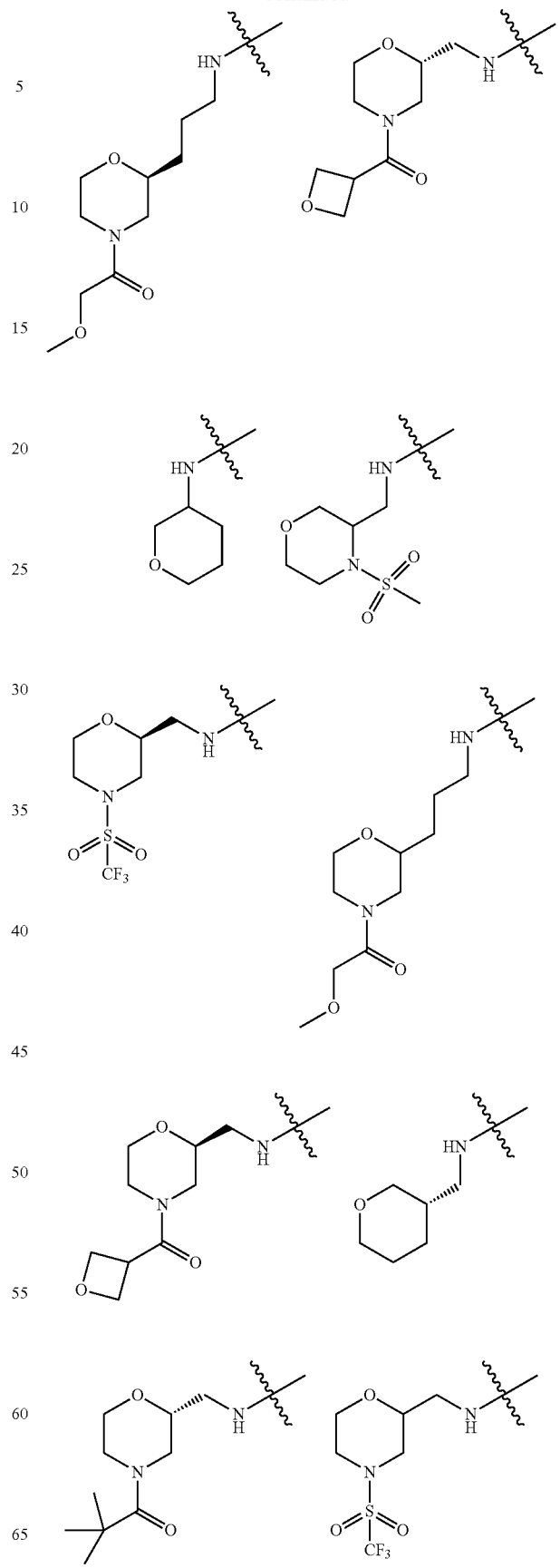

-continued
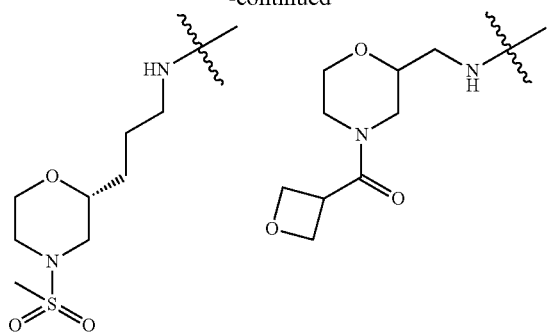
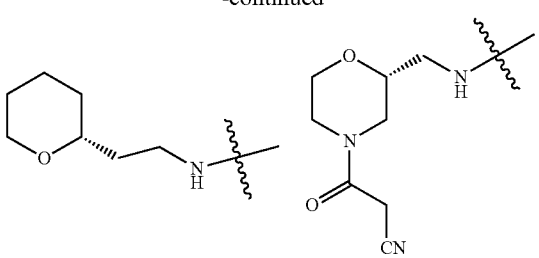
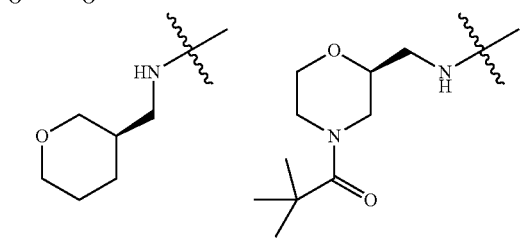
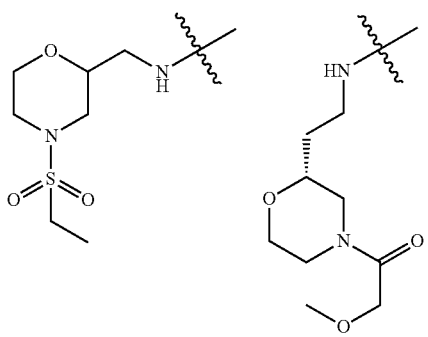
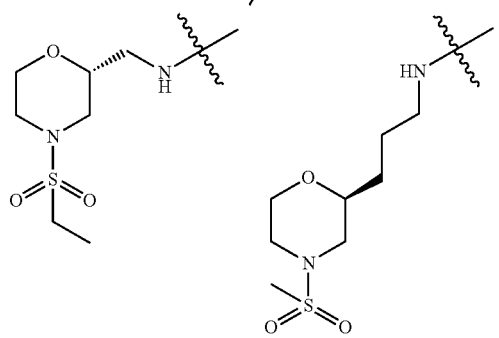
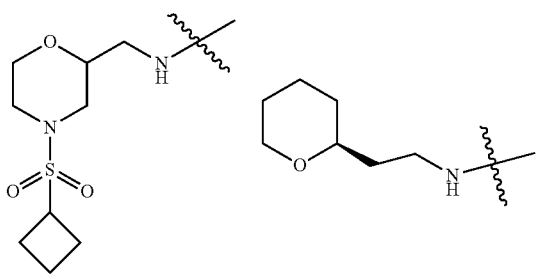
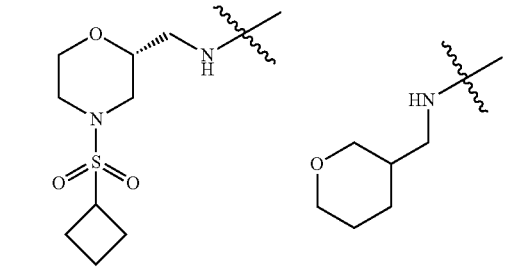
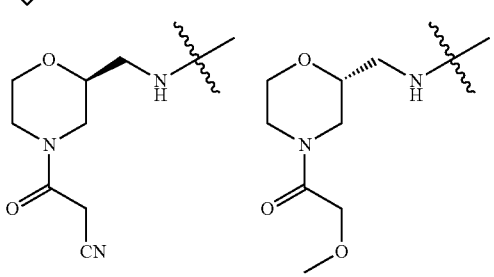
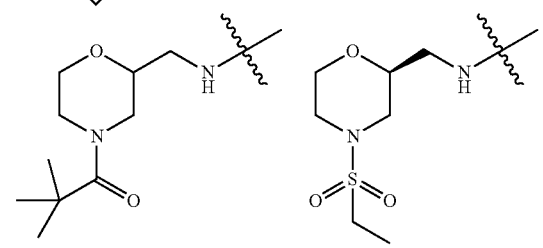
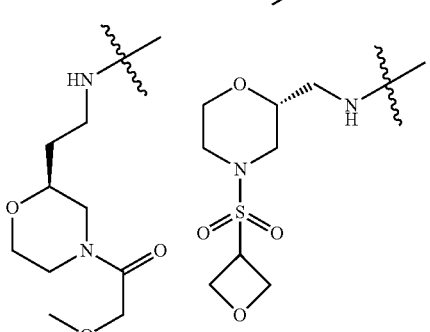
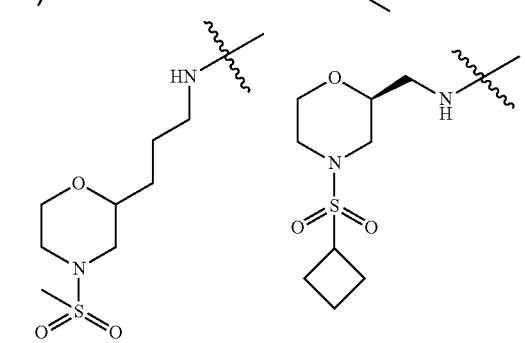
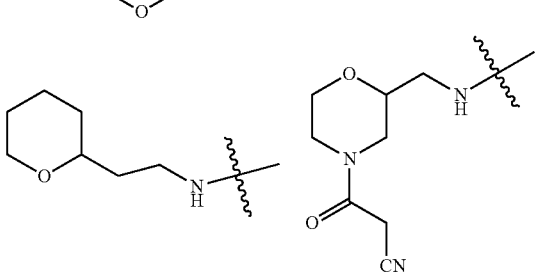

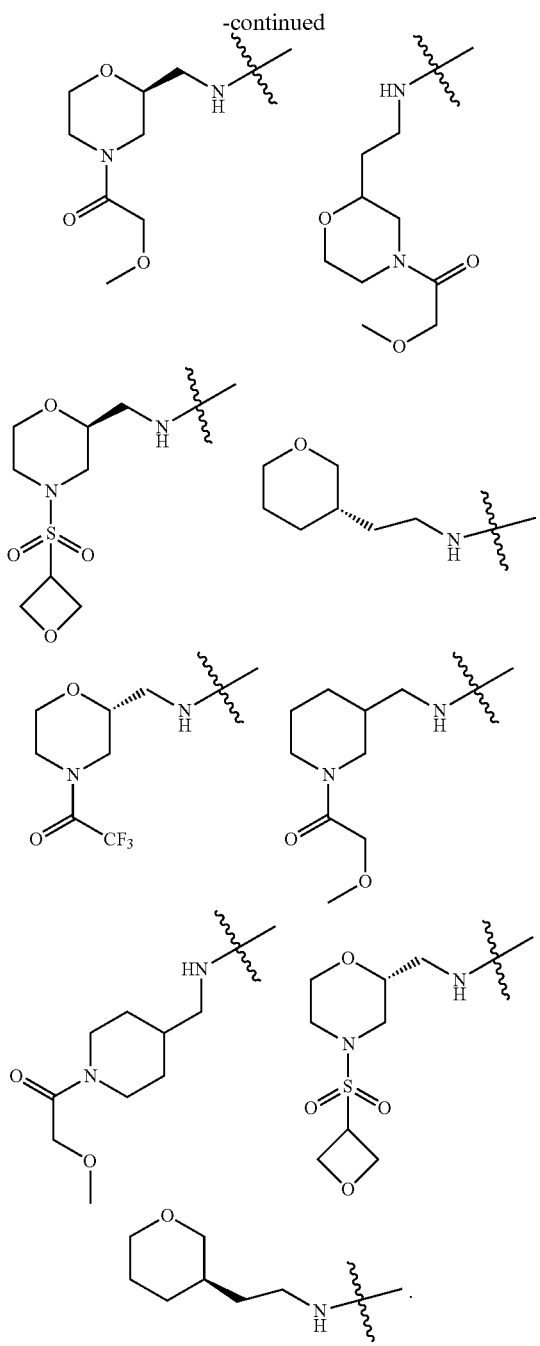

In another aspect, the present application relates to a pharmaceutical composition comprising the compound of formula I or II, or the stereoisomer thereof or the pharmaceutically acceptable salt thereof disclosed herein. In some embodiments, the pharmaceutical composition disclosed herein further comprises a pharmaceutically acceptable excipient.

In another aspect, the present application describes a method for treating an anti-apoptotic protein BCL-2-related disease in a mammal, comprising administering to a mammal, preferably a human, in need of such treatment a therapeutically effective amount of the compound of formula I or II, or the stereoisomer thereof or the pharmaceutically acceptable salt thereof, or the pharmaceutical composition thereof.

In another aspect, the present application describes use of the compound of formula I or II, or the stereoisomer thereof or the pharmaceutically acceptable salt thereof, or the pharmaceutical composition thereof disclosed herein in preparing a medicament for preventing or treating an anti-apoptotic protein BCL-2-related disease.

In another aspect, the present application describes use of the compound of formula I or II, or the stereoisomer thereof or the pharmaceutically acceptable salt thereof, or the pharmaceutical composition thereof disclosed herein in preventing or treating an anti-apoptotic protein BCL-2-related disease.

In another aspect, the present application describes the compound of formula I or II, or the stereoisomer thereof or the pharmaceutically acceptable salt thereof, or the pharmaceutical composition thereof disclosed herein for use in preventing or treating an anti-apoptotic protein BCL-2-related disease.

The anti-apoptotic protein BCL-2-related disease is selected from cancer. The cancer is selected from acute lymphocytic leukemia.

The compound disclosed herein has a good inhibitory effect on the proliferation of RS4;11 cells, good selectivity and a significant inhibitory effect on the tumor growth of RS4;11 human acute lymphoblastic leukemia mouse transplanted tumor models, and it is well tolerated by the tumor-bearing mice.

Definitions

Unless otherwise stated, the following terms used in the present invention shall have the following meanings. A certain term, unless otherwise specifically defined, should not be considered uncertain or unclear, but construed according to its common meaning in the field. When referring to a trade name, it is intended to refer to its corresponding commercial product or its active ingredient.

The term "substituted" means that any one or more hydrogen atoms on a specific atom are substituted by substituents, as long as the valence of the specific atom is normal and the resulting compound is stable. When the substituent is oxo (namely =O), it means that two hydrogen atoms are substituted, and oxo is not available on an aromatic group.

The term "optional" or "optionally" means that the subsequently described event or circumstance may, but not necessarily, occur. The description includes instances where the event or circumstance occurs and instances where the event or circumstance does not occur. For example, an ethyl being "optionally" substituted with halogen means that the ethyl may be unsubstituted (—CH$_2$CH$_3$), monosubstituted (for example, —CH$_2$CH$_2$F), polysubstituted (for example, —CHFCH$_2$F, —CH$_2$CHF$_2$ and the like) or fully substituted (—CF$_2$CF$_3$ or —C$_2$F$_5$). It will be understood by those skilled in the art that for any groups comprising one or more substituents, any substitutions or substituting patterns which may not exist or cannot be synthesized spatially are not introduced.

$C_{m-n}$ used herein means that the portion has an integer number of carbon atoms in the given range. For example, "$C_{1-6}$" means that the group may have 1 carbon atom, 2 carbon atoms, 3 carbon atoms, 4 carbon atoms, 5 carbon atoms or 6 carbon atoms.

The term "halo-" or "halogen" refers to fluorine, chlorine, bromine and iodine.

The term "alkyl" refers to hydrocarbyl with a general formula of $C_nH_{2n+1}$. The alkyl can be linear or branched. For example, the term "$C_{1-6}$ alkyl" refers to alkyl with 1-6 carbon atoms (for example, methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, etc.). The alkyl moieties (namely alkyl) of alkoxy, alkylamino, dialkylamino, alkylsulfonyl and alkylthio are similarly defined as above. For another example, the term "$C_{1-4}$ alkyl" refers to alkyl containing 1-4 carbon atoms (for example, methyl, ethyl, n-propyl, isopropyl, n-butyl, isobutyl, sec-butyl, tert-butyl).

The term "alkylene" refers to a divalent group formed by the removal of 1 hydrogen at any position of alkyl. For example, non-limiting examples of the term "$C_{0-6}$ alkylene" or "$C_{1-6}$ alkylene" include, but are not limited to, methylene, ethylidene, methylmethylene, dimethylmethylene, 1,3-propylidene and the like. Co represents a bond.

The term "cycloalkyl" refers to a carbon ring that is fully saturated and may exist as a monocyclic, bridged cyclic or spiro structure. Unless otherwise specified, the carbon ring is generally a 3-10 membered ring. Non-limiting examples of cycloalkyl include, but are not limited to, cyclopropyl, cyclobutyl, cyclopentyl, cyclohexyl, norbornyl(bicyclo[2.2.1]heptyl), bicyclo[2.2.2]octyl, adamantyl and the like.

The term "heterocycloalkyl" refers to a cyclic group that is fully saturated and may exist as a monocyclic, fused polycyclic, bridged cyclic or spiro structure. Unless otherwise specified, the heterocyclyl is usually a 3-7 membered ring containing 1-3 heteroatoms (preferably 1 or 2 heteroatoms) independently selected from the group consisting of sulfur, oxygen and/or nitrogen. Examples of 3 membered heterocycloalkyl include, but are not limited to, oxiranyl, thiiranyl, and aziranyl; non-limiting examples of 4 membered heterocycloalkyl include, but are not limited to, azetidinyl, oxetanyl, and thietanyl; examples of 5 membered heterocycloalkyl include, but are not limited to, tetrahydrofuranyl, tetrahydrothienyl, pyrrolidinyl, isoxazolidinyl, oxazolidinyl, isothiazolidinyl, thiazolidinyl, imidazolidinyl, and tetrahydropyrazolyl; examples of 6 membered heterocycloalkyl include, but are not limited to, piperidinyl, tetrahydropyranyl, tetrahydrothiopyranyl, morpholinyl, piperazinyl, 1,4-oxathianyl, 1,4-dioxanyl, thiomorpholinyl, 1,3-dithianyl, and 1,4-dithianyl; examples of 7 membered heterocycloalkyl include, but are not limited to, azacycloheptanyl, oxacycloheptanyl and thiocycloheptanyl. Preferably, the heterocycloalkyl is a monocyclic heterocycloalkyl having 5 or 6 ring atoms.

The term "treating" means administering the compound or formulation disclosed herein to prevent, ameliorate or eliminate a disease or one or more symptoms associated with the disease, and includes:
 (i) preventing the occurrence of a disease or disease state in a mammal, particularly when such a mammal is predisposed to the disease state but has not yet been diagnosed as having it;
 (ii) inhibiting a disease or disease state, i.e., arresting its development; and
 (iii) alleviating a disease or disease state, i.e., causing its regression.

The term "therapeutically effective amount" refers to an amount of the compound disclosed herein for (i) treating or preventing a specific disease, condition or disorder; (ii) alleviating, ameliorating or eliminating one or more symptoms of a specific disease, condition or disorder, or (iii) preventing or delaying onset of one or more symptoms of a specific disease, condition or disorder described herein. The amount of the compound disclosed herein composing the "therapeutically effective amount" varies dependently on the compound, the disease state and its severity, the mode of administration, and the age of the mammal to be treated, but can be determined routinely by those skilled in the art in accordance with their knowledge and the present disclosure.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

A pharmaceutically acceptable salt, for example, may be a metal salt, an ammonium salt, a salt formed with an organic base, a salt formed with an inorganic acid, a salt formed with an organic acid, a salt formed with a basic or acidic amino acid, and the like.

The term "pharmaceutical composition" refers to a mixture consisting of one or more of the compounds or pharmaceutically acceptable salts thereof disclosed herein and a pharmaceutically acceptable excipient. The pharmaceutical composition is intended to facilitate the administration of the compound to an organic entity.

The term "pharmaceutically acceptable excipients" refers to those which do not have a significant irritating effect on an organic entity and do not impair the biological activity and properties of the active compound. Suitable excipients are well known to those skilled in the art, for example carbohydrate, wax, water-soluble and/or water-swellable polymers, hydrophilic or hydrophobic material, gelatin, oil, solvent, or water.

The word "comprise" and variations thereof such as "comprises" or "comprising" will be understood in an open, non-exclusive sense, i.e., "including but not limited to".

The compounds and intermediates disclosed herein may also exist in different tautomeric forms, and all such forms are included within the scope of the present application. The term "tautomer" or "tautomeric form" refers to structural isomers of different energies that can interconvert via a low energy barrier. For example, a proton tautomer (also referred to as prototropic tautomer) includes interconversion via proton transfer, such as keto-enol isomerism and imine-enamine isomerism. A specific example of a proton tautomer is an imidazole moiety where a proton can transfer between two ring nitrogens. A valence tautomer includes the interconversion via recombination of some bonding electrons.

The present application also comprises isotopically labeled compounds which are identical to those recited herein but have one or more atoms replaced by an atom having an atomic mass or mass number different from the atomic mass or mass number usually found in nature. Examples of isotopes that can be incorporated into the compounds disclosed herein include isotopes of hydrogen, carbon, nitrogen, oxygen, phosphorus, sulfur, fluorine, iodine, and chlorine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$.

Certain isotopically labeled compounds disclosed herein (e.g., those labeled with $^3H$ and $^{14}C$) can be used to analyze compounds and/or substrate tissue distribution. Tritium (i.e., $^3H$) and carbon-14 (i.e., $^{14}C$) isotopes are particularly preferred for their ease of preparation and detectability. Positron emitting isotopes, such as $^{15}O$, $^{13}N$, $^{11}C$, and $^{18}F$ can be used in positron emission tomography (PET) studies to determine substrate occupancy. Isotopically labeled compounds disclosed herein can generally be prepared by following procedures analogous to those disclosed in the schemes and/or examples below while substituting a non-isotopically labeled reagent with an isotopically-labeled reagent.

Furthermore, substitution with heavier isotopes such as deuterium (i.e., $^2$H) may provide certain therapeutic advantages (e.g., increased in vivo half-life or reduced dosage) resulting from greater metabolic stability and hence may be preferred in some circumstances in which deuterium substitution may be partial or complete, wherein partial deuterium substitution refers to substitution of at least one hydrogen with at least one deuterium.

The compound disclosed herein can be asymmetrical, for example, has one or more stereoisomers. Unless otherwise stated, all stereoisomers are included, for example, enantiomers and diastereoisomers. The compound with assymetric carbon atoms disclosed herein can be separated in an optically pure form or in a racemic form. The optically pure form can be separated from a racemic mixture or can be synthesized using a chiral raw material or a chiral reagent.

The pharmaceutical composition disclosed herein can be prepared by combining the compound disclosed herein with a suitable pharmaceutically acceptable excipient, and can be formulated, for example, into a solid, semisolid, liquid, or gaseous formulation such as tablet, pill, capsule, powder, granule, ointment, emulsion, suspension, suppository, injection, inhalant, gel, microsphere, and aerosol.

Typical routes of administration of the compound or the pharmaceutically acceptable salt thereof or the pharmaceutical composition thereof disclosed herein include, but are not limited to, oral, rectal, local, inhalation, parenteral, sublingual, intravaginal, intranasal, intraocular, intraperitoneal, intramuscular, subcutaneous, and intravenous administration.

The pharmaceutical composition disclosed herein can be manufactured by methods well known in the art, such as conventional mixing, dissolving, granulating, dragee-making, levigating, emulsifying, and lyophilizing.

In some embodiments, the pharmaceutical composition is in an oral form. For oral administration, the pharmaceutical composition can be formulated by mixing the active compounds with pharmaceutically acceptable excipients well known in the art. These excipients enable the compounds disclosed herein to be formulated into tablets, pills, pastilles, dragees, capsules, liquids, gels, slurries, suspensions and the like for oral administration to a patient.

A solid oral composition can be prepared by conventional mixing, filling or tableting. For example, it can be obtained by the following method: mixing the active compounds with solid excipients, optionally grinding the resulting mixture, adding additional suitable excipients if desired, and processing the mixture into granules to get the core parts of tablets or dragees. Suitable excipients include, but are not limited to: binders, diluents, disintegrants, lubricants, glidants, sweeteners or flavoring agents and the like.

The pharmaceutical compositions may also be suitable for parenteral administration, such as sterile solutions, suspensions or lyophilized products in suitable unit dosage forms.

In all of the administration methods of the compound of formula I or II described herein, the daily dosage administered is from 0.01 to 200 mg/kg body weight, given in individual or separated dosages.

The compounds disclosed herein can be prepared by a variety of synthetic methods well known to those skilled in the art, including the specific embodiments listed below, embodiments formed by combinations thereof with other chemical synthetic methods, and equivalents thereof known to those skilled in the art. The preferred embodiments include, but are not limited to, the examples disclosed herein. The chemical reactions of the embodiments disclosed herein are carried out in a proper solvent that must be suitable for the chemical changes in the present application and the reagents and materials required. In order to acquire the compounds disclosed herein, it is sometimes necessary for those skilled in the art to modify or select a synthesis procedure or a reaction scheme based on the existing embodiments.

An important consideration in synthesis route planning in the art is the selection of suitable protecting groups for reactive functional groups (e.g., hydroxyl in the present application). For example, reference may be made to Greene's Protective Groups in Organic Synthesis (4th Ed.) Hoboken, New Jersey: John Wiley & Sons, Inc.

In some embodiments, the compound of formula I or II disclosed herein can be prepared by those skilled in the art of organic synthesis through the following routes: Route 1:

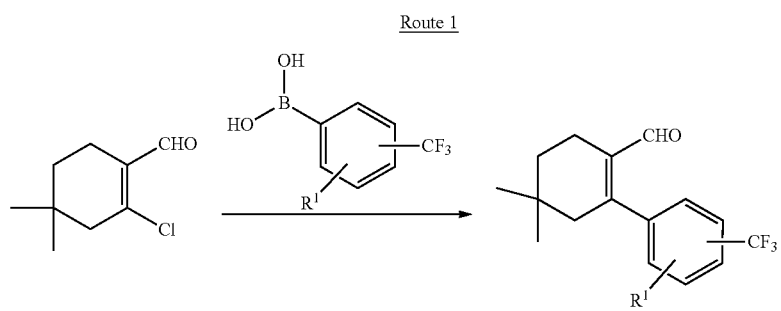

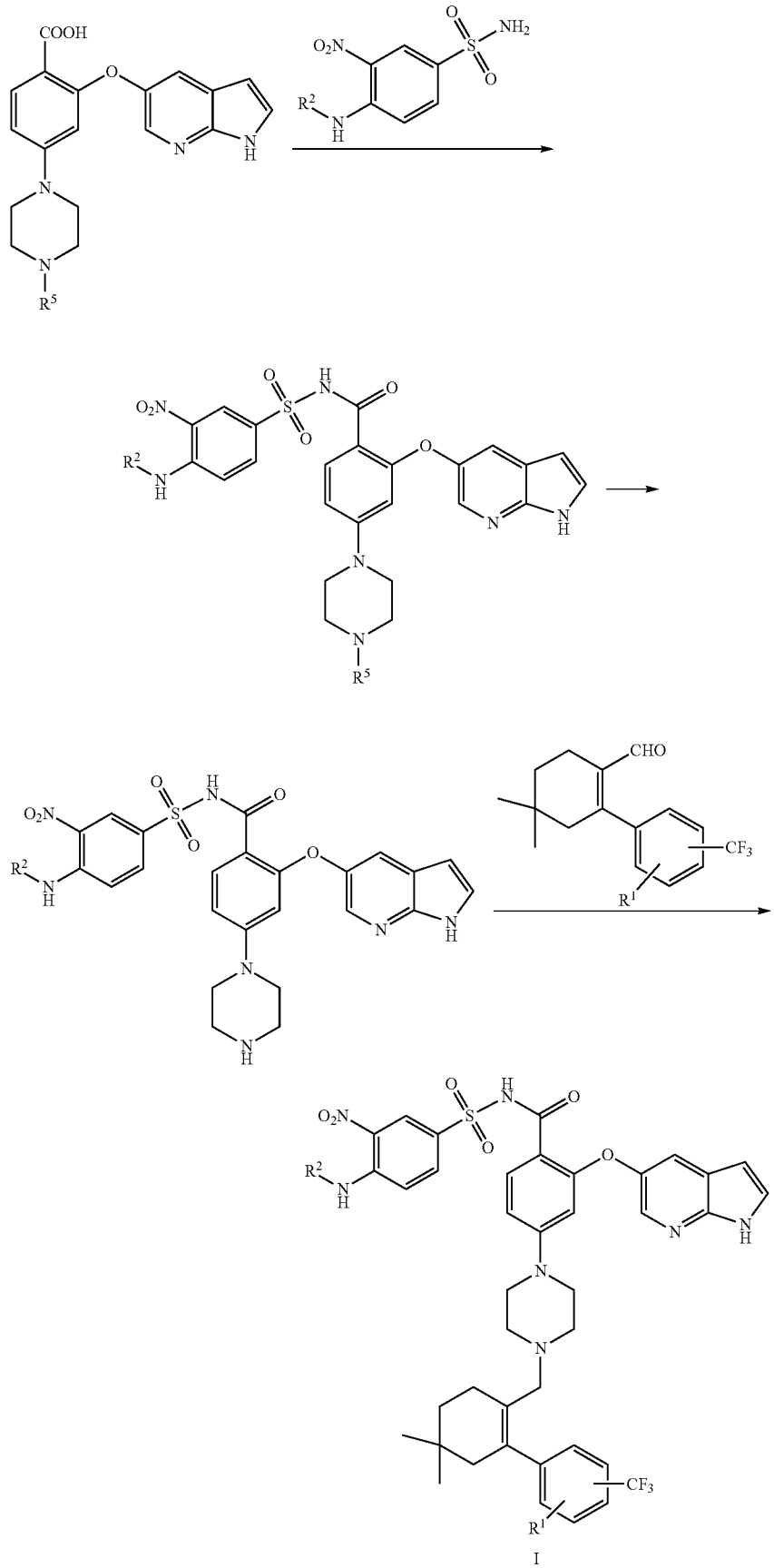

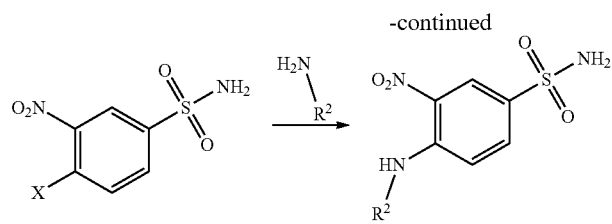

In the above scheme, $R^1$, $R^2$ or

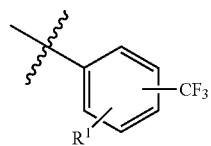

are as defined above, and X is selected from the group consisting of leaving groups, preferably from the group consisting of fluorine, chlorine, bromine and iodine; $R^5$ is selected from the group consisting of amino protecting groups, preferably Boc or benzyloxycarbonyl (Cbz).

DETAILED DESCRIPTION

Abbreviations: DMF represents N,N-dimethylformamide; Boc represents tert-butyloxycarbonyl; NaOAc represents sodium acetate; tBu represents tert-butyl; TBS represents tert-butyldimethylsilyl.

For clarity, the present application is further described with the following examples, which are, however, not intended to limit the scope of the invention. All reagents are commercially available and can be used without further purification.

Example 1: 4-(4-{[2-(2-methyl-4-trifluoromethylphenyl)-4,4-dimethylcyclohex-1-enyl]methyl}-piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)-benzamide

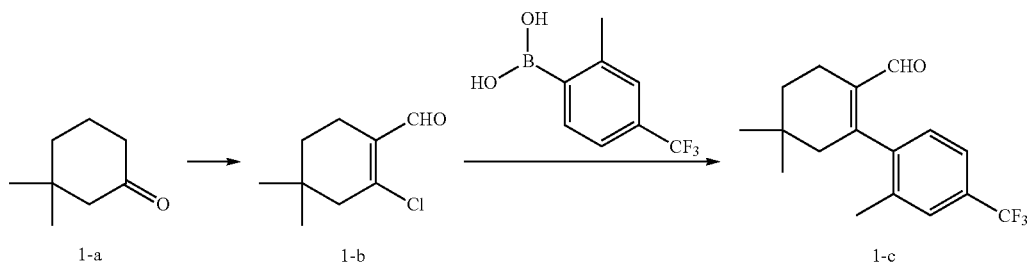

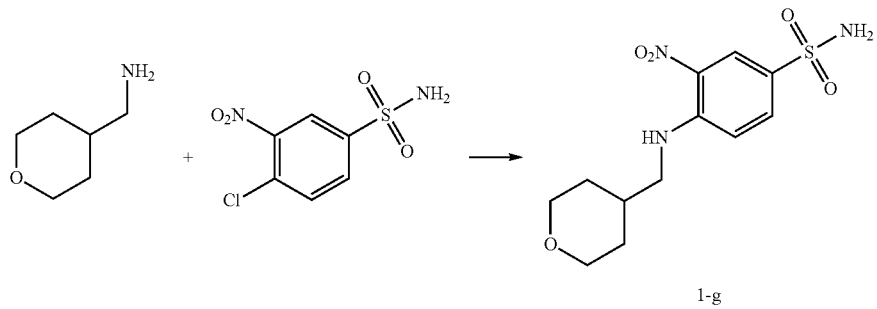

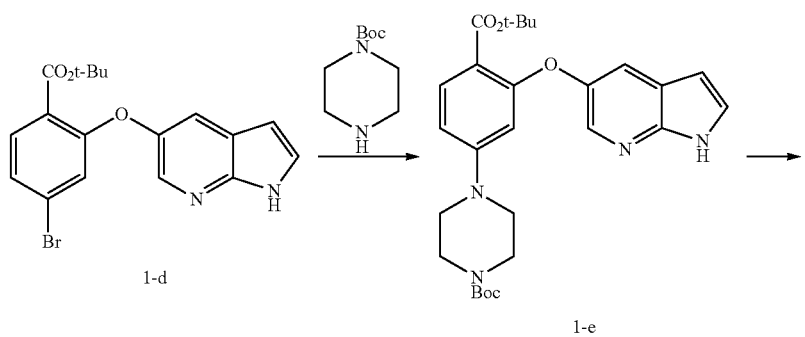

-continued
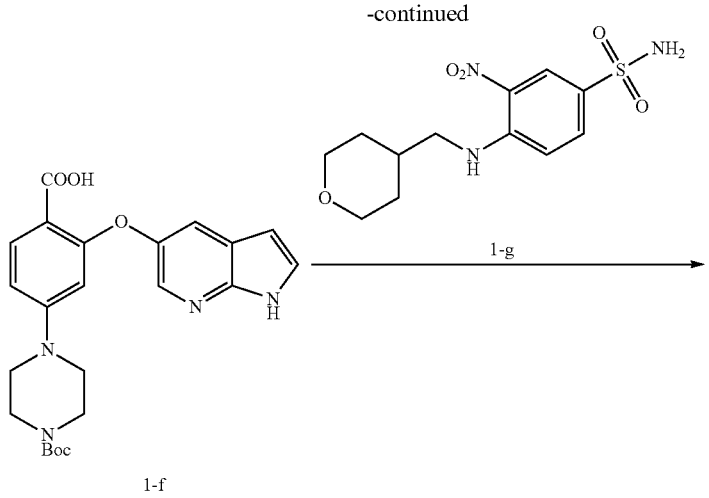
1-f
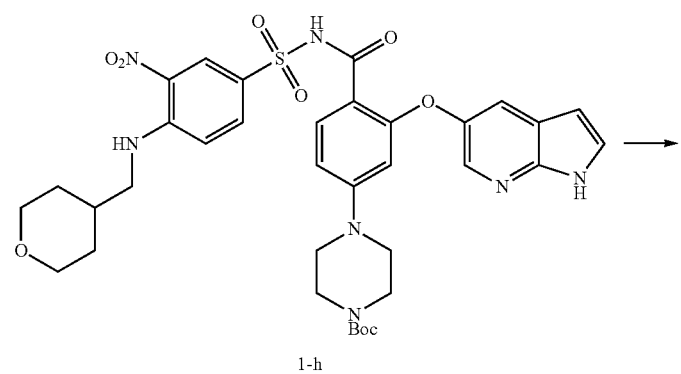
1-h
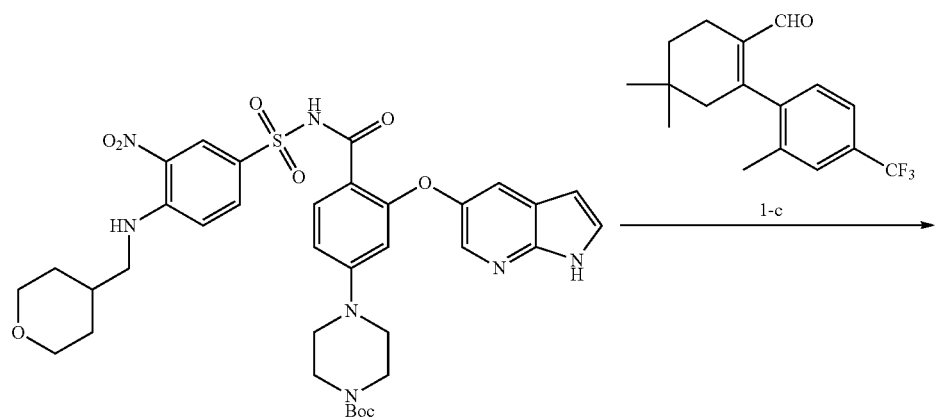
1-i

-continued

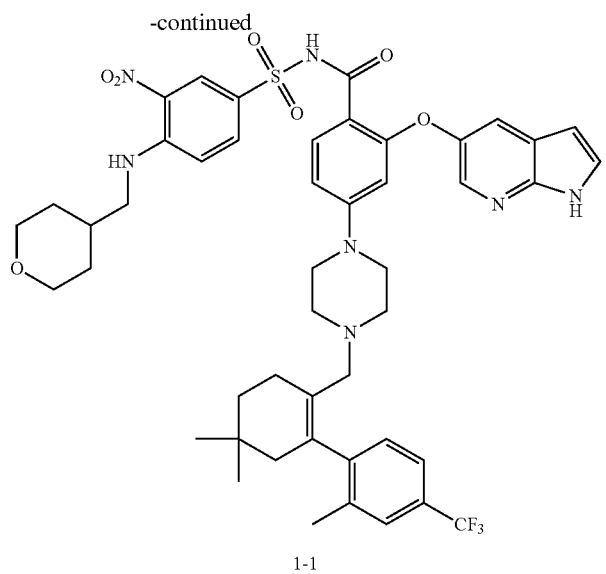

1-1

1) Preparation of Compound 1-b

To a solution of DMF (173.7 g) in dichloromethane (460 mL) was added phosphorus oxychloride (200 mL) dropwise at 0° C. After the addition, the mixture was heated to 20° C., stirred for 1 h and then cooled to 0° C. 3,3-dimethylcyclohexanone (1-a) (200 g) was added dropwise. After the addition, the mixture was heated to reflux overnight. The reaction solution was added to a solution containing NaOAc (86.7 g), NaCl (80 g), water (1.2 L) and dichloromethane (600 mL) dropwise while stirring. The resulting mixture was stirred at room temperature for 20 min and separated. The aqueous phase was extracted with dichloromethane (500 mL). The organic phases were combined, washed once with a solution of $K_3PO_4$ (40 g) and NaCl (90 g) in water (1 L), dried over anhydrous sodium sulfate, filtered and concentrated to give compound 1-b (249 g).

2) Preparation of Compound 1-c

Compound 1-b (1.69 g), 1,1'-bis(diphenylphosphino)ferrocenepalladium dichloride (0.4 g), $K_3PO_4$ (8.30 g) and ethylene glycol dimethyl ether (30 mL) were mixed and the mixture was stirred for 10 min. Then 2-methyl-4-trifluoromethylphenylboronic acid (2.0 g) was added, and the mixture was reacted at 85° C. for 8 h under $N_2$ atmosphere until the reaction was completed. To the reaction solution was added a solution of 5 wt % $NaHCO_3$ and 2 wt % L-cysteine in water (15 mL) and ethyl acetate (25 mL), the resulting mixture was stirred for 0.5 h and filtered, and separated. The aqueous phase was extracted with ethyl acetate (60 mL×2). The organic phases were combined, washed with saturated aqueous NaCl solution, dried over anhydrous $Na_2SO_4$, filtered, concentrated, and subjected to column chromatography to give compound 1-c (2.3 g).

3) Preparation of Compound 1-e

Tert-butyl 2-[(1H-pyrrolo[2,3-b]pyridin-5-yl)oxy]-4-bromobenzoate (compound 1-d) (77.8 g), Boc-piperazine (55.8 g), tris(dibenzylideneacetone)dipalladium (9 g), [(4-(N,N-dimethylamino)phenyl]di-tert-butylphosphine (5.2 g), sodium tert-butoxide (96.1 g), toluene (800 mL) and tetrahydrofuran (300 mL) were mixed, and the mixture was stirred, heated to 60° C. and reacted for 24 h under nitrogen atmosphere. The reaction solution was washed with a solution of L-cysteine (100 g) and $NaHCO_3$ (150 g) in water (1.5 L, 750 mL×2), and then washed with saturated NaCl solution, dried over anhydrous $Na_2SO_4$, filtered and concentrated to give compound 1-e (40 g). ESI-MS: m/z=495.4 $[M+H]^+$.

4) Preparation of Compound 1-f

Compound 1-e (40 g), tetrahydrofuran (800 mL), ethanol (270 mL) and water (15 mL) were mixed, and the mixture was stirred. Then KOH (45.3 g) was added, and the mixture was heated to 80° C. and stirred under reflux for 8 h until the reaction was completed. Water (500 mL) was added, and the resulting mixture was stirred, adjusted to pH 5-6 with diluted hydrochloric acid, filtered, slurried with water (1 L, 500 mL×2) and dried to give compound 1-f (35 g).

5) Preparation of Compounds 1-g

3-Nitro-4-chlorobenzenesulfonamide (100 g), 4-aminomethyl tetrahydropyran (58 g) and N,N-diisopropylethylamine (135 g) were dissolved in acetonitrile (1 L), and the solution was heated to 85° C. and reacted for 8 h. The reaction solution was cooled at room temperature, left standing overnight, and filtered to give compound 1-g (112 g).

6) Preparation of Compound 1-h

Compound 1-f (35 g) and dichloromethane (100 mL) were mixed and the mixture was stirred at room temperature. Then 4-dimethylaminopyridine (38.5 g) and 1-ethyl-(3-dimethylaminopropyl)carbodiimine hydrochloride (65.8 g) were added and dissolved with stirring. 3-Nitro-4-[[(tetrahydropyran-4-yl)methyl]amino]benzenesulfonamide (compound 1-g) (25.2 g) was added, and the resulting mixture was reacted at room temperature for 3 h. The reaction solution was washed successively with 5 wt % hydrochloric acid, saturated aqueous sodium bicarbonate solution and saturated aqueous sodium chloride solution, dried over anhydrous $Na_2SO_4$, filtered and concentrated. Then dichloromethane (200 mL) was added, and the resulting mixture was stirred at room temperature for 2 h, filtered and dried to give compound 1-h (40 g).

7) Preparation of Compound 1-i

Compound 1-h was added to isopropanol (500 mL), and the mixture was stirred. Then concentrated HCl (50 mL) was added, and the mixture was heated to 65° C. and stirred for 8 h until the reaction was completed. The reaction mixture was filtered, and the filter cake was dissolved in water (300 mL). Saturated sodium bicarbonate was added dropwise to adjust to pH 6-7, and the resulting mixture was filtered and dried. The resulting solid was slurried with ethyl acetate (200 mL), filtered and dried to give compound 1-i (27 g).

8) Preparation of Compound 1-1

Compound 1-c (2.0 g) and compound 1-i (4.9 g) were dissolved in methanol (20 mL), and the solution was stirred. Then sodium borohydride (5.72 g) was added, and the resulting mixture was stirred for 6 h until the reaction was completed. Saturated aqueous ammonium chloride solution (25 mL) was added to quench the reaction, and the resulting mixture was extracted with ethyl acetate (40 mL×2), washed with saturated aqueous sodium chloride solution, dried over anhydrous Na$_2$SO$_4$ and filtered. The filtrate was concentrated and subjected to column chromatography to give compound 1-1 (120 mg).

$^1$H NMR (500 MHz, DMSO-d$_6$) δ 11.80-11.58 (m, 2H), 8.67-8.55 (m, 2H), 8.05 (d, J=2.6 Hz, 1H), 7.83 (dd, J=9.3, 2.4 Hz, 1H), 7.59-7.48 (m, 5H), 7.16 (dd, J=24.3, 8.7 Hz, 2H), 6.74 (dd, J=9.0, 2.4 Hz, 1H), 6.40 (dd, J=3.3, 1.9 Hz, 1H), 6.28 (d, J=2.4 Hz, 1H), 3.86 (dd, J=11.2, 4.2 Hz, 2H), 3.62 (d, J=13.2 Hz, 1H), 3.38-3.19 (m, 7H), 2.34-2.25 (m, 1H), 2.23 (s, 1H), 2.17 (s, 4H), 2.08 (s, 1H), 1.90 (t, J=14.5 Hz, 4H), 1.62 (dd, J=13.1, 3.6 Hz, 2H), 1.56-1.40 (m, J=6.4 Hz, 3H), 1.33-1.20 (m, 3H), 0.97 (d, J=3.1 Hz, 6H).

$^{13}$C NMR (126 MHz, DMSO) δ 163.97, 158.95, 158.66, 158.21, 154.01, 147.90, 146.83, 145.91, 145.28, 140.86, 136.63, 135.62, 134.30, 132.57, 130.06, 129.46, 128.33, 127.26, 124.77, 123.25, 122.73, 120.32, 118.43, 115.56, 114.17, 109.71, 103.48, 100.44, 67.08, 58.52, 48.41, 45.88, 44.35, 44.30, 34.69, 34.32, 30.62, 29.05, 29.01, 27.49, 24.69, 19.09.

ESI-MS: m/z=916.4 [M+H]$^+$.

Example 2: (R)-4-(4-{[2-(2-methyl-4-trifluoromethylphenyl)-4,4-dimethylcyclohex-1-enyl]methyl}-piperazin-1-yl)-N-({3-nitro-4-[(1,4-dioxan-2-yl)methyl]amino]phenyl}sulfonyl)-2-(1H-pyrrolo[2,3-b]pyridin-5-yloxy)-benzamide

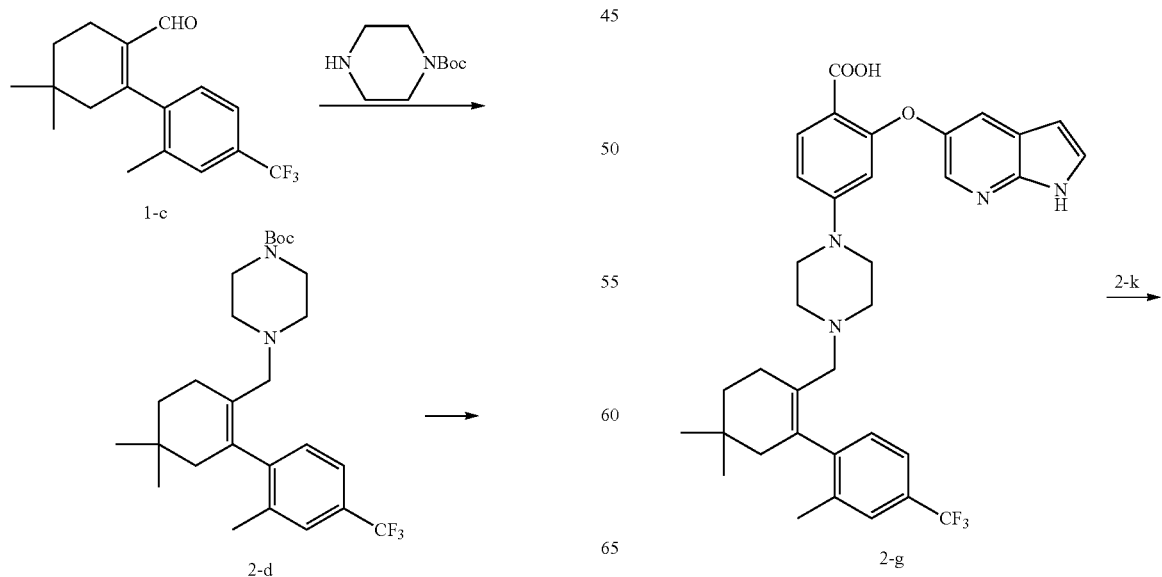

-continued

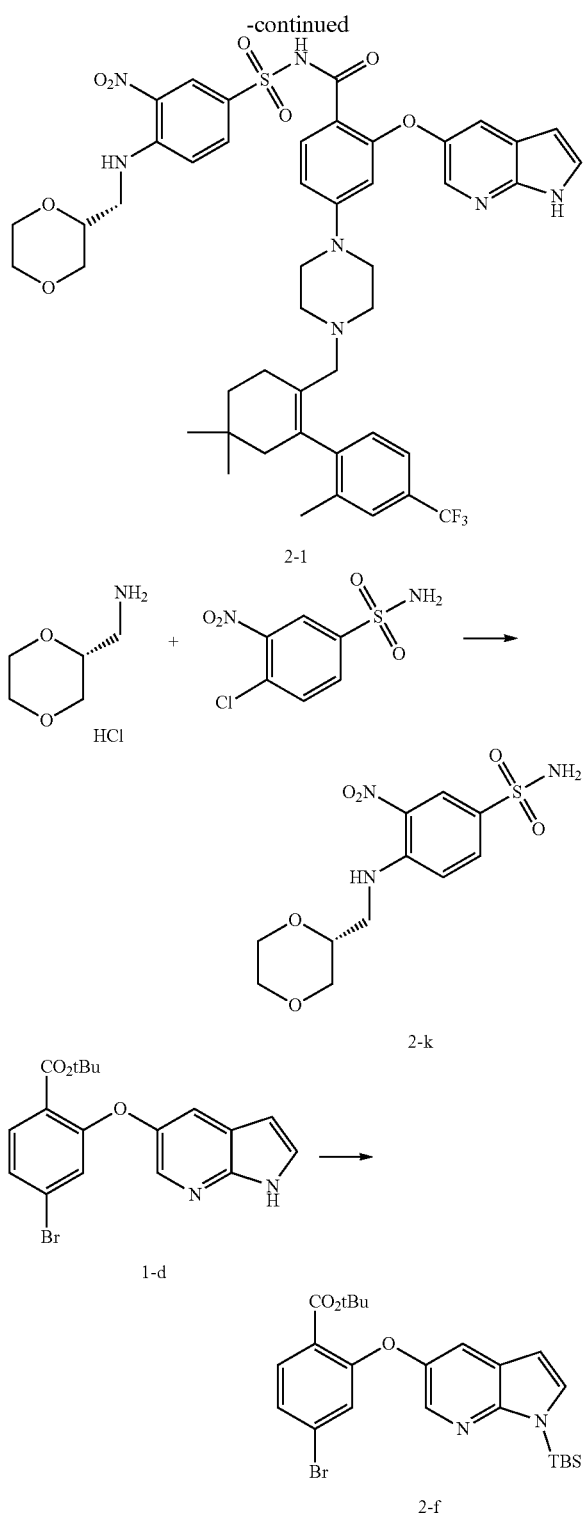

1) Preparation of Compound 2-d

Compound 1-c (103 g) and 1-Boc-piperazine (73.28 g) were dissolved in acetonitrile (1000 mL), and the solution was stirred and cooled to 0° C. Then sodium triacetoxyborohydride (227 g) was slowly added, and the resulting mixture was stirred at room temperature for 5 h. After the reaction was completed, water (1 L) was added and the resulting mixture was extracted with ethyl acetate (300 mL). The organic phase was collected, dried over anhydrous $Na_2SO_4$, filtered and concentrated to give compound 2-d (150 g).

2) Preparation of Compound 2-e

Compound 2-d (150 g), isopropanol (830 mL) and hydrochloric acid (36-38%, 125 mL) were mixed, and the mixture was heated to 65° C. and reacted for 3 h. The reaction solution was cooled to precipitate a solid, and the solid was collected by filtration and dried to give compound 2-e (80 g).

$^1$H NMR (500 MHz, DMSO-$d_6$) 11.70 (1H, brs), 7.64 (1H, s), 7.55 (1H, d, J=8.0 Hz), 7.27 (1H, d, J=8.0 Hz), 3.53-3.40 (8H, m), 3.14-3.03 (2H, m), 2.79-2.65 (2H, m), 2.20 (3H, s), 1.99 (1H, d, J=18.0 Hz), 1.88 (1H, d, J=18.0 Hz), 1.50 (2H, m), 0.99 (3H, s), 0.98 (3H, s) ESI-MS: m/z=367.4 [M+H]$^+$.

3) Preparation of Compound 2-g

NaH (21.1 g) was dissolved in THF (100 mL), and the solution was cooled to −20° C. and stirred for 10 min. Tert-butyl 2-[(1H-pyrrolo[2,3-b]pyridin-5-yl)oxy]-4-bromobenzoate (compound 1-d, 128.3 g) was dissolved in THF (200 mL), and the resulting solution was then slowly added dropwise to the reaction solution, with the internal temperature maintained below 0° C. After the addition, the mixture was stirred for 30 min. To the reaction solution was added dropwise a solution of TBSCl (64.7 g) in THF (200 mL), with the internal temperature maintained at about −10° C. After the addition, the resulting mixture was reacted for 30 min. After the reaction was completed, saturated sodium bicarbonate (500 mL) was added, and the resulting mixture was extracted with ethyl acetate. The organic phase was collected, dried over anhydrous $Na_2SO_4$, filtered, concentrated and purified by column chromatography to give compound 2-f (150 g). ESI-MS: m/z=503.1 [M+H]$^+$.

Compound 2-e (80 g), tert-butyl 2-[(1-tert-butyldimethylsilylpyrrolo[2,3-b]pyridin-5-yl)oxy]-4-bromobenzoate (compound 2-f, 109.7 g), tris(dibenzylideneacetone)dipalladium (2.7 g), [(4-(N,N-dimethylamino)phenyl]di-tert-butylphosphine (1.6 g), sodium tert-butoxide (187.4 g) and toluene (800 mL) were mixed, and the mixture was stirred, heated to 100° C. and reacted for 24 h under nitrogen atmosphere. After the reaction was completed, water (1 L) and ethyl acetate (300 mL) were added for extraction. The organic phase was collected, dried over anhydrous $Na_2SO_4$, filtered and concentrated to give compound 2-g (182.6 g).

ESI-MS: m/z=789.6 [M+H]$^+$.

4) Preparation of Compound 2-h

A mixture of compound 2-g (182.6 g), toluene (1.8 L) and trifluoroacetic acid (107 mL) was heated to 45° C. and reacted for 5 h. The reaction solution was concentrated, and ethyl acetate (1.5 L) was added. The resulting mixture was washed with saturated aqueous $NaHCO_3$ solution and saturated aqueous sodium chloride solution, dried over anhydrous sodium sulfate, filtered and concentrated. Toluene (1 L) and ethyl acetate (200 mL) were added, and the resulting mixture was heated until it was clarified and cooled to precipitate a solid. The solid was collected by filtration and dried to give compound 2-h (75.2 g).

$^1$H NMR (500 MHz, DMSO-$d_6$), δH: 12.2 (brs, 1H), 11.64 (s, 1H), 7.97 (d, J=2.45 Hz, 1H), 7.74 (d, J=9.0 Hz, 1H), 7.53 (s, 1H), 7.46 (m, 2H), 7.38 (d, J=2.2 Hz, 1H), 7.09 (d, J=8.0 Hz, 1H), 6.71 (dd, J=9.3, 1.9 Hz, 1H), 6.35 (m, 1H), 6.33 (d, J=1.5 Hz, 1H), 3.10 (brs, 4H), 2.24 (m, 3H), 2.16 (s, 3H), 2.08 (m, 2H), 1.83 (m, 2H), 1.42 (t, 2H), 0.94 (s, 6H), 0.83 (s, 3H).

ESI-MS: m/z=619.5 [M+H]$^+$.

5) Preparation of Compound 2-k

3-Nitro-4-chlorobenzenesulfonamide (0.64 g), (R)-(1,4-dioxan)-2-methylamine hydrochloride (0.5 g) and N,N-diisopropylethylamine (1.58 g) were dissolved in acetonitrile (10 mL), and the solution was heated to 85° C. and reacted for 6.5 h. The reaction solution was cooled at room temperature, left standing overnight, and filtered to give compound 2-k (0.65 g).

ESI-MS: m/z=316.2 [M−H]⁻.

6) Preparation of Compound 2-l

Compound 2-h (0.3 g) and dichloromethane (5 mL) were mixed, and the mixture was stirred at room temperature. Then 4-dimethylaminopyridine (0.05 g) and 1-ethyl-(3-dimethylaminopropyl)carbodiimine hydrochloride (0.07 g) were added and dissolved with stirring. Compound 2-k (0.15 g) and triethylamine (0.12 g) were added, and the resulting mixture was reacted at room temperature for 3 h. The reaction solution was washed successively with 5 wt % hydrochloric acid, saturated aqueous sodium bicarbonate solution and saturated aqueous sodium chloride solution, dried over anhydrous Na$_2$SO$_4$, filtered, concentrated, and purified by column chromatography to give compound 2-l (0.12 g).

¹HNMR (500 MHz, DMSO-d$_6$) δH: 11.73 (s, 2H), 8.61 (1H, brs), 8.57 (1H, brs), 8.05 (1H, s), 7.82 (1H, d, J=9.0), 7.59 (1H, s), 7.49-7.55 (4H, m), 7.17 (1H, d, J=8.0), 7.12 (1H, d, J=9.5), 6.73 (1H, d, J=9.0), 6.40 (1H, s), 6.28 (1H, s), 3.61-3.81 (8H, m), 3.19-3.51 (7H, m), 3.02 (3H, m), 2.61 (1H, m), 2.30 (1H, m), 2.16 (4H, s), 1.87-1.93 (2H, m), 1.49 (2H, s), 0.96 (6H, s).

ESI-MS: m/z=918.8 [M+H]⁺.

Example 3: (S)-4-(4-{[2-(2-methyl-4-trifluoromethylphenyl)-4,4-dimethylcyclohex-1-enyl]methyl}-piperazin-1-yl)-N-({3-nitro-4-[(1,4-dioxan-2-yl)methyl)amino]phenyl}sulfonyl)-2-(1H-pyrrolo[2,3-b]pyridin-5-yloxy)-benzamide

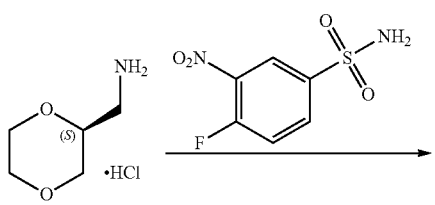

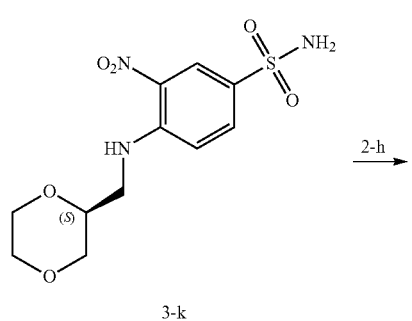

3-k

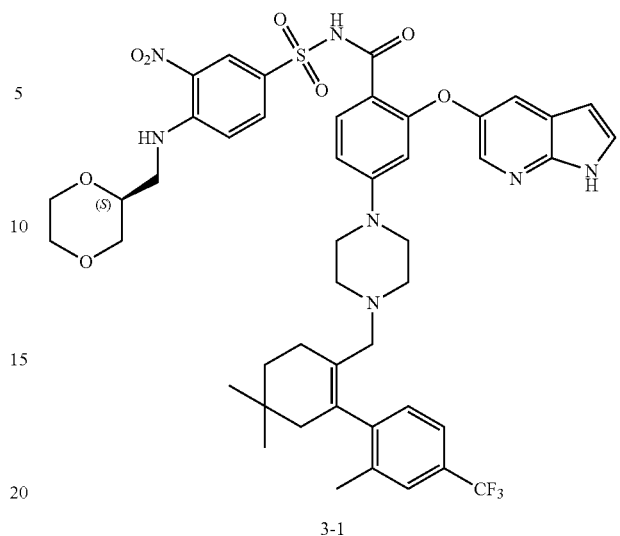

3-1

1) Preparation of Compound 3-k

Compound 3-k (4.70 g) was obtained by reference to the preparation method for compound 2-k in step 5) of Example 2, with (R)-(1,4-dioxane)-2-methylamine hydrochloride being replaced by (S)-2-(aminomethyl)-1,4-dioxane hydrochloride. ESI-MS: m/z=316.1 [M−H]⁻.

2) Preparation of Compound 3-l

Compound 3-l was obtained by reference to the preparation method for compound 2-l in step 6) of Example 2, with compound 2-k being replaced by compound 3-k.

¹H NMR (500 MHz, DMSO-d$_6$), δH: 11.72 (s, 1H), 11.68 (m, 1H), 8.60 (t, J=5.4 Hz, 1H), 8.57 (d, J=2.3 Hz, 1H), 8.04 (d, J=2.6 Hz, 1H), 7.83 (dd, J=9.2, 2.0 Hz, 1H), 7.58 (brs, 1H), 7.54 (d, J=2.5 Hz, 1H), 7.51 (m, 3H), 7.17 (d, J=8.0 Hz, 1H), 7.11 (d, J=9.4 Hz, 1H), 6.73 (dd, J=9.0, 2.0 Hz, 1H), 6.40 (m, 1H), 6.27 (d, J=1.9 Hz, 1H), 3.79 (m, 4H), 3.64 (m, 4H), 3.49 (m, 2H), 3.41 (m, 1H), 3.29 (m, 4H), 3.02 (brs, 2H), 2.91 (brs, 1H), 2.64 (m, 1H), 2.29 (m, 1H), 2.18 (m, 1H), 2.16 (s, 3H), 1.91 (m, 2H), 1.49 (m, 2H), 0.97 (s, 3H), 0.96 (s, 3H).

ESI-MS: m/z=918.8 [M+H]⁺.

Example 4: 4-(4-{[2-(2-methyl-4-trifluoromethylphenyl)-4,4-dimethylcyclohex-1-enyl]methyl}-piperazin-1-yl)-N-({3-nitro-4-[(S)-(4-methoxyacetylmorpholin-2-yl)methyl)amino]phenyl}sulfonyl)-2-(1H-pyrrolo[2,3-b]pyridin-5-yloxy)-benzamide

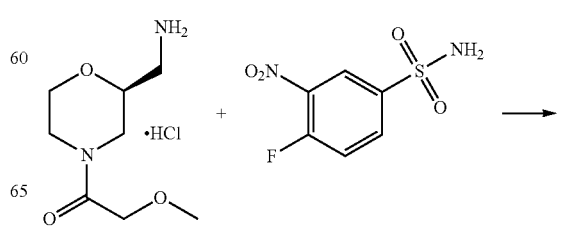

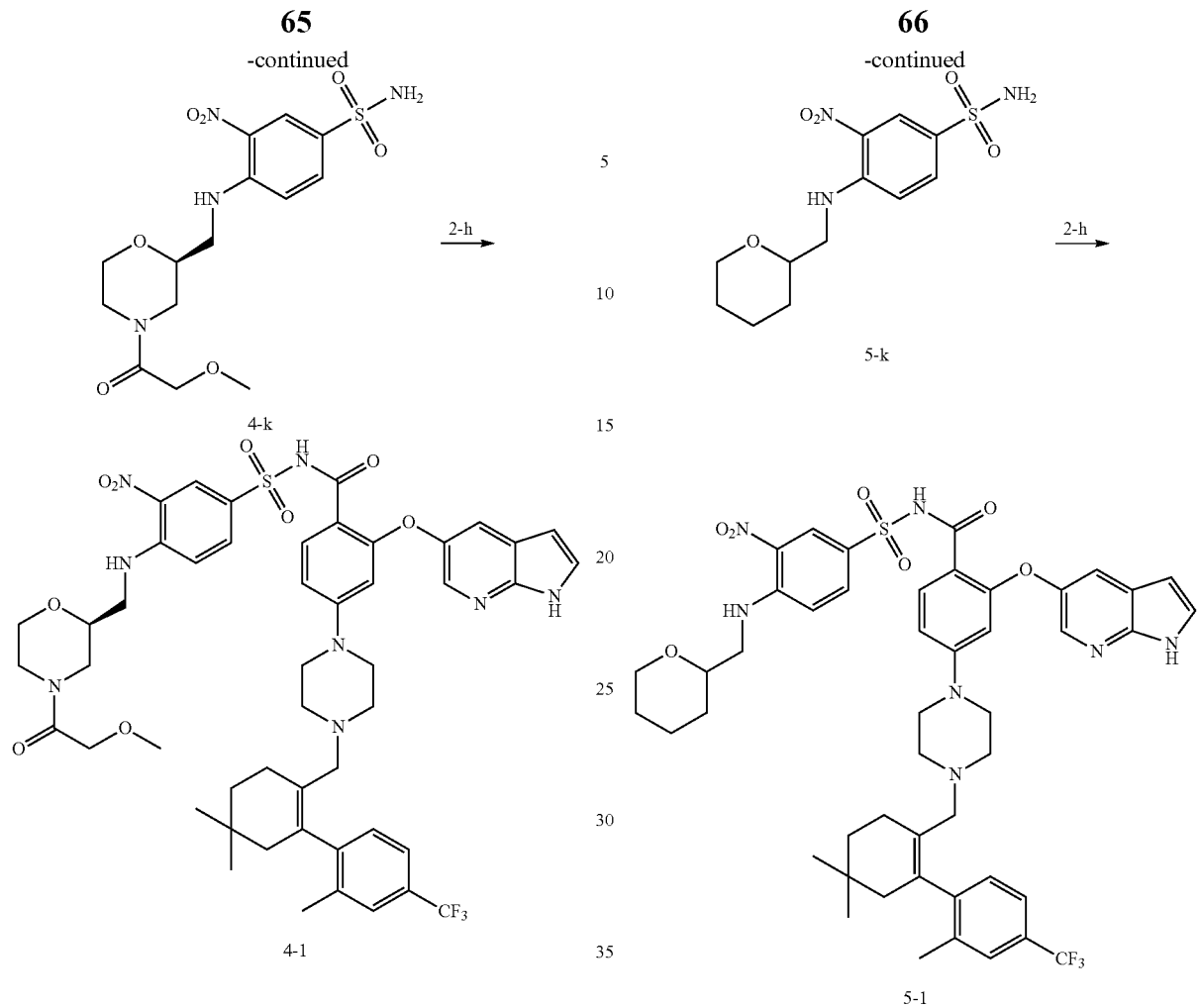

1) Preparation of Compound 4-k

Compound 4-k (0.39 g) was obtained by reference to the preparation method for compound 2-k in step 5) of Example 2, with (R)-(1,4-dioxane)-2-methylamine hydrochloride being replaced by (S)-2-(aminomethyl)-4-methoxy-acetylmorpholine hydrochloride. ESI-MS: m/z=387.1 [M−H]⁻.

2) Preparation of Compound 4-l

Compound 4-l was obtained by reference to the preparation method for compound 2-l in step 6) of Example 2, with compound 2-k being replaced by compound 4-k.

ESI-MS: m/z=989.7 [M+H]⁺.

Example 5: 4-(4-{[2-(2-methyl-4-trifluoromethylphenyl)-4,4-dimethylcyclohex-1-enyl]methyl}-piperazin-1-yl)-N-({3-nitro-4-[(tetrahydro-2H-pyran-2-ylmethyl)amino]phenyl}sulfonyl)-2-(1H-pyrrolo[2,3-b]pyridin-5-yloxy)-benzamide

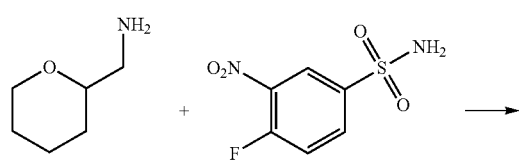

1) Preparation of Compound 5-k

Compound 5-k (1.92 g) was obtained by reference to the preparation method for compound 2-k in step 5) of Example 2, with (R)-(1,4-dioxane)-2-methylamine hydrochloride being replaced by 2-aminomethyltetrahydropyran. ESI-MS: m/z=316.0 [M+H]⁺.

2) Preparation of Compound 5-l

Compound 5-l was obtained by reference to the preparation method for compound 2-l in step 6) of Example 2, with compound 2-k being replaced by compound 5-k.

¹H NMR (500 MHz, DMSO-d₆), δH: 11.74 (s, 2H), 8.64 (t, J=5.1 Hz, 1H), 8.56 (d, J=2.0 Hz, 1H), 8.04 (d, J=2.5 Hz, 1H), 7.81 (dd, J=9.2, 1.6 Hz, 1H), 7.59 (s, 1H), 7.55 (d, J=2.2 Hz, 1H), 7.51 (m, 3H), 7.17 (d, J=7.9 Hz, 1H), 7.11 (d, J=9.4 Hz, 1H), 6.73 (d, J=8.8 Hz, 1H), 6.40 (m, 1H), 6.27 (s, 1H), 3.92 (d, J=10.9 Hz, 1H), 3.75 (m, 1H), 3.67 (m, 1H), 3.58 (m, 2H), 3.48 (m, 1H), 3.32 (m, 5H), 3.01 (m, 2H), 2.90 (brs, 1H), 2.61 (m, 1H), 2.29 (m, 1H), 2.16 (s, 3H), 1.91 (m, 2H), 2.08 (s, 1H), 1.80 (m, 1H) 1.64 (d, J=12.4 Hz, 1H), 1.48 (m, 5H), 1.28 (m, 1H), 0.96 (s, 6H).

ESI-MS: m/z=916.7 [M+H]⁺.

Example 6: (S)-4-(4-{[2-(2-methyl-4-trifluoromethylphenyl)-4,4-dimethylcyclohex-1-enyl]methyl}-piperazin-1-yl)-N-({3-nitro-4-[(tetrahydrofuran-3-yl)amino]phenyl}sulfonyl)-2-(1H-pyrrolo[2,3-b]pyridin-5-yloxy)-benzamide Example 7: (R)-4-(4-{[2-(2-methyl-4-trifluoromethylphenyl)-4,4-dimethylcyclohex-1-enyl]methyl}-piperazin-1-yl)-N-({3-nitro-4-[(tetrahydrofuran-3-yl)amino]phenyl}sulfonyl)-2-(1H-pyrrolo[2,3-b]pyridin-5-yloxy)-benzamide

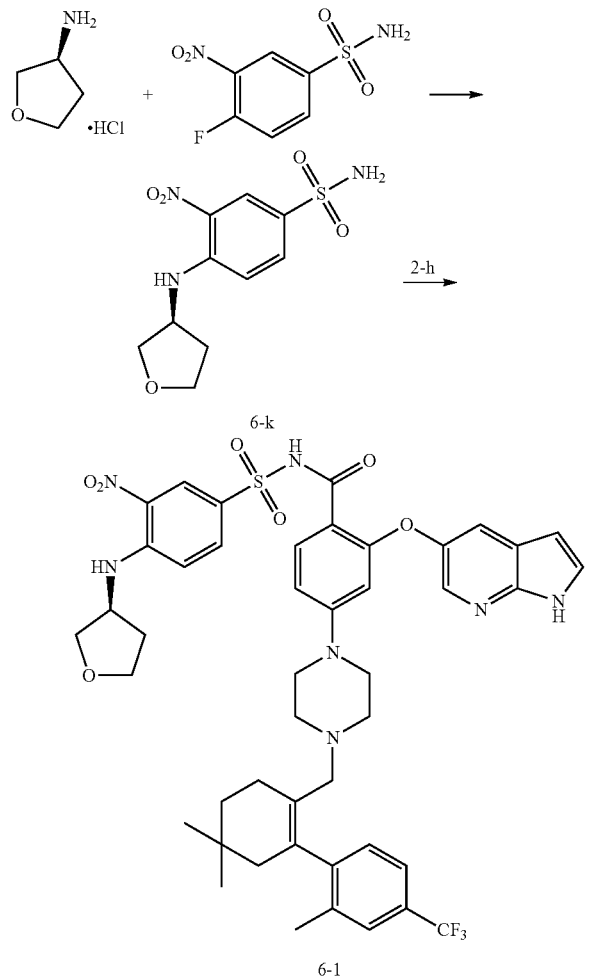

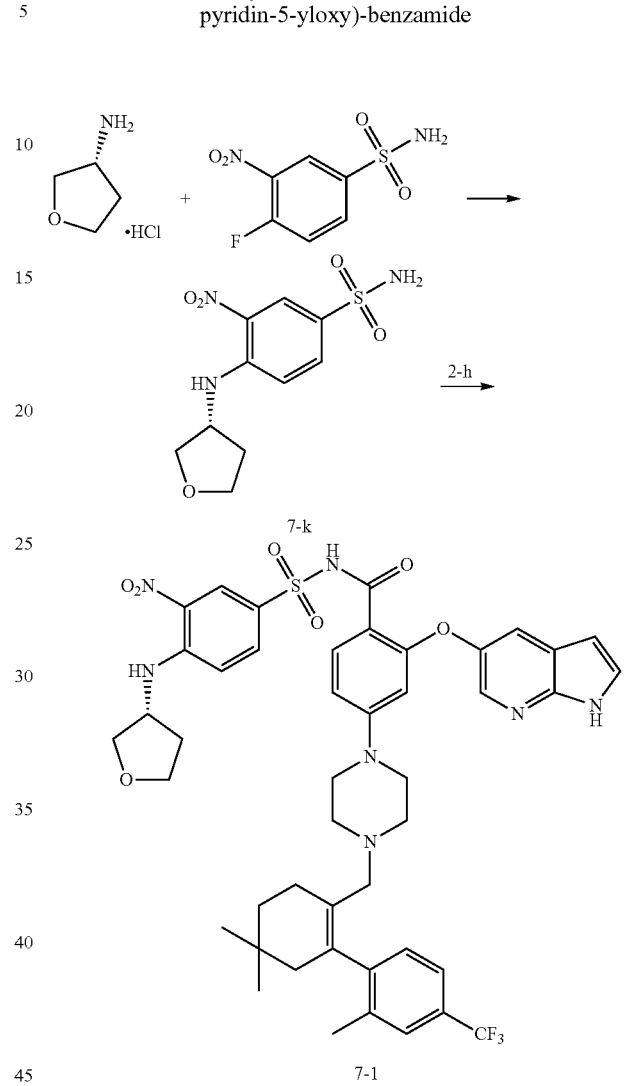

1) Preparation of Compound 6-k

Compound 6-k (1.72 g) was obtained by reference to the preparation method for compound 2-k in step 5) of Example 2, with (R)-(1,4-dioxane)-2-methylamine hydrochloride being replaced by (S)-3-aminotetrahydrofuran hydrochloride.

2) Preparation of Compound 6-1

Compound 6-1 was obtained by reference to the preparation method for compound 2-1 in step 6) of Example 2, with compound 2-k being replaced by compound 6-k.

$^1$H NMR (500 MHz, DMSO-$d_6$) δH: 11.79 (1H, s), 11.74 (1H, s), 8.56 (1H, brs), 8.32 (1H, d, J=6.0), 8.03 (1H, s), 7.85 (1H, d, J=9.0), 7.59 (1H, s), 7.50-7.53 (4H, m), 7.17 (1H, d, J=8.0), 7.12 (1H, d, J=9.0), 6.73 (1H, d, J=8.5), 6.39 (1H, s), 6.29 (1H, s), 3.86-3.94 (3H, m), 3.45-3.79 (5H, m), 3.24 (3H, m), 3.02 (3H, m), 2.61 (1H, m), 2.33 (2H, m), 2.16 (4H, s), 1.87-1.99 (3H, m), 1.35 (2H, s), 0.96 (6H, s).

ESI-MS: m/z=888.6 [M+H]$^+$.

1) Preparation of Compound 7-k

Compound 7-k (1.65 g) was obtained by reference to the preparation method for compound 2-k in step 5) of Example 2, with (R)-(1,4-dioxane)-2-methylamine hydrochloride being replaced by (R)-3-aminotetrahydrofuran hydrochloride.

2) Preparation of Compound 7-1

Compound 7-1 was obtained by reference to the preparation method for compound 2-1 in step 6) of Example 2, with compound 2-k being replaced by compound 7-k.

$^1$H NMR (500 MHz, DMSO-$d_6$) δH: 11.79 (1H, s), 11.74 (1H, s), 8.57 (1H, brs), 8.32 (1H, d, J=5.0), 8.03 (1H, s), 7.85 (1H, d, J=9.0), 7.59 (1H, s), 7.50-7.52 (4H, m), 7.17 (1H, d, J=7.0), 7.12 (1H, d, J=8.5), 6.74 (1H, d, J=8.5), 6.39 (1H, s), 6.29 (1H, s), 3.48-3.93 (8H, m), 3.24 (3H, m), 3.02 (3H, m), 2.61 (1H, m), 2.33 (2H, m), 2.16 (4H, s), 1.91-1.96 (3H, m), 1.50 (2H, s), 0.96 (6H, s).

ESI-MS: m/z=888.6 [M+H]$^+$.

Example 8: 4-(4-{[2-(2-methyl-4-trifluoromethylphenyl)-4,4-dimethylcyclohex-1-enyl]methyl}-piperazin-1-yl)-N-({3-nitro-4-[((tetrahydrofuran-3-yl)methyl)amino]phenyl}sulfonyl)-2-(1H-pyrrolo[2,3-b]pyridin-5-yloxy)-benzamide Example 9: (R)-4-(4-{[2-(2-methyl-4-trifluoromethylphenyl)-4,4-dimethylcyclohex-1-enyl]methyl}-piperazin-1-yl)-N-({3-nitro-4-[((tetrahydrofuran-3-yl)methyl)amino]phenyl}sulfonyl)-2-(1H-pyrrolo[2,3-b]pyridin-5-yloxy)-benzamide

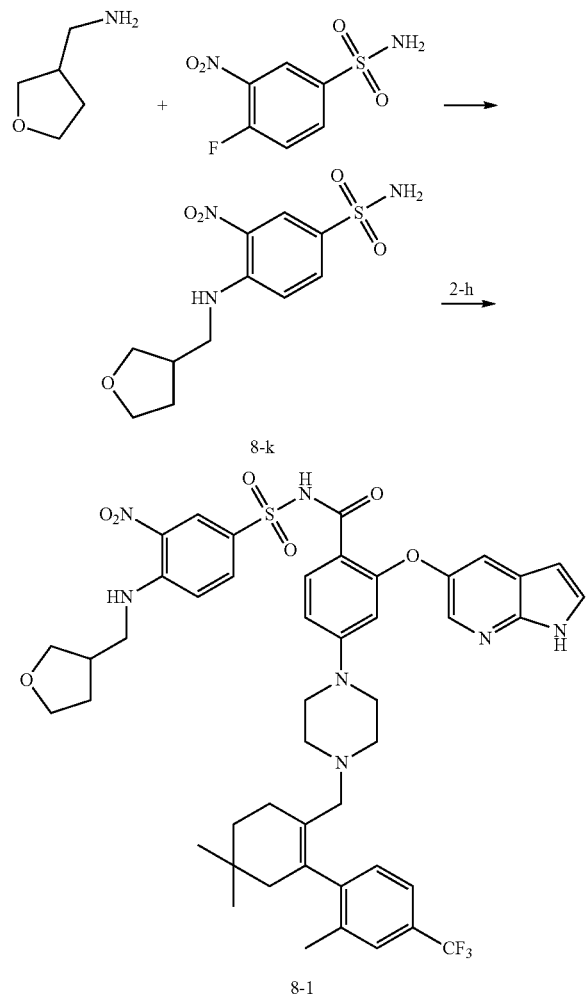

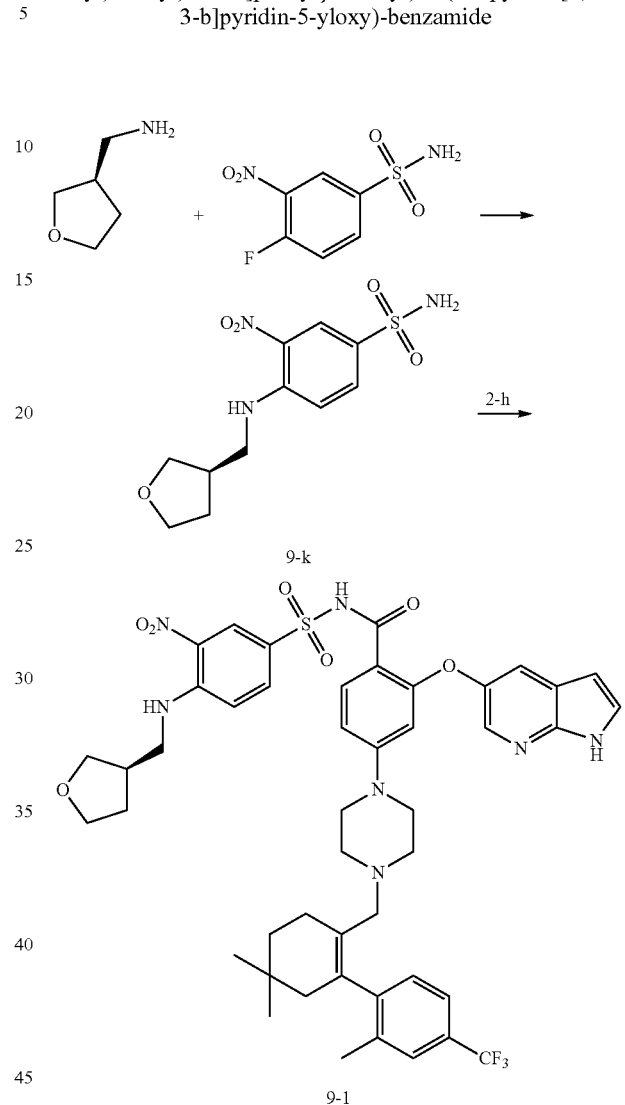

1) Preparation of Compound 8-k

Compound 8-k (1.20 g) was obtained by reference to the preparation method for compound 2-k in step 5) of Example 2, with (R)-(1,4-dioxane)-2-methylamine hydrochloride being replaced by tetrahydrofuran-3-methylamine.

2) Preparation of Compound 8-1

Compound 8-1 was obtained by reference to the preparation method for compound 2-1 in step 6) of Example 2, with compound 2-k being replaced by compound 8-k.

$^1$H NMR (500 MHz, DMSO-$d_6$) δH: 11.74 (2H, m), 8.67 (1H, brs), 8.57 (1H, brs), 8.05 (1H, s), 7.79 (1H, d, J=9.0), 7.40-7.64 (5H, m), 7.17 (1H, d, J=8.0), 7.11 (1H, d, J=9.5), 6.73 (1H, d, J=9.0), 6.40 (1H, s), 6.27 (1H, s), 3.50-3.79 (7H, m), 3.19-3.38 (5H, m), 2.92 (3H, m), 2.58 (2H, m), 2.30 (1H, m), 2.16 (4H, s), 1.93 (3H, m), 1.64 (1H, m), 1.50 (2H, s), 0.97 (6H, s).

ESI-MS: m/z=902.7 [M+H]$^+$.

1) Preparation of Compound 9-k

Compound 9-k (1.10 g) was obtained by reference to the preparation method for compound 2-k in step 5) of Example 2, with (R)-(1,4-dioxane)-2-methylamine hydrochloride being replaced by (3R)-tetrahydrofuran-3-methylamine.

2) Preparation of Compound 9-1

Compound 9-1 was obtained by reference to the preparation method for compound 2-1 in step 6) of Example 2, with compound 2-k being replaced by compound 9-k.

$^1$H NMR (500 MHz, DMSO-$d_6$) δH: 11.74 (2H, m), 8.68 (1H, brs), 8.57 (1H, brs), 8.05 (1H, s), 7.81 (1H, d, J=9.0), 7.49-7.59 (5H, m), 7.17 (1H, d, J=7.5), 7.11 (1H, d, J=9.5), 6.73 (1H, d, J=8.5), 6.40 (1H, s), 6.27 (1H, s), 3.61-3.79 (6H, m), 3.51 (1H, m), 3.09-3.26 (5H, m), 2.91 (3H, m), 2.58 (2H, m), 2.29 (1H, m), 2.16 (4H, s), 1.93 (3H, m), 1.64 (1H, m), 1.49 (2H, s), 0.96 (6H, s).

ESI-MS: m/z=902.7 [M+H]$^+$.

Example 10: (S)-4-(4-{[2-(2-methyl-4-trifluoromethylphenyl)-4,4-dimethylcyclohex-1-enyl]methyl}-piperazin-1-yl)-N-({3-nitro-4-[((tetrahydrofuran-3-yl)methyl)amino]phenyl}sulfonyl)-2-(1H-pyrrolo[2,3-b]pyridin-5-yloxy)-benzamide Example 11: (S)-4-(4-{[2-(2-methyl-4-trifluoromethylphenyl)-4,4-dimethylcyclohex-1-enyl]methyl}-piperazin-1-yl)-N-({3-nitro-4-[((tetrahydrofuran-2-yl)methyl)amino]phenyl}sulfonyl)-2-(1H-pyrrolo[2,3-b]pyridin-5-yloxy)-benzamide

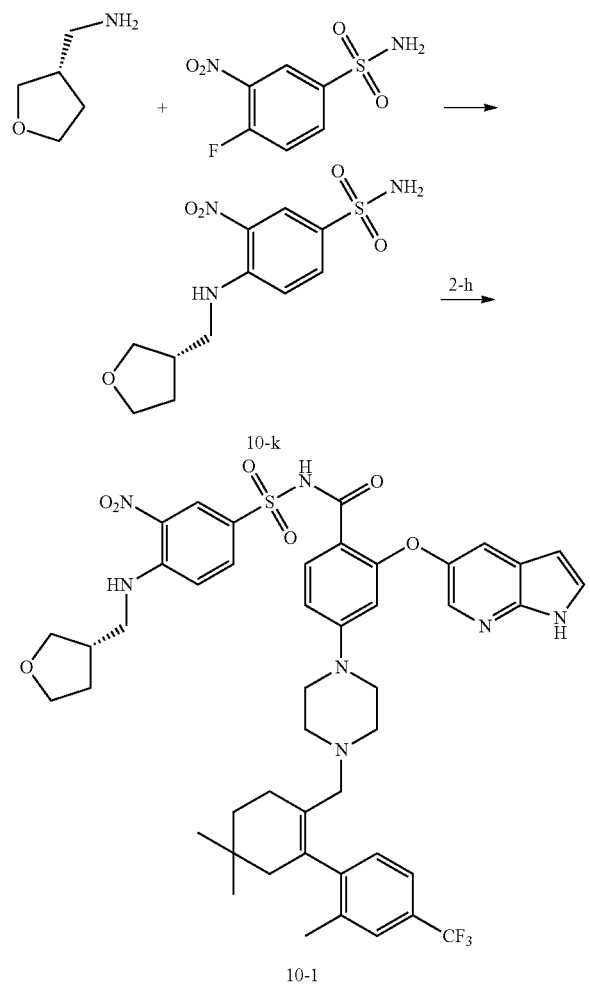

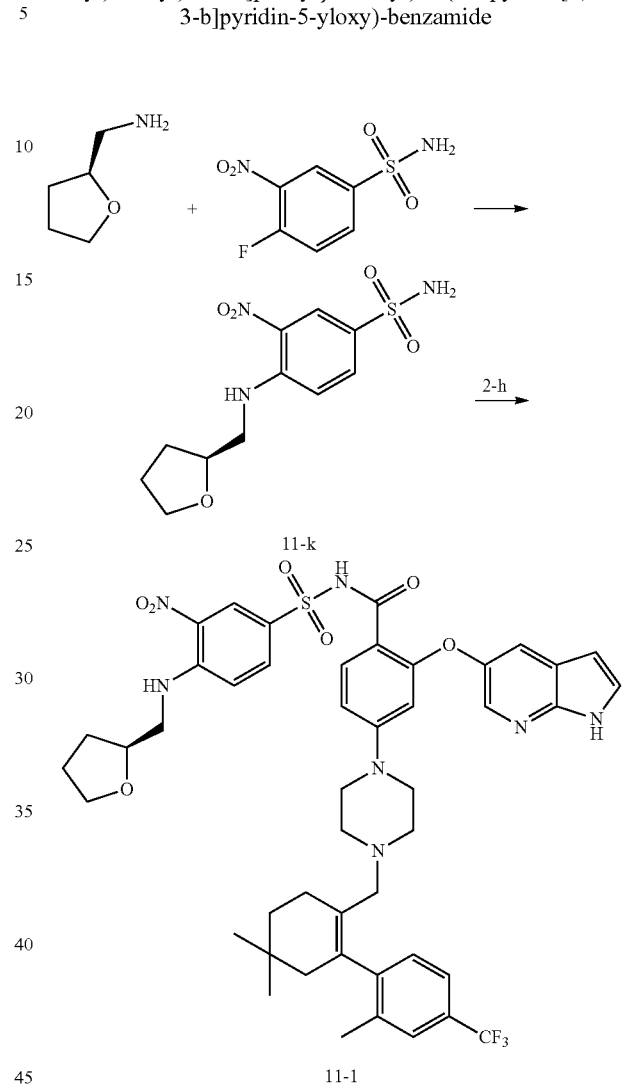

1) Preparation of Compound 10-k

Compound 10-k (1.39 g) was obtained by reference to the preparation method for compound 2-k in step 5) of Example 2, with (R)-(1,4-dioxane)-2-methylamine hydrochloride being replaced by (3S)-tetrahydrofuran-3-methylamine (0.64 g).

2) Preparation of Compound 10-1

Compound 10-1 was obtained by reference to the preparation method for compound 2-1 in step 6) of Example 2, with compound 2-k being replaced by compound 10-k.

$^1$H NMR (500 MHz, DMSO-d$_6$) δH: 11.75 (2H, s), 8.68 (1H, brs), 8.57 (1H, brs), 8.05 (1H, s), 7.81 (1H, d, J=9.0), 7.50-7.59 (5H, m), 7.17 (1H, d, J=8.0), 7.12 (1H, d, J=9.5), 6.73 (1H, d, J=9.0), 6.40 (1H, s), 6.27 (1H, s), 3.50-3.82 (7H, m), 3.23-3.38 (5H, m), 2.92 (3H, m), 2.58 (2H, m), 2.30 (1H, m), 2.16 (4H, s), 1.93 (3H, m), 1.64 (1H, m), 1.49 (2H, s), 0.96 (6H, s).

ESI-MS: m/z=902.7 [M+H]$^+$.

1) Preparation of Compound 11-k

Compound 11-k (1.35 g) was obtained by reference to the preparation method for compound 2-k in step 5) of Example 2, with (R)-(1,4-dioxane)-2-methylamine hydrochloride being replaced by (S)-2-tetrahydrofurfurylamine.

2) Preparation of Compound 11-1

Compound 11-1 was obtained by reference to the preparation method for compound 2-1 in step 6) of Example 2, with compound 2-k being replaced by compound 11-k.

$^1$H NMR (500 MHz, DMSO-d$_6$) 11.74 (2H, s), 8.63 (1H, m), 8.57 (1H, s), 8.05 (1H, s), 7.81 (1H, d, J=9.0 Hz), 7.59 (1H, s), 7.55-7.50 (4H, m), 7.17 (1H, d, J=8.0 Hz), 7.14 (1H, d, J=9.0 Hz), 6.74 (1H, d, J=9.0 Hz), 6.40 (1H, s), 6.28 (1H, s), 4.10 (1H, m), 3.82-3.61 (5H, m), 3.54 (1H, m), 3.41-3.24 (4H, m), 3.00-2.87 (3H, m), 2.61 (1H, m), 2.28 (1H, m), 2.16 (4H, m), 2.03-1.84 (4H, m), 1.62 (1H, m), 1.49 (2H, m), 1.23 (1H, m), 0.96 (6H, s)

ESI-MS: m/z=902.7 [M+H]$^+$.

Example 12: (R)-4-(4-{[2-(2-methyl-4-trifluoromethylphenyl)-4,4-dimethylcyclohex-1-enyl]methyl}-piperazin-1-yl)-N-({3-nitro-4-[((tetrahydrofuran-2-yl)methyl)amino]phenyl}sulfonyl)-2-(1H-pyrrolo[2,3-b]pyridin-5-yloxy)-benzamide Example 13: 4-(4-{[2-(2-methyl-4-trifluoromethylphenyl)-4,4-dimethylcyclohex-1-enyl]methyl}-piperazin-1-yl)-N-({3-nitro-4-[(tetrahydropyran-4-yl)amino]phenyl}sulfonyl)-2-(1H-pyrrolo[2,3-b]pyridin-5-yloxy)-benzamide

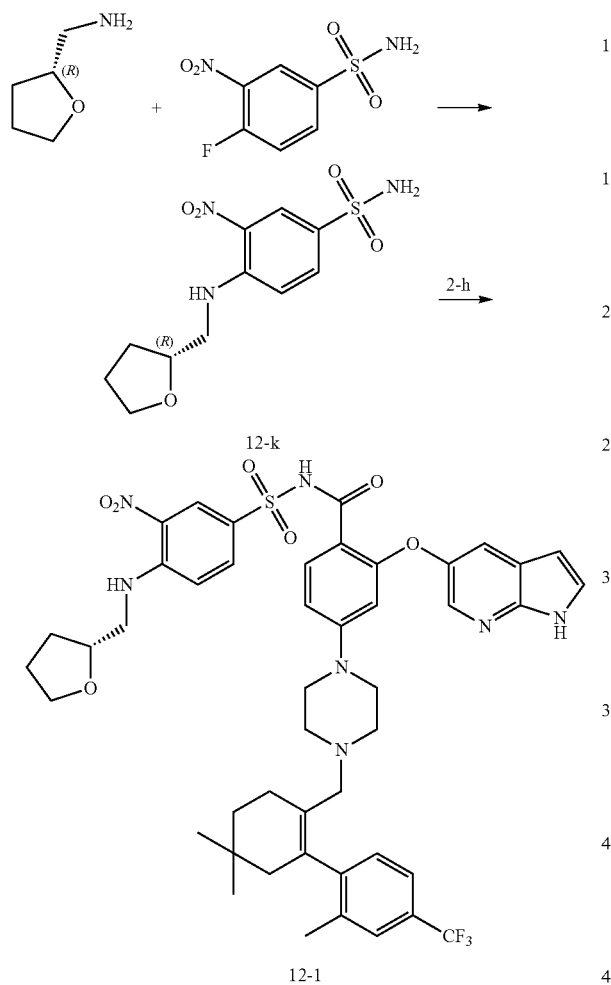

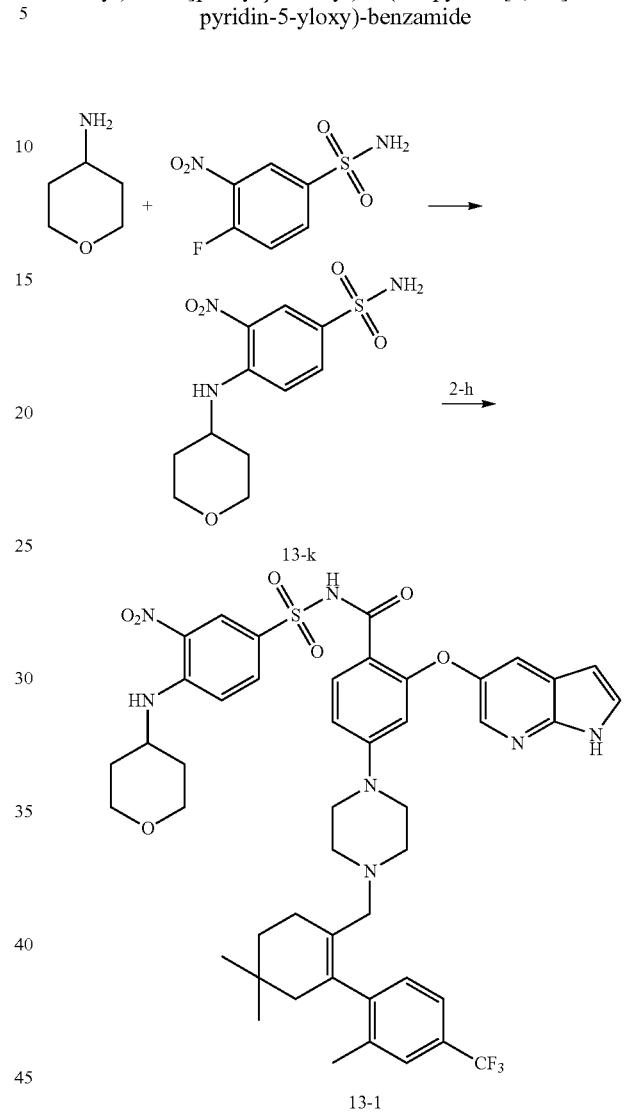

1) Preparation of Compound 12-k

Compound 12-k (1.38 g) was obtained by reference to the preparation method for compound 2-k in step 5) of Example 2, with (R)-(1,4-dioxane)-2-methylamine hydrochloride being replaced by (R)-2-tetrahydrofurfurylamine.

2) Preparation of Compound 12-1

Compound 12-1 was obtained by reference to the preparation method for compound 2-1 in step 6) of Example 2, with compound 2-k being replaced by compound 12-k.

$^1$H NMR (500 MHz, DMSO-$d_6$) 11.74 (2H, s), 8.63 (1H, m), 8.56 (1H, m), 8.04 (1H, m), 7.81 (1H, d, J=9.0 Hz), 7.59 (1H, s), 7.54-7.50 (4H, m), 7.17 (1H, d, J=8.0 Hz), 7.14 (1H, d, J=9.0 Hz), 6.73 (1H, d, J=9.0 Hz), 6.40 (1H, s), 6.28 (1H, s), 3.85-3.52 (7H, m), 3.41-3.23 (4H, m), 3.00-2.91 (3H, m), 2.61 (1H, m), 2.28 (1H, m), 2.16 (4H, m), 2.08 (1H, m), 2.01-1.84 (3H, m), 1.63 (1H, m), 1.49 (2H, m), 1.23 (1H, m), 0.96 (6H, s).

ESI-MS: m/z=902.7 [M+H]$^+$.

1) Preparation of Compound 13-k

Compound 13-k (1.70 g) was obtained by reference to the preparation method for compound 2-k in step 5) of Example 2, with (R)-(1,4-dioxane)-2-methylamine hydrochloride being replaced by 4-aminotetrahydropyran.

2) Preparation of Compound 13-1

Compound 13-1 was obtained by reference to the preparation method for compound 2-1 in step 6) of Example 2, with compound 2-k being replaced by compound 13-k.

$^1$H NMR (500M Hz, DMSO-$d_6$) δH: 11.74 (2H, s), 8.57 (1H, brs), 8.26 (1H, d, J=7.0), 8.04 (1H, s), 7.82 (1H, d, J=9.0), 7.59 (1H, s), 7.49-7.54 (4H, m), 7.20 (1H, d, J=9.5), 7.17 (1H, d, J=8.0), 6.73 (1H, d, J=8.5), 6.40 (1H, s), 6.27 (1H, s), 3.88 (3H, m), 3.45-3.74 (5H, m), 3.23 (3H, m), 3.02 (3H, m), 2.61 (1H, m), 2.30 (1H, m), 2.16 (4H, s), 1.75-1.96 (4H, m), 1.61 (2H, m), 1.49 (2H, s), 0.96 (6H, s).

ESI-MS: m/z=902.7 [M+H]$^+$.

Example 14: (S)-4-(4-{[2-(2-methyl-4-trifluoromethylphenyl)-4,4-dimethylcyclohex-1-enyl]methyl}-piperazin-1-yl)-N-({3-nitro-4-[(tetrahydropyran-3-yl)amino]phenyl}sulfonyl)-2-(1H-pyrrolo[2,3-b]pyridin-5-yloxy)-benzamide Example 15: (R)-4-(4-{[2-(2-methyl-4-trifluoromethylphenyl)-4,4-dimethylcyclohex-1-enyl]methyl}-piperazin-1-yl)-N-({3-nitro-4-[((tetrahydropyran-3-yl)methyl)amino]phenyl}sulfonyl)-2-(1H-pyrrolo[2,3-b]pyridin-5-yloxy)-benzamide

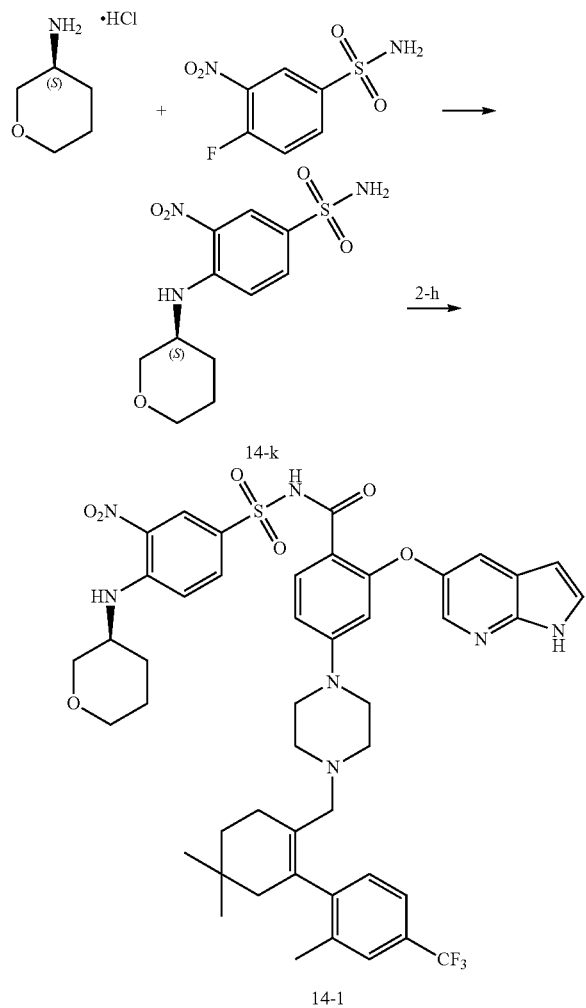

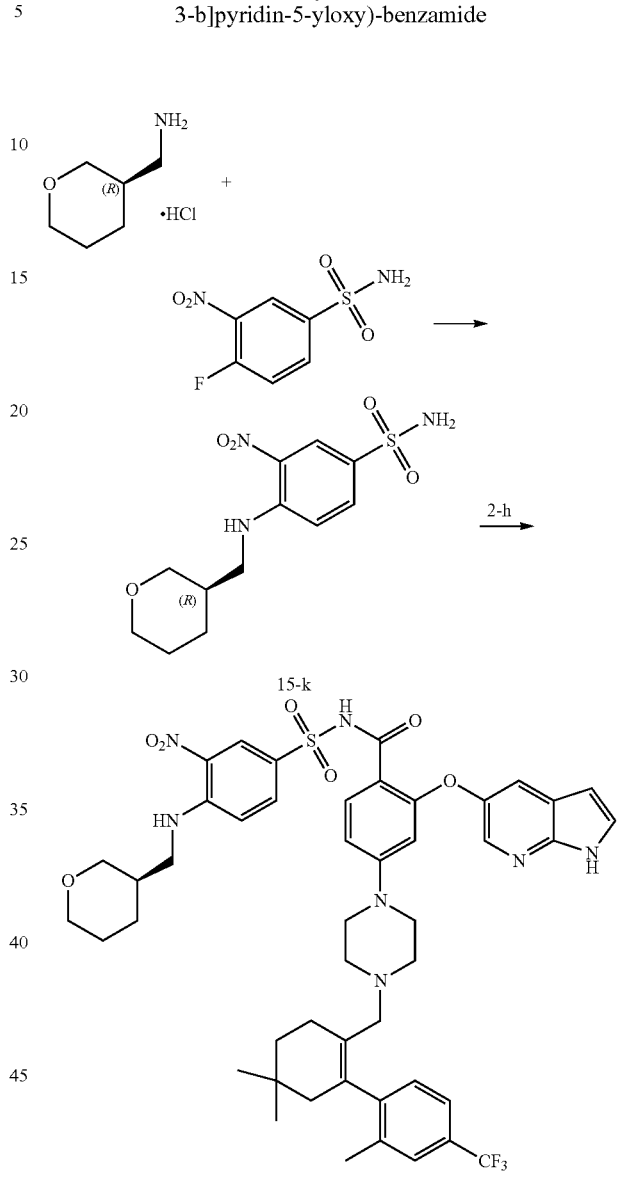

1) Preparation of Compound 14-k

Compound 14-k (1.08 g) was obtained by reference to the preparation method for compound 2-k in step 5) of Example 2, with (R)-(1,4-dioxane)-2-methylamine hydrochloride being replaced by (S)-3-aminotetrahydropyran hydrochloride.

2) Preparation of Compound 14-1

Compound 14-1 was obtained by reference to the preparation method for compound 2-1 in step 6) of Example 2, with compound 2-k being replaced by compound 14-k.

$^1$H NMR (500 MHz, DMSO-$d_6$) δH: 11.74 (2H, s), 8.58 (1H, brs), 8.53 (1H, d, J=7.5), 8.05 (1H, s), 7.83 (1H, d, J=9.5), 7.49-7.59 (5H, m), 7.17 (1H, d, J=8.5), 6.73 (1H, d, J=8.5), 6.40 (1H, s), 6.26 (1H, s), 3.77-3.86 (3H, m), 3.55-3.63 (2H, m), 2.90-3.24 (7H, m), 2.59 (1H, m), 2.26 (1H, m), 2.16 (3H, s), 2.08 (3H, s), 1.86-1.96 (3H, m), 1.75 (2H, m), 1.53 (3H, m), 0.96 (6H, s).

ESI-MS: m/z=902.7 [M+H]$^+$.

1) Preparation of Compound 15-k

Compound 15-k (0.36 g) was obtained by reference to the preparation method for compound 2-k in step 5) of Example 2, with (R)-(1,4-dioxane)-2-methylamine hydrochloride being replaced by (R)-3-aminomethyltetrahydropyran hydrochloride.

2) Preparation of Compound 15-1

Compound 15-1 was obtained by reference to the preparation method for compound 2-1 in step 6) of Example 2, with compound 2-k being replaced by compound 15-k.

$^1$H NMR (500 MHz, DMSO-$d_6$) 11.75 (2H, s), 8.61 (1H, m), 8.57 (1H, s), 8.05 (1H, s), 7.81 (1H, d, J=9.0 Hz), 7.59 (1H, s), 7.55-7.49 (4H, m), 7.17 (1H, d, J=8.0 Hz), 7.10 (1H, d, J=9.0 Hz), 6.73 (1H, d, J=9.0 Hz), 6.40 (1H, s), 6.27 (1H, s), 3.87-3.60 (5H, m), 3.52-3.16 (7H, m), 3.01-2.91 (2H, m), 2.62 (1H, m), 2.28 (1H, m), 2.16 (3H, s), 2.13 (1H, m), 2.03-1.81 (4H, m), 1.61 (1H, m), 1.49 (3H, m), 1.33-1.24 (2H, m), 0.96 (6H, s)

ESI-MS: m/z=916.7 [M+H]⁺.

Example 16: (S)-4-(4-{[2-(2-methyl-4-trifluoromethylphenyl)-4,4-dimethylcyclohex-1-enyl]methyl}-piperazin-1-yl)-N-({3-nitro-4-[((tetrahydropyran-3-yl)methyl)amino]phenyl}sulfonyl)-2-(1H-pyrrolo[2,3-b]pyridin-5-yloxy)-benzamide

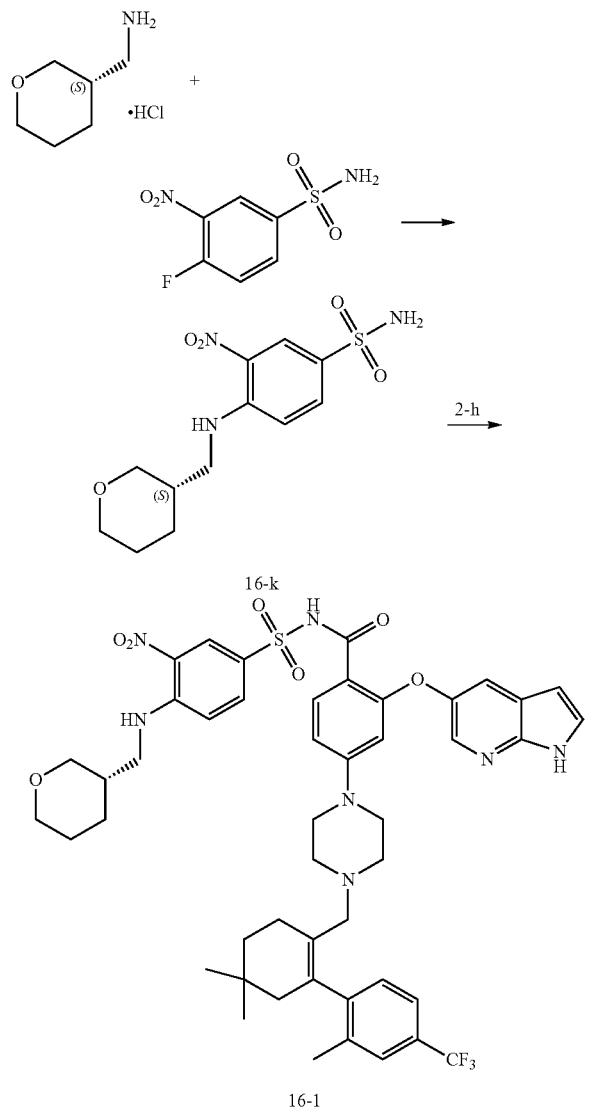

1) Preparation of Compound 16-k

Compound 16-k (0.39 g) was obtained by reference to the preparation method for compound 2-k in step 5) of Example 2, with (R)-(1,4-dioxane)-2-methylamine hydrochloride being replaced by (S)-3-aminomethyltetrahydropyran hydrochloride.

2) Preparation of Compound 16-1

Compound 16-1 was obtained by reference to the preparation method for compound 2-1 in step 6) of Example 2, with compound 2-k being replaced by compound 16-k.

¹H NMR (500 MHz, DMSO-d₆) 11.75-11.72 (2H, s), 8.62 (1H, m), 8.57 (1H, s), 8.05 (1H, m), 7.81 (1H, d, J=9.0 Hz), 7.59 (1H, s), 7.55-7.49 (4H, m), 7.17 (1H, d, J=8.0 Hz), 7.10 (1H, d, J=9.0 Hz), 6.73 (1H, d, J=9.0 Hz), 6.40 (1H, s), 6.27 (1H, s), 3.80-3.60 (4H, m), 3.37-3.16 (6H, m), 3.01-2.91 (2H, m), 2.61 (1H, m), 2.28 (1H, m), 2.16 (4H, m), 2.03-1.81 (4H, m), 1.61 (1H, m), 1.49-1.46 (3H, m), 1.35-1.23 (4H, m), 0.96 (6H, s)

ESI-MS: m/z=916.7 [M+H]⁺.

Example 17: 4-(4-{[2-(2-methyl-4-trifluoromethylphenyl)-4,4-dimethylcyclohex-1-enyl]methyl}-piperazin-1-yl)-N-({3-nitro-4-[((2-tetrahydropyran-3-yl)ethyl)amino]phenyl}sulfonyl)-2-(1H-pyrrolo[2,3-b]pyridin-5-yloxy)-benzamide

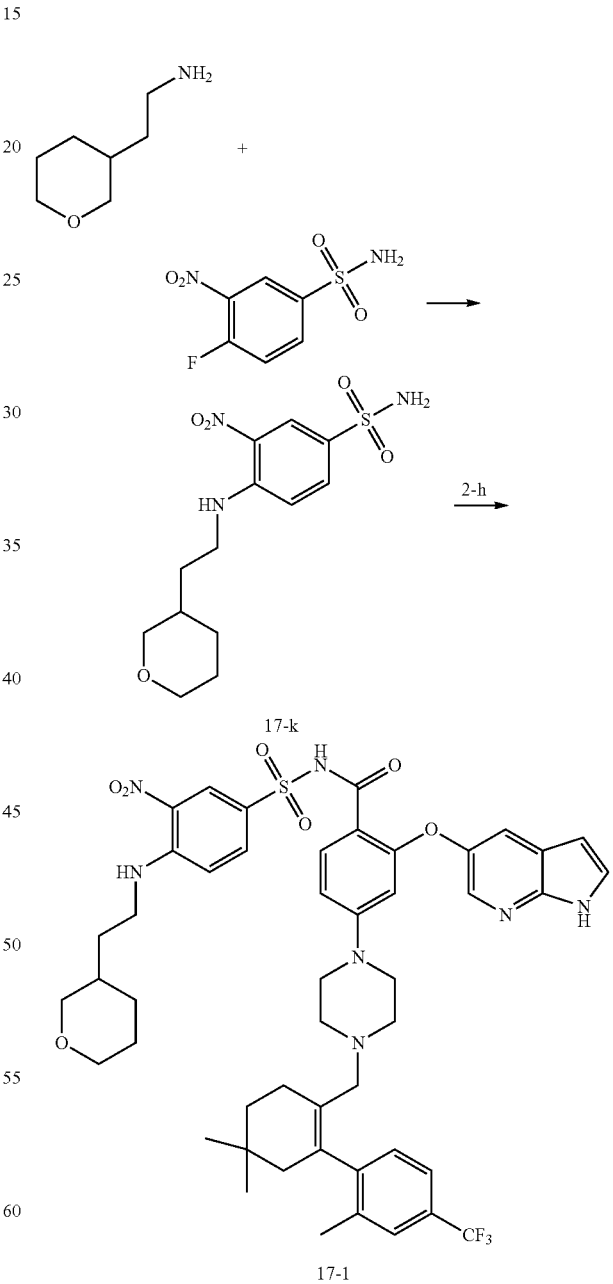

1) Preparation of Compound 17-k

Compound 17-k (1.06 g) was obtained by reference to the preparation method for compound 2-k in step 5) of Example 2, with (R)-(1,4-dioxane)-2-methylamine hydrochloride being replaced by 2-(tetrahydro-2H-pyran-3-yl)ethylamine.

2) Preparation of Compound 17-1

Compound 17-1 was obtained by reference to the preparation method for compound 2-1 in step 6) of Example 2, with compound 2-k being replaced by compound 17-k.

$^1$H NMR (500 MHz, DMSO-$d_6$) 11.75-11.73 (2H, s), 8.59-8.56 (2H, m), 8.04 (1H, s), 7.81 (1H, d, J=9.0 Hz), 7.59 (1H, s), 7.55-7.49 (4H, m), 7.17 (1H, d, J=8.0 Hz), 7.07 (1H, d, J=9.0 Hz), 6.73 (1H, d, J=9.0 Hz), 6.40 (1H, s), 6.30 (1H, s), 3.85-3.60 (4H, m), 3.40-3.23 (6H, m), 3.04-2.91 (4H, m), 2.61 (1H, m), 2.28 (1H, m), 2.16 (3H, s), 2.13 (1H, m), 1.96-1.84 (3H, m), 1.60-1.38 (7H, m), 1.23-1.09 (2H, m), 0.96 (6H, s)

ESI-MS: m/z=930.7 [M+H]$^+$.

Example 18: (S)-4-(4-{[2-(2-methyl-4-trifluoromethylphenyl)-4,4-dimethylcyclohex-1-enyl]methyl}-piperazin-1-yl)-N-({3-nitro-4-[((4-acetylmorpholin-2-yl)methyl)amino]phenyl}sulfonyl)-2-(1H-pyrrolo[2,3-b]pyridin-5-yloxy)-benzamide

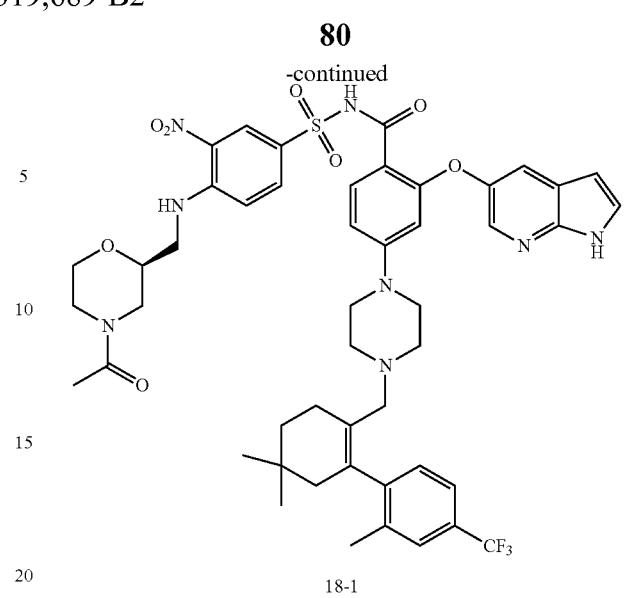

18-1

1) Preparation of Compound 18-k

Compound 18-k (0.89 g) was obtained by reference to the preparation method for compound 2-k in step 5) of Example 2, with (R)-(1,4-dioxane)-2-methylamine hydrochloride being replaced by (S)-2-aminomethyl-4-acetylmorpholine.

ESI-MS: m/z=359.0 [M+H]$^+$.

2) Preparation of Compound 18-1

Compound 18-1 was obtained by reference to the preparation method for compound 2-1 in step 6) of Example 2, with compound 2-k being replaced by compound 18-k.

$^1$H NMR (500 MHz, DMSO-$d_6$) 11.72 (2H, s), 8.64 (1H, m), 8.57 (1H, t, J=3.0 Hz), 8.04 (1H, d, J=3.0 Hz), 7.84 (1H, m), 7.59 (1H, s), 7.55 (1H, d, J=2.5 Hz), 7.53-7.52 (2H, m), 7.50 (1H, d, J=8.0 Hz), 7.18-7.24 (2H, m), 6.73 (1H, dd, J=9.0, 2.0 Hz), 6.40 (1H, dd, J=3.0, 2.0 Hz), 6.28 (1H, d, J=2.0 Hz), 4.32 (1H, d, J=13.0 Hz), 4.14 (1H, d, J=13.0 Hz), 3.91-3.84 (2H, m), 3.73-3.60 (6H, m), 3.52-3.36 (3H, m), 3.26-2.99 (2H, m), 3.01 (1H, m), 2.92 (1H, m), 2.71 (1H, m), 2.55 (1H, m), 2.51 (3H, m), 2.29 (1H, m), 2.16 (3H, m), 2.13 (1H, m), 1.92 (2H, m), 1.50 (2H, m), 0.97 (3H, s), 0.96 (3H, s)

ESI-MS: m/z=959.7 [M+H]$^+$.

Example 19: (R)-4-(4-{[2-(2-methyl-4-trifluoromethylphenyl)-4,4-dimethylcyclohex-1-enyl]methyl}-piperazin-1-yl)-N-({3-nitro-4-[((4-acetylmorpholin-2-yl)methyl)amino]phenyl}sulfonyl)-2-(1H-pyrrolo[2,3-b]pyridin-5-yloxy)-benzamide

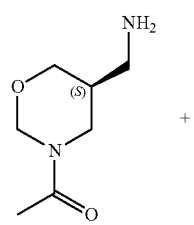

+

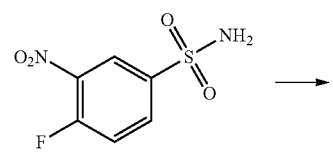

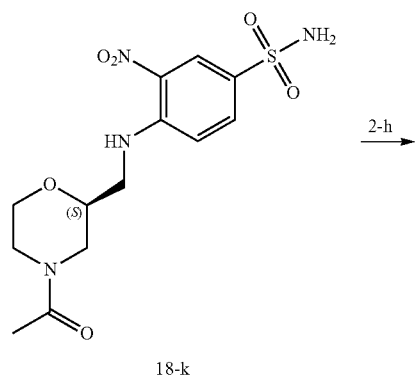

18-k

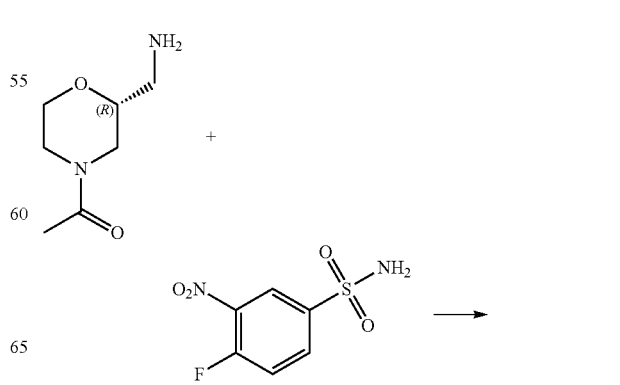

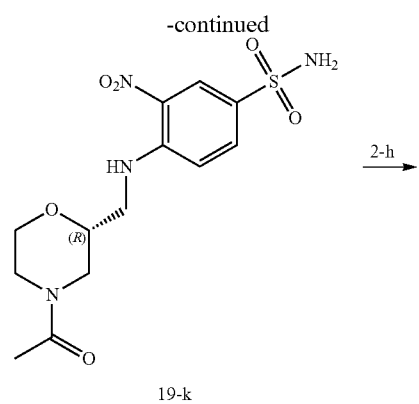

19-k

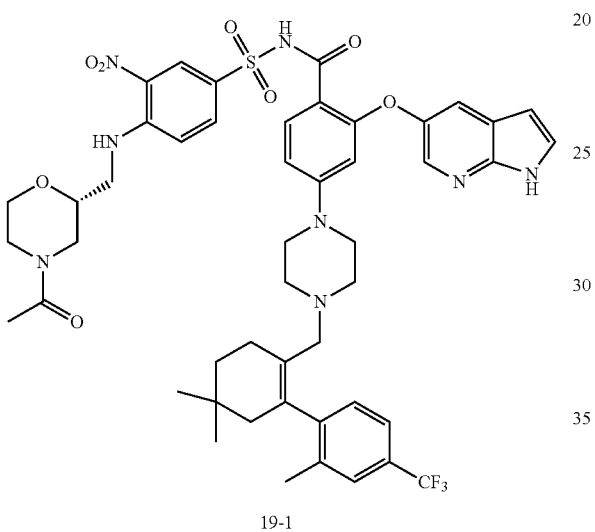

19-1

1) Preparation of Compound 19-k

Compound 19-k (0.89 g) was obtained by reference to the preparation method for compound 2-k in step 5) of Example 2, with (R)-(1,4-dioxane)-2-methylamine hydrochloride being replaced by (R)-2-aminomethyl-4-acetylmorpholine. ESI-MS: m/z=359.0 [M+H]+.

2) Preparation of Compound 19-1

Compound 19-1 was obtained by reference to the preparation method for compound 2-1 in step 6) of Example 2, with compound 2-k being replaced by compound 19-k.

$^1$H NMR (500 MHz, DMSO-d$_6$) 11.72 (2H, s), 8.64 (1H, m), 8.57 (1H, t, J=3.0 Hz), 8.04 (1H, d, J=3.0 Hz), 7.84 (1H, m), 7.59 (1H, s), 7.55 (1H, d, J=2.5 Hz), 7.53-7.52 (2H, m), 7.50 (1H, d, J=8.0 Hz), 7.18-7.24 (2H, m), 6.73 (1H, dd, J=9.0, 2.0 Hz), 6.40 (1H, dd, J=3.0, 2.0 Hz), 6.28 (1H, d, J=2.0 Hz), 4.32 (1H, d, J=13.0 Hz), 4.14 (1H, d, J=13.0 Hz), 3.91-3.84 (2H, m), 3.73-3.60 (6H, m), 3.52-3.36 (3H, m), 3.26-2.99 (2H, m), 3.01 (1H, m), 2.92 (1H, m), 2.71 (1H, m), 2.55 (1H, m), 2.51 (3H, m), 2.29 (1H, m), 2.16 (3H, m), 2.13 (1H, m), 1.92 (2H, m), 1.50 (2H, m), 0.97 (3H, s), 0.96 (3H, s)

ESI-MS: m/z=959.7 [M+H]+.

Example 20: (S)-4-(4-{[2-(2-methyl-4-trifluoromethylphenyl)-4,4-dimethylcyclohex-1-enyl]methyl}-piperazin-1-yl)-N-({3-nitro-4-[((4-isobutyrylmorpholin-2-yl)methyl)amino]phenyl}sulfonyl)-2-(1H-pyrrolo[2,3-b]pyridin-5-yloxy)-benzamide

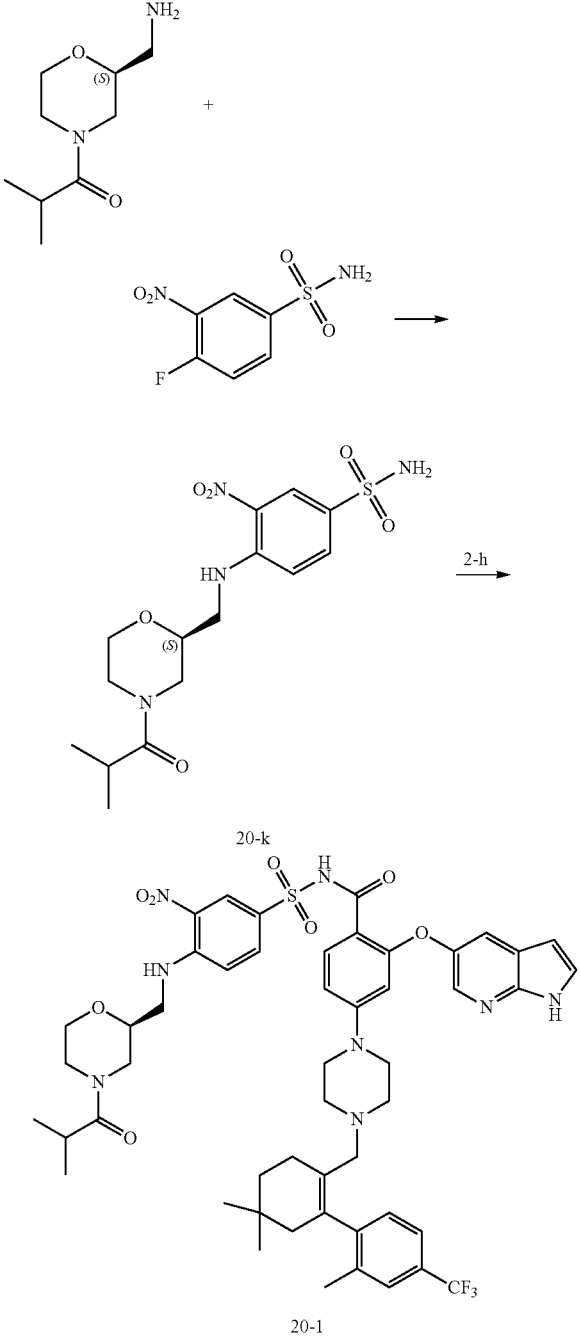

1) Preparation of Compound 20-k

Compound 20-k (0.82 g) was obtained by reference to the preparation method for compound 2-k in step 5) of Example 2, with (R)-(1,4-dioxane)-2-methylamine hydrochloride being replaced by (S)-2-aminomethyl-4-isobutyrylmorpholine. ESI-MS: m/z=387.0 [M+H]+.

2) Preparation of Compound 20-1

Compound 20-1 was obtained by reference to the preparation method for compound 2-1 in step 6) of Example 2, with compound 2-k being replaced by compound 20-k.

$^1$H NMR (500 MHz, DMSO-$d_6$) 11.71-11.65 (2H, s), 8.65 (1H, t, J=5.0 Hz), 8.57 (1H, s), 8.04 (1H, d, J=2.5 Hz), 7.83 (1H, m), 7.58 (1H, s), 7.55-7.49 (4H, m), 7.17 (2H, m), 6.73 (1H, dd, J=9.0, 2.0 Hz), 6.39 (1H, dd, J=3.0, 2.0 Hz), 6.27 (1H, s), 4.35 (1H, d, J=13.0 Hz), 4.18 (1H, d, J=13.0 Hz), 3.99 (1H, d, J=13.0 Hz), 3.81 (1H, m), 3.74 (1H, m), 3.62-3.60 (4H, m), 3.47 (1H, m), 3.26-3.16 (4H, m), 3.02 (2H, m), 2.87 (2H, m), 2.68 (1H, m), 2.56 (1H, m), 2.29 (1H, m), 2.18 (1H, m), 2.16 (3H, m), 1.92 (2H, m), 1.50 (2H, m), 1.01-0.96 (12H, m)

ESI-MS: m/z=987.8 [M+H]$^+$.

Example 21: (R)-4-(4-{[2-(2-methyl-4-trifluoromethylphenyl)-4,4-dimethylcyclohex-1-enyl]methyl}-piperazin-1-yl)-N-({3-nitro-4-[((4-isobutyrylmorpholin-2-yl)methyl)amino]phenyl}sulfonyl)-2-(1H-pyrrolo[2,3-b]pyridin-5-yloxy)-benzamide

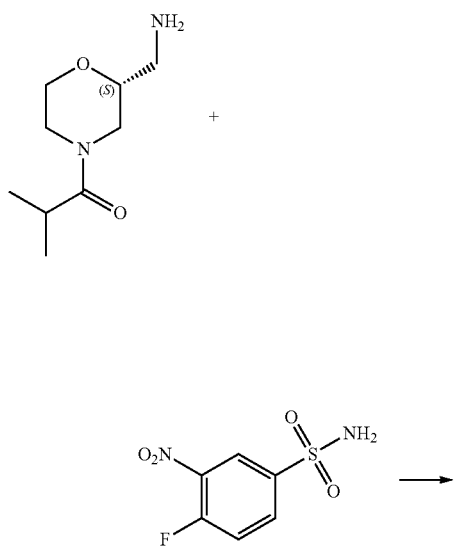

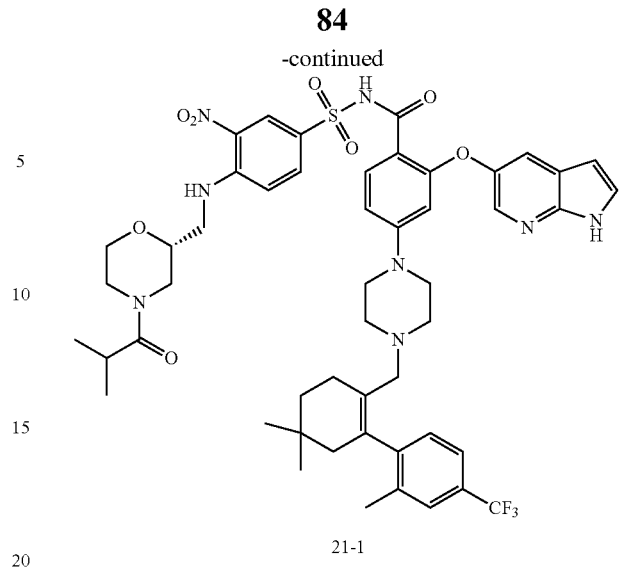

21-1

1) Preparation of Compound 21-k

Compound 21-k (0.87 g) was obtained by reference to the preparation method for compound 2-k in step 5) of Example 2, with (R)-(1,4-dioxane)-2-methylamine hydrochloride being replaced by (R)-2-aminomethyl-4-isobutyrylmorpholine. ESI-MS: m/z=387.0 [M+H]$^+$.

2) Preparation of Compound 21-1

Compound 21-1 was obtained by reference to the preparation method for compound 2-1 in step 6) of Example 2, with compound 2-k being replaced by compound 21-k.

$^1$H NMR (500 MHz, DMSO-$d_6$), δH: 11.74 (brs, 2H), 8.67 (brs, 1H), 8.57 (s, 1H), 8.05 (s, 1H), 7.83 (m, 1H), 7.59 (s, 1H), 7.52 (m, 4H), 7.16 (m, 2H), 6.73 (d, J=8.5 Hz, 1H), 6.40 (s, 1H), 6.27 (s, 1H), 3.90 (d, J=10.7 Hz, 1H), 3.79 (m, 2H), 3.63 (m, 4H), 3.47 (m, 2H), 3.38 (m, 1H), 3.27 (m, 3H), 3.16 (m, 1H), 3.02 (m, 2H), 2.87 (m, 2H), 2.60 (m, 2H), 2.30 (m, 1H), 2.16 (s, 3H), 2.13 (m, 1H), 1.91 (m, 2H), 1.49 (brs, 2H), 0.99 (m, 6H), 0.96 (m, 6H).

ESI-MS: m/z=987.8 [M+H]$^+$.

Example 22: (S)-4-(4-{[2-(2-methyl-4-trifluoromethylphenyl)-4,4-dimethylcyclohex-1-enyl]methyl}-piperazin-1-yl)-N-({3-nitro-4-[((4-(methylsulfonyl)morpholin-2-yl)methyl)amino]phenyl}sulfonyl)-2-(1H-pyrrolo[2,3-b]pyridin-5-yloxy)-benzamide

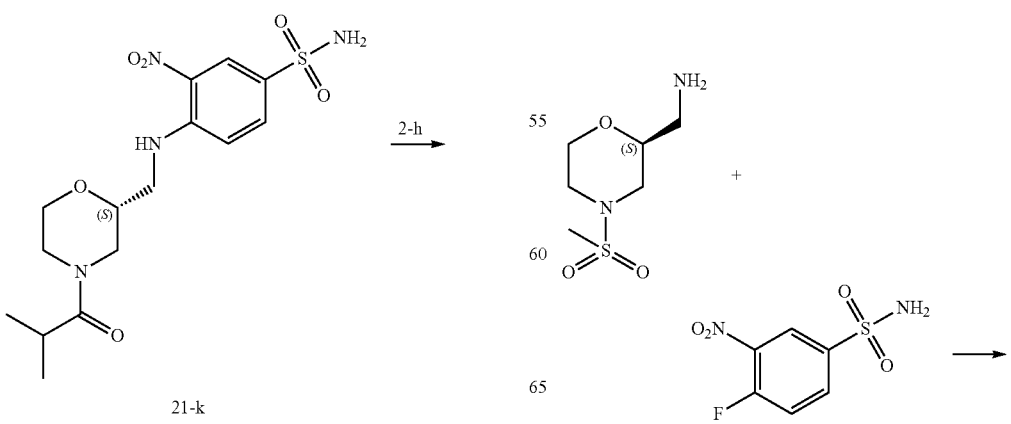

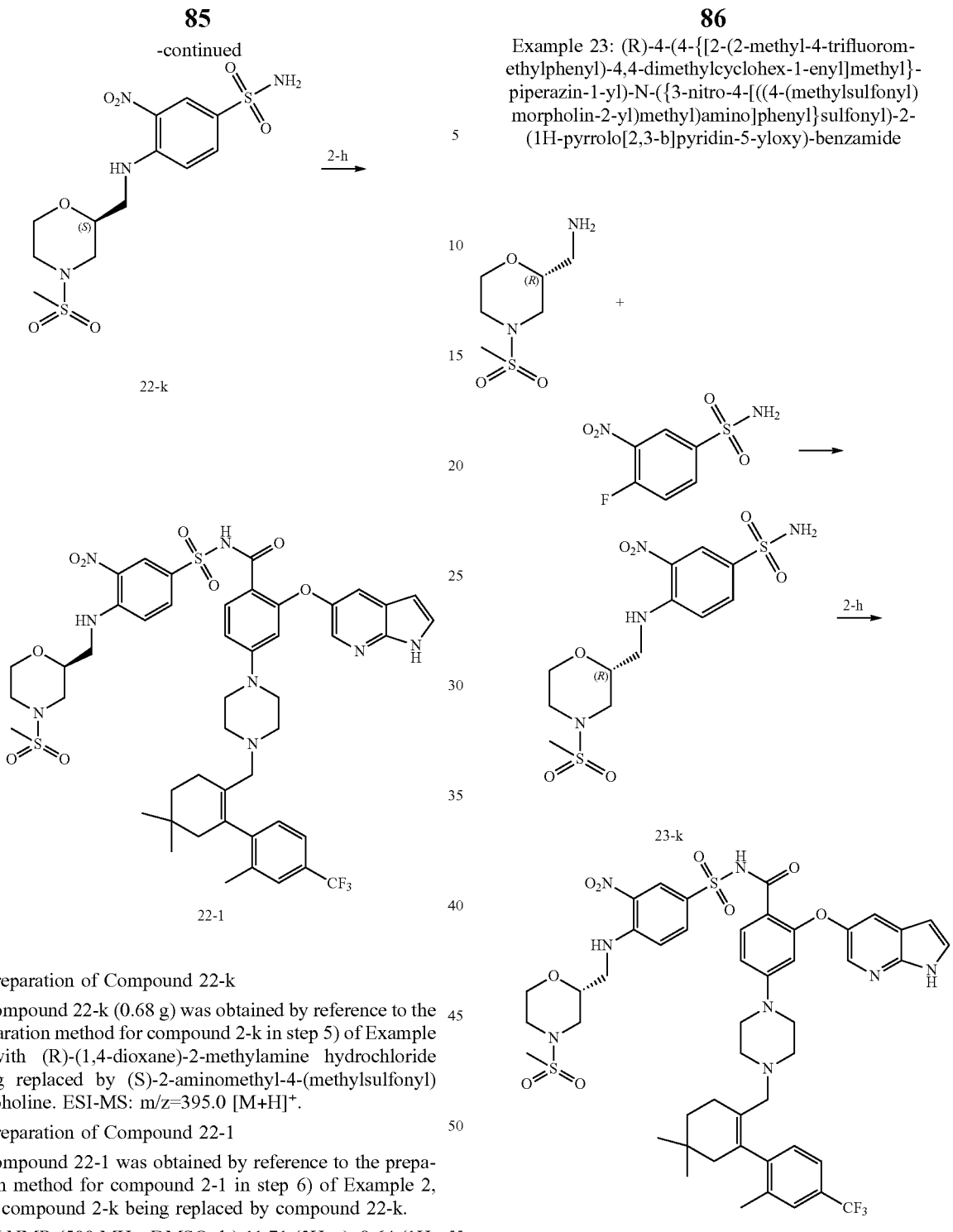

Example 23: (R)-4-(4-{[2-(2-methyl-4-trifluoromethylphenyl)-4,4-dimethylcyclohex-1-enyl]methyl}-piperazin-1-yl)-N-({3-nitro-4-[((4-(methylsulfonyl)morpholin-2-yl)methyl)amino]phenyl}sulfonyl)-2-(1H-pyrrolo[2,3-b]pyridin-5-yloxy)-benzamide 1) Preparation of Compound 22-k Compound 22-k (0.68 g) was obtained by reference to the preparation method for compound 2-k in step 5) of Example 2, with (R)-(1,4-dioxane)-2-methylamine hydrochloride being replaced by (S)-2-aminomethyl-4-(methylsulfonyl)morpholine. ESI-MS: m/z=395.0 [M+H]⁺.

2) Preparation of Compound 22-1

Compound 22-1 was obtained by reference to the preparation method for compound 2-1 in step 6) of Example 2, with compound 2-k being replaced by compound 22-k.

¹H NMR (500 MHz, DMSO-d₆) 11.71 (2H, s), 8.64 (1H, t, J=6.0 Hz), 8.57 (1H, d, J=8.5 Hz), 8.05 (1H, d, J=3.0 Hz), 7.83 (1H, dd, J=9.0, 2.0 Hz), 7.58 (1H, s), 7.55 (1H, d, J=2.5 Hz), 7.54-7.49 (3H, m), 7.18 (1H, s), 7.16 (1H, d, J=2.0 Hz), 6.73 (1H, dd, J=9.0, 2.0 Hz), 6.40 (1H, dd, J=3.0, 2.0 Hz), 6.27 (1H, d, J=2.0 Hz), 4.85 (2H, m), 3.98 (1H, d, J=11.0 Hz), 3.80-3.74 (2H, m), 3.67-3.55 (5H, m), 3.49 (1H, m), 3.56 (1H, d, J=11.0 Hz), 3.31-3.19 (3H, m), 3.02 (2H, m), 2.92 (3H, s), 2.85 (1H, m), 2.67 (1H, m), 2.28 (1H, m), 2.18 (1H, m), 2.16 (3H, m), 1.92 (2H, m), 1.50 (2H, m), 0.97 (3H, s), 0.96 (3H, s)

ESI-MS: m/z=995.8 [M+H]⁺.

1) Preparation of Compound 23-k

Compound 23-k (0.65 g) was obtained by reference to the preparation method for compound 2-k in step 5) of Example 2, with (R)-(1,4-dioxane)-2-methylamine hydrochloride being replaced by (R)-2-aminomethyl-4-(methylsulfonyl)morpholine. ESI-MS: m/z=395.0 [M+H]⁺.

2) Preparation of Compound 23-1

Compound 23-1 was obtained by reference to the preparation method for compound 2-1 in step 6) of Example 2, with compound 2-k being replaced by compound 23-k.

¹H NMR (500 MHz, DMSO-d₆), δH: 11.74 (s, 2H), 8.66 (t, J=5.4 Hz, 1H), 8.57 (d, J=1.8 Hz, 1H), 8.04 (d, J=2.2 Hz, 1H), 7.84 (d, J=9.1 Hz, 1H), 7.59 (s, 1H), 7.55 (d, J=2.0 Hz, 1H), 7.51 (m, 3H), 7.17 (d, J=8.8 Hz, 2H), 6.73 (d, J=8.7 Hz, 1H), 6.40 (s, 1H), 6.27 (s, 1H), 3.98 (d, 1H), 3.78 (m, 2H), 3.65 (m, 3H), 3.57 (m, 3H), 3.49 (m, 1H), 3.35 (m, 1H), 3.26 (m, 3H), 3.00 (m, 2H), 2.93 (s, 3H), 2.85 (m, 1H), 2.61 (m, 1H), 2.69 (t, J=10.9 Hz, 1H), 2.28 (m, 1H), 2.18 (m, 1H), 2.16 (s, 3H), 1.91 (m, 2H), 1.49 (m, 2H), 0.96 (s, 3H).
ESI-MS: m/z=995.8 [M+H]⁺.
The Following Compounds were Prepared with Reference to the Preparation of Example 1, with the Fragments in the Table Below Used as Starting Materials:
| Fragment | Compound |
|---|---|
| 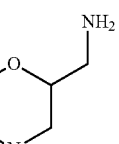 | 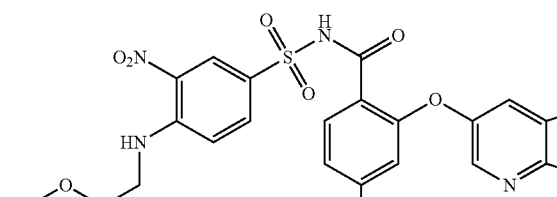 |

| Fragment | Compound |
|---|---|
| (structure) | (structure) |
| (structure) | (structure) |
| (structure) | (structure) |

-continued
| Fragment | Compound |
|---|---|
| 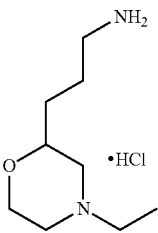 | 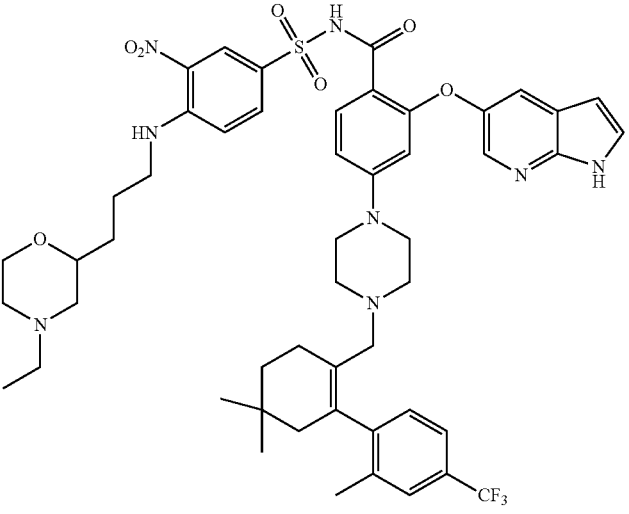 [SMILES: CCN1CCOC(CCCNc2ccc(S(=O)(=O)NC(=O)c3ccc(N4CCN(CC5=C(c6ccc(C(F)(F)F)cc6C)CC(C)(C)CC5)CC4)cc3Oc3cnc4[nH]ccc4c3)cc2[N+](=O)[O-])C1] |
| 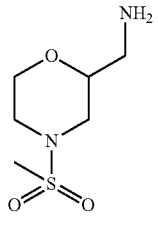 | 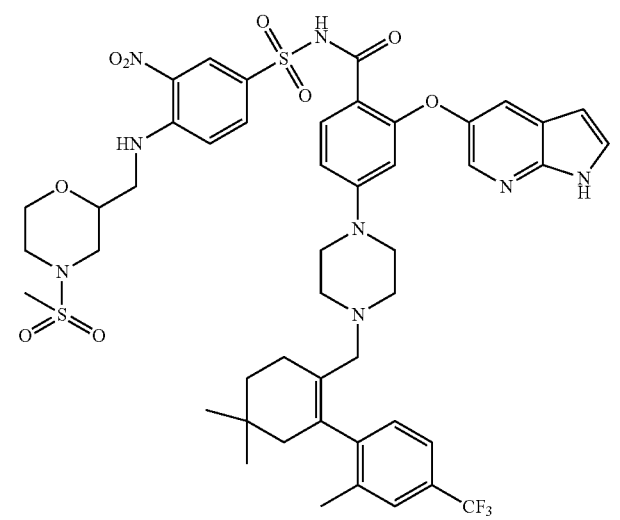 [SMILES: Cc1cc(C(F)(F)F)ccc1C1=C(CN2CCN(c3ccc(C(=O)NS(=O)(=O)c4ccc(NCC5CN(S(C)(=O)=O)CCO5)c([N+](=O)[O-])c4)c(Oc4cnc5[nH]ccc5c4)c3)CC2)CCC(C)(C)C1] |
| 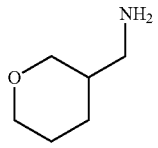 | 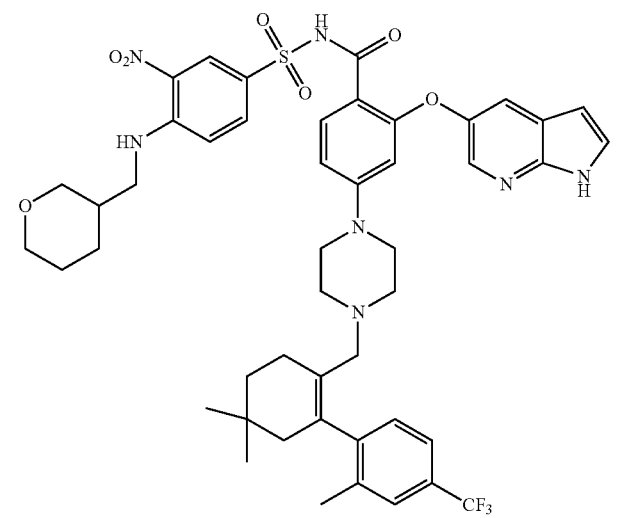 [SMILES: Cc1cc(C(F)(F)F)ccc1C1=C(CN2CCN(c3ccc(C(=O)NS(=O)(=O)c4ccc(NCC5CCCOC5)c([N+](=O)[O-])c4)c(Oc4cnc5[nH]ccc5c4)c3)CC2)CCC(C)(C)C1] |

| Fragment | Compound |
| --- | --- |

| Fragment | Compound |
|---|---|
| 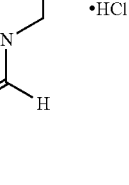 | 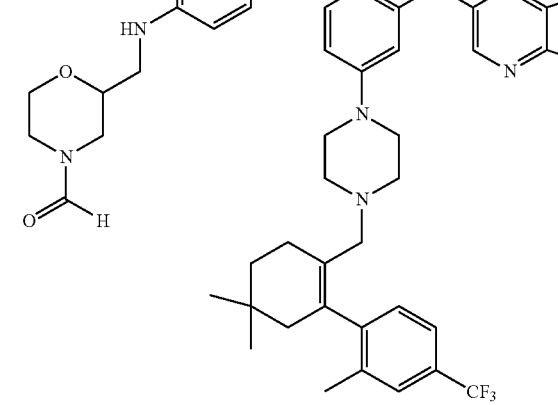 |
| 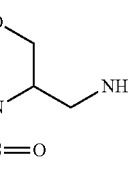 | 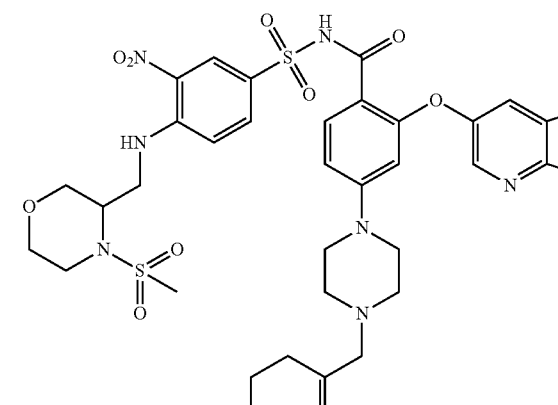 |
|  | 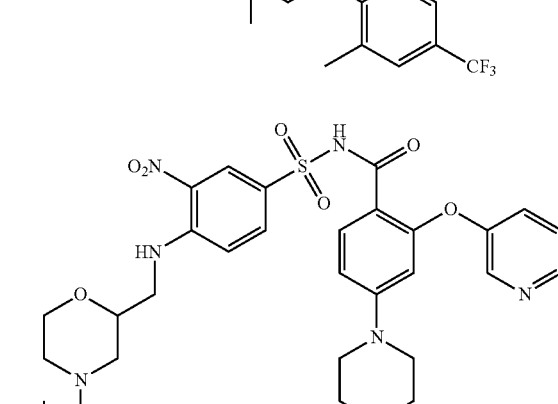 |

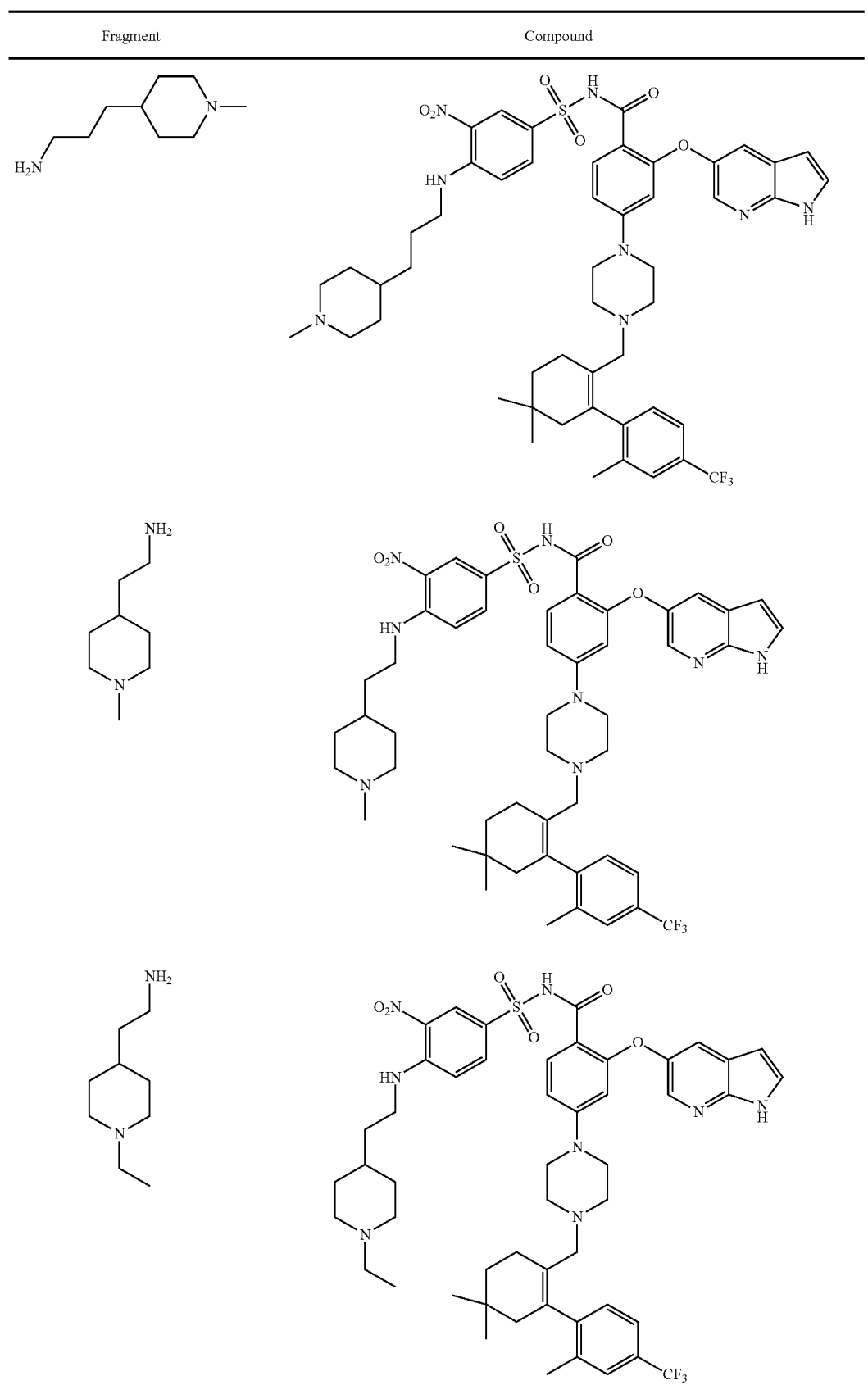

| Fragment | Compound |
|---|---|
| 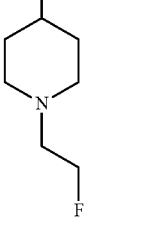 | 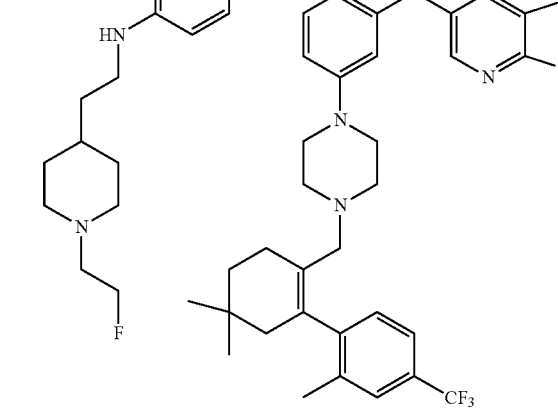 |
| 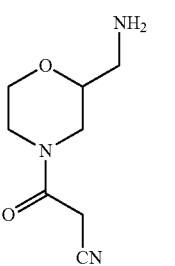 [SMILES: N#CCC(=O)N1CCOC(CN)C1] | 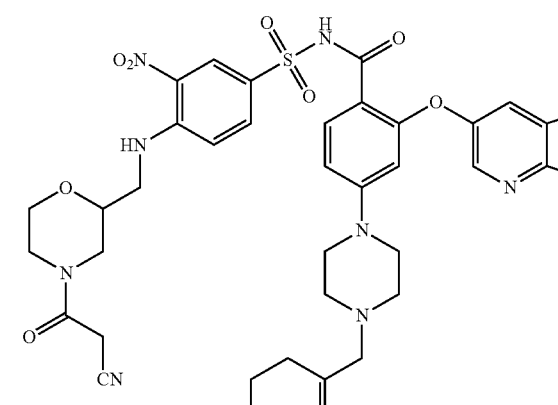 |
| 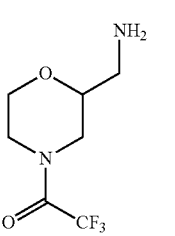 | 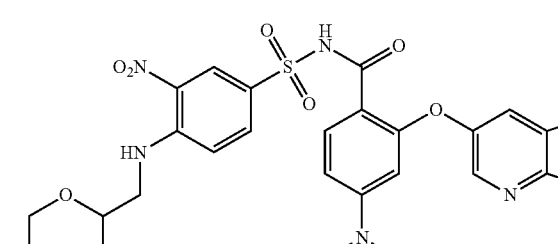 |

-continued
| Fragment | Compound |
|---|---|
| 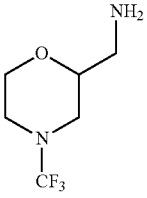 [SMILES: NCC1CN(C(F)(F)F)CCO1] | 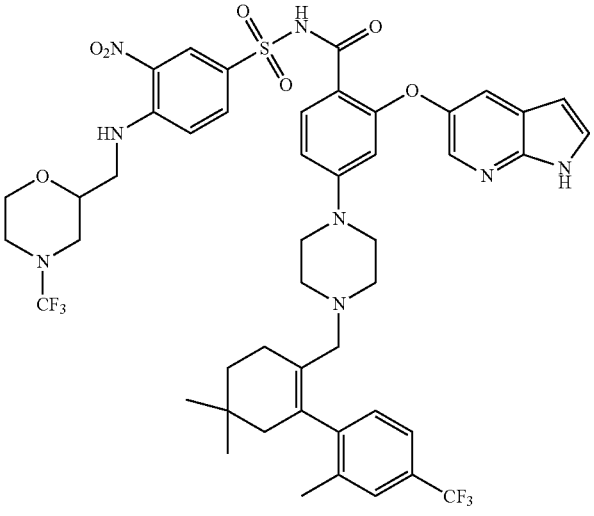 [SMILES: Cc1cc(C(F)(F)F)ccc1C1=C(CN2CCN(c3ccc(C(=O)NS(=O)(=O)c4ccc(NCC5CN(C(F)(F)F)CCO5)c([N+](=O)[O-])c4)c(Oc4cnc5[nH]ccc5c4)c3)CC2)CCC(C)(C)C1] |
| 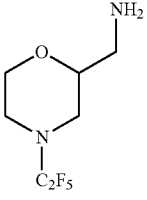 | 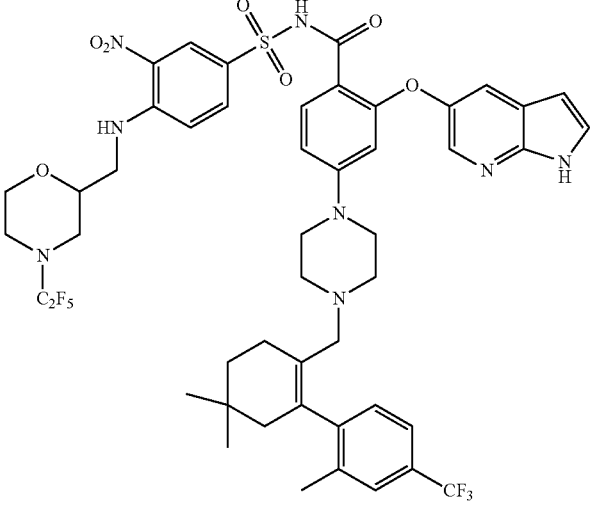 |
| 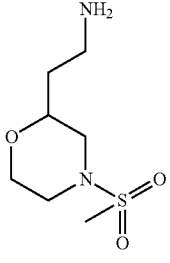 | 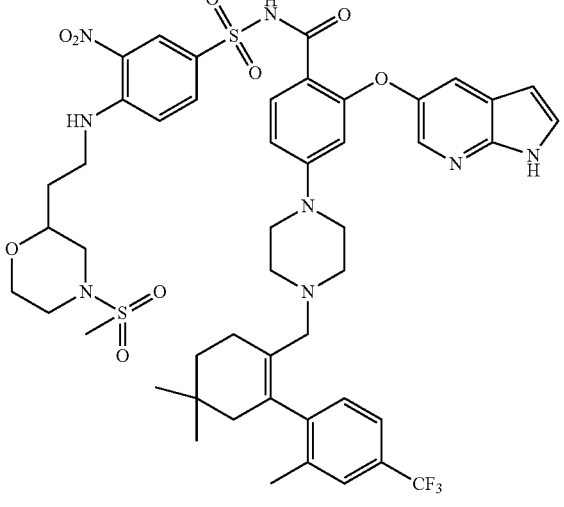 |

-continued

| Fragment | Compound |
|---|---|

| Fragment | Compound |
|---|---|
| 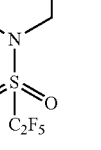 | 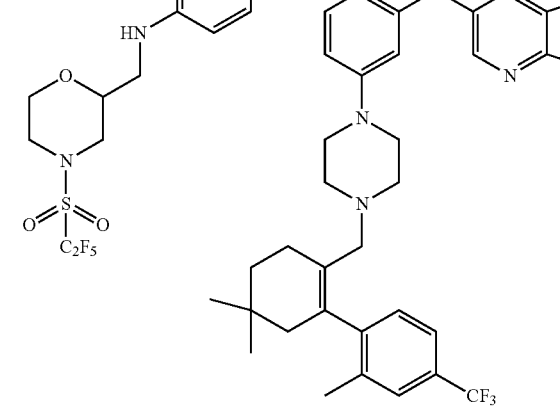 |
| 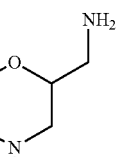 | 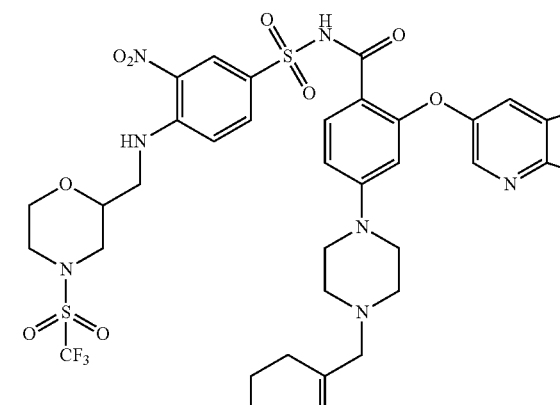 |
| 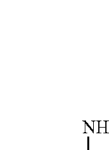 | 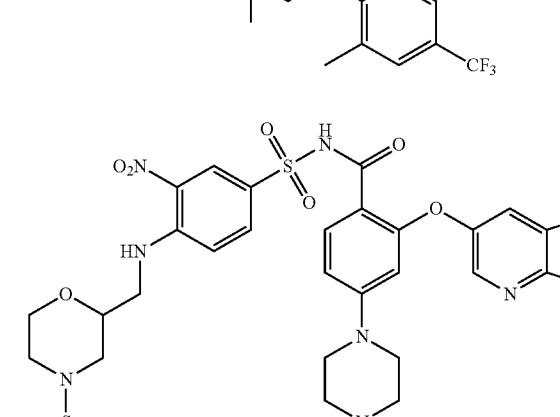 |

-continued

| Fragment | Compound |
|---|---|
| (structure) | (structure) |
| (structure) | (structure) |
| (structure) | (structure) |

| Fragment | Compound |
|---|---|
| (chemical structure) | (chemical structure) |
| (chemical structure) | (chemical structure) |
| (chemical structure) | (chemical structure) |

| Fragment | Compound |
|---|---|
| 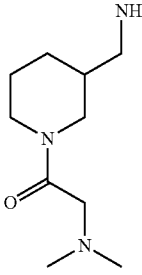 | 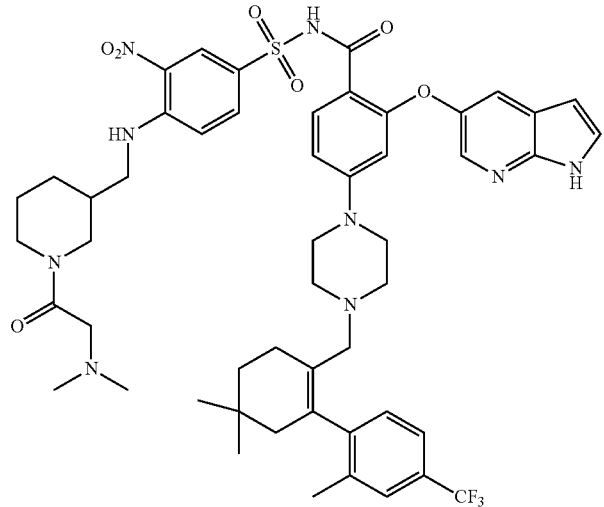 [SMILES: Cc1cc(C(F)(F)F)ccc1C1=C(CN2CCN(c3ccc(C(=O)NS(=O)(=O)c4ccc(NCC5CCCN(C(=O)CN(C)C)C5)c([N+](=O)[O-])c4)c(Oc4cnc5[nH]ccc5c4)c3)CC2)CCC(C)(C)C1] |
| 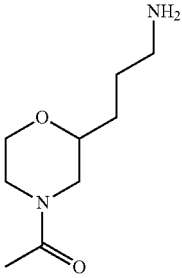 | 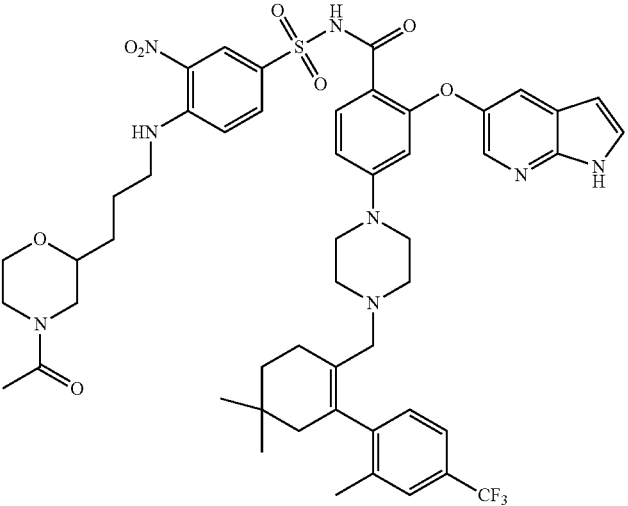 [SMILES: CC(=O)N1CCOC(CCCNc2ccc(S(=O)(=O)NC(=O)c3ccc(N4CCN(CC5=C(c6ccc(C(F)(F)F)cc6C)CC(C)(C)CC5)CC4)cc3Oc3cnc4[nH]ccc4c3)cc2[N+](=O)[O-])C1] |
| 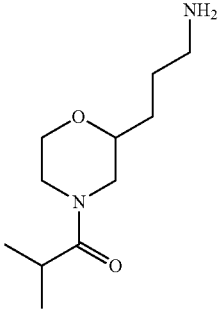 | 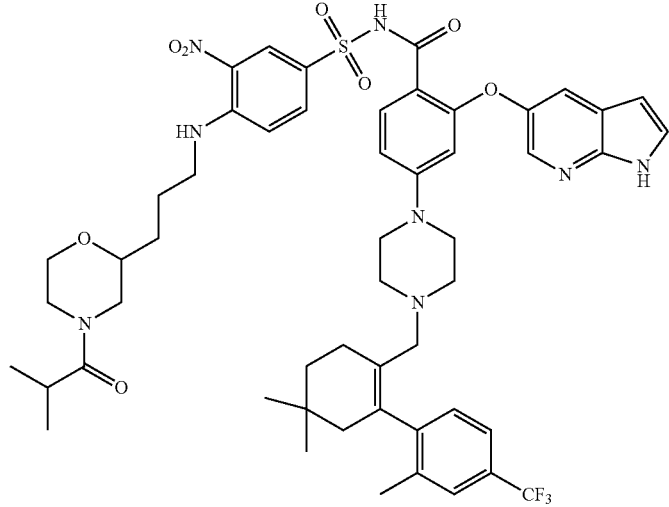 [SMILES: Cc1cc(C(F)(F)F)ccc1C1=C(CN2CCN(c3ccc(C(=O)NS(=O)(=O)c4ccc(NCCCC5CN(C(=O)C(C)C)CCO5)c([N+](=O)[O-])c4)c(Oc4cnc5[nH]ccc5c4)c3)CC2)CCC(C)(C)C1] |

| Fragment | Compound |
|---|---|
| (structure) | (structure) |
| (structure) | (structure) |
| (structure) | (structure) |

| Fragment | Compound |
|---|---|
| | |

| Fragment | Compound |
|---|---|

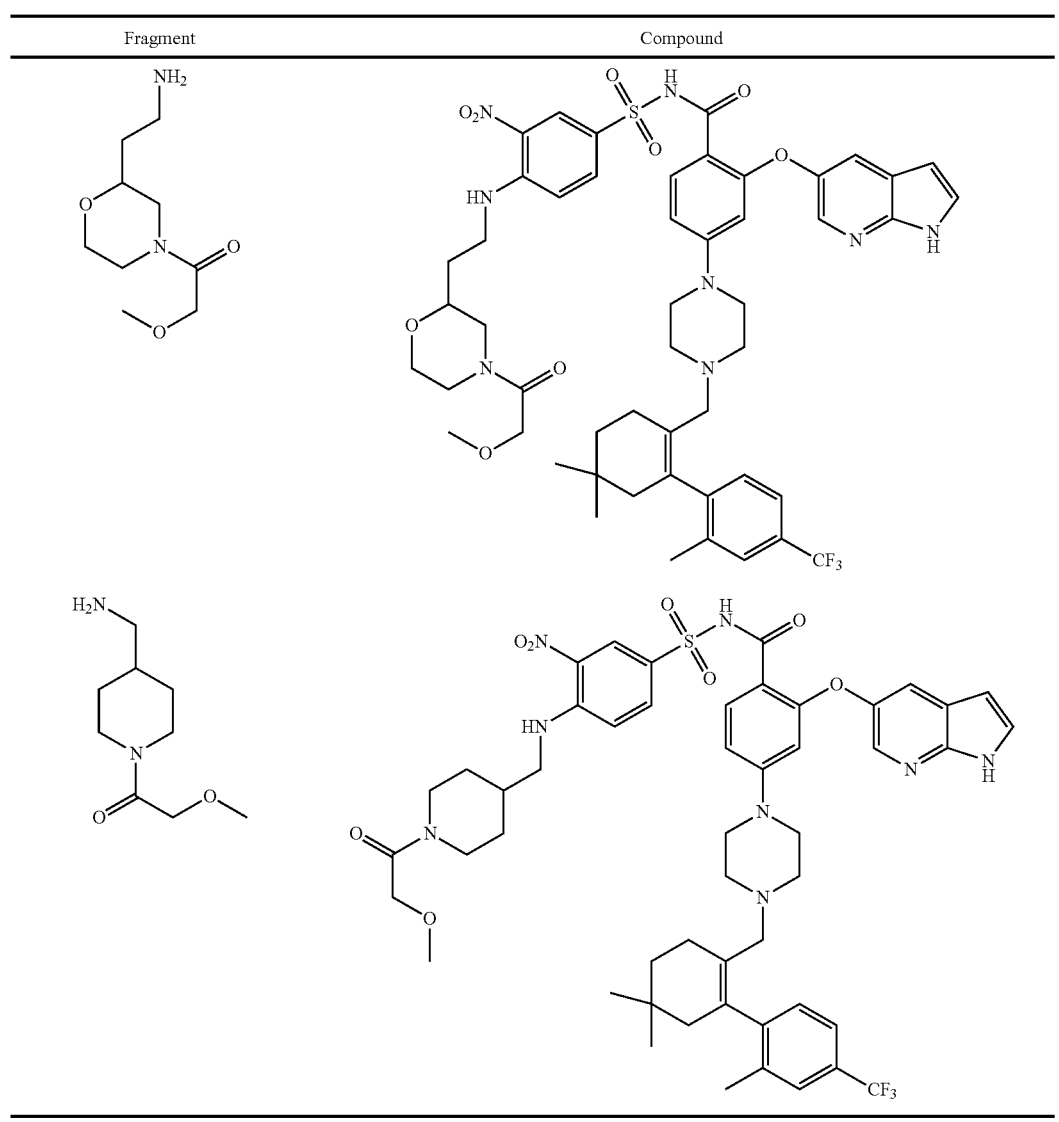

Experimental Example 1: Inhibitory Effects of the Compounds Disclosed Herein on Proliferation of RS4;11 Human Acute Lymphocytic Leukemia Cells RS4;11 cells (from ATCC) in logarithmic growth phase and good cell condition were added to a centrifuge tube and centrifuged at 1500 rpm for 3 min in a low speed centrifuge. The supernatant was discarded, and 5 mL of complete medium (RPMI basic medium+10% FBS) was added using a pipette for cell resuspension. The cells were counted using a cell counter, diluted with complete medium to a cell density of $2\times10^5$ cells/mL, and an equivalent amount of RPMI basic medium was added to adjust the serum concentration to 5% and the cell density to $1\times10^5$ cells/mL for plate seeding. The cells were seeded on a 96-well plate at 100 μL/well using a pipettor, and incubated in an incubator at 37° C., 5% $CO_2$ with saturated humidity. After 24 h of incubation, compounds were loaded using a nanoliter pipettor, 2 duplicate wells were set for each concentration, and cells without compound were used as negative controls. After 72 h, CCK-8 was added at 10 μL/well for incubation for 4 h, then absorbance was measured at 450 nm with an Envision plate reader, and inhibition rate was calculated. Inhibition rate (%)=(mean value of negative control group−mean value of experimental group)/(mean value of negative control group−mean value of blank group)×100%. A dose-response curve was fitted by four-parameter analysis, with the logarithm of compound concentration serving as abscissa and inhibition rate serving as ordinate, so that $IC_{50}$ was calculated (Table 1).

TABLE 1

Inhibitory effects of the compounds disclosed herein on proliferation of RS4;11 cells

| Compound | RS4;11 cells $IC_{50}$(nM) |
|---|---|
| 1-1 | 3.9 |
| 2-1 | 4.2 |
| 3-1 | 1.9 |
| 4-1 | 5.4 |
| 18-1 | 5.5 |
| 19-1 | 3.4 |
| 21-1 | 5.5 |

TABLE 1-continued

Inhibitory effects of the compounds disclosed
herein on proliferation of RS4;11 cells

| Compound | RS4;11 cells IC$_{50}$(nM) |
|---|---|
| 22-1 | 2.2 |
| 23-1 | 2.5 |

Experimental Example 2: Inhibitory Activity for In Vitro Protein Binding 2.1 Screening on Inhibitory Activity for BCL-2/BAK Binding 500 nM Tag1-BCL-2 protein stock solution and 20 μM Tag2-BAK protein stock solution were diluted to 5 nM and 120 nM respectively with dilution buffer in kit (name: BCL-2/BAK (BH3) BINDING ASSAY KITS, cat. No.: 63ADK000CB01PEG, from Cisbio). 5 μL of Tag1-BCL-2 protein diluent was added to each well, then test compounds dissolved with DMSO were added to the wells with a nanoliter pipettor, allowing the final compound concentrations to be 200 nM to 0.0488 nM (4-fold gradient for 7 concentrations in total). Blank control wells (without enzyme) and negative control wells (with enzyme, plus vehicle DMSO) were set, and 2 replicate wells were set. Finally, 5 μL of Tag2-BAK protein diluent was added to each well, and the mixture was mixed well by centrifugation and incubated at 25° C. for 15 min. 100× anti-Tag1-Eu$^{3+}$ and 100× anti-Tag2-XL665 were both diluted to 1× working concentration with the detection buffer in the kit. Anti-Tag1-Eu$^{3+}$ and anti-Tag2-XL665 were mixed well in a 1:1 ratio, and the mixture was added to wells at 5 μL/well, and incubated at 25° C. for 2 h or more. The plate was read using a PE Envision multi-functional microplate reader (excitation: 620 nm, emission: 665 nm) and IC$_{50}$ (shown in Table 2) was calculated by four-parameter fitting.

2.2 Screening on Inhibitory Activity for BCL-XL/BAK Binding 300 nM Tag1-BCL-XL protein stock solution and 10 μM Tag2-BAK protein stock solution were diluted to 2 nM and 80 nM respectively with dilution buffer in kit (name: BCL-XL/BAK (BH3) BINDING ASSAY KITS, cat. No.: 63ADK000CB04PEG, from Cisbio). 5 μL of Tag1-BCL-XL protein diluent was added to each well, then different test compounds dissolved with DMSO were added to the wells with a nanoliter pipettor, allowing the final compound concentrations to be 2000 nM to 0.488 nM (4-fold gradient for 7 concentrations in total). Blank control wells (without enzyme) and negative control wells (with enzyme, plus vehicle DMSO) were set, and 2 replicate wells were set. Finally, 5 μL of Tag2-BAK protein diluent was added to each well, and the mixture was mixed well by centrifugation and incubated at 25° C. for 15 min. 100× anti-Tag1-Eu$^{3+}$ and 100× anti-Tag2-XL665 were both diluted to 1× working concentration with the detection buffer in the kit. Anti-Tag1-Eu$^{3+}$ and anti-Tag2-XL665 were mixed well in a 1:1 ratio, and the mixture was added to wells at 5 μL/well, and incubated at 25° C. for 2 h or more. The plate was read using a PE Envision multi-functional microplate reader (excitation: 620 nm, emission: 665 nm) and IC$_{50}$ (shown in Table 2) was calculated by four-parameter fitting.

TABLE 2

Inhibitory activity of compounds for BCL-2/BAK and BCL-XL/BAK bindings

| Compound | BCL-2/BAK IC$_{50}$(nM) | BCL-XL/BAK IC$_{50}$(nM) |
|---|---|---|
| 3-1 | 1.49 | |
| 4-1 | 0.70 | |
| 9-1 | 1.26 | 219.4 |
| 10-1 | 1.10 | 102 |
| 11-1 | 1.79 | |
| 15-1 | 1.53 | 260.5 |
| 16-1 | 2.07 | 143.6 |
| 18-1 | 1.54 | |
| 19-1 | 0.97 | |
| 20-1 | 2.06 | |
| 21-1 | 0.72 | 114.7 |
| 22-1 | 1.31 | 105.5 |
| 23-1 | 1.10 | |

Experimental Example 3: Pharmacodynamics of Compounds in RS4;11 Human Acute Lymphoblastic Leukemia Mouse Subcutaneous Tumor Xenograft Model SPF female NOD/SCID mice (Shanghai Lingchang Biotech Co., Ltd.) were inoculated subcutaneously at the right side armpit with 1×10$^7$ RS4;11 cells (ATCC). When the mean tumor volume reached about 180 mm$^3$, the mice were divided into 3 groups according to the tumor size: vehicle, compound 1-1 (25 mg/kg) and compound 3-1 (25 mg/kg). The day of grouping was determined as d0. On d1, a single intragastric dose at a volume of 10 mL/kg was administered, and the animals were observed.

The calculation formula for tumor volume: Tumor volume (mm$^3$)=½×(a×b$^2$) (where a represents long diameter and b represents short diameter).

Relative tumor proliferation rate (T/C %) refers to the percentage of the relative tumor volume or tumor weight of the treatment and control groups at a certain time point. The calculation formula is as follows: T/C %=T$_{RTV}$/C$_{RTV}$×100% (T$_{RTV}$: mean relative tumor volume (RTV) for treatment group; C$_{RTV}$: mean RTV for vehicle control group; RTV=TV$_t$/TV$_0$, where TV$_0$ is the tumor volume at grouping, TV$_t$ is the tumor volume after treatment).

Tumor growth inhibition rate (TGI %) is calculated according to the following formula: TGI %=(1−T/C)×100%. (T and C are the relative tumor volume (RTV) or tumor weight (TW) at a particular time point for the treatment and control groups, respectively).

The calculation formula for weight change rate (WCR) (%) is: WCR=(Wt$_t$−Wt$_0$)/Wt$_0$×100%, where Wt$_0$ is the body weight of the animal at grouping (i.e., d0), Wt$_t$ is the body weight of the animal at each measurement.

All experimental results are expressed as mean±SD (mean±standard deviation). The relative tumor volume of the treatment group was compared with that of the control group for any significant difference by T tests, wherein p<0.05 indicates a significant difference, and p<0.01 indicates a very significant difference.

The results are shown in Table 3.

TABLE 3

Effect on RS4; 11 human acute lymphoblastic leukemia subcutaneous xenograft tumors

| Groups | Dosage mg/kg | Day 12 after the end of administration | | | | |
|---|---|---|---|---|---|---|
| | | Tumor volume (mm$^3$) (mean ± SD) | Relative tumor volume (mean ± SD) | T/C (%) | TGI (%) | Weight change rate (%) (mean ± SD) |
| Vehicle | | 858 ± 292 | 5.2 ± 2.4 | — | — | 5.27 ± 6.99 |
| Compound 1-1 | 25 | 350 ± 80 | 2.1 ± 0.6* | 40.4 | 59.6 | 8.20 ± 3.58 |
| Compound 3-1 | 25 | 213 ± 93 | 1.3 ± 0.8** | 25.0 | 75.0 | 5.61 ± 3.61 |

Note:
comparison with the control group, where
*denotes p < 0.05 and
**denotes p < 0.01.

The invention claimed is:

1. A compound of formula I, a stereoisomer thereof or a pharmaceutically acceptable salt thereof:

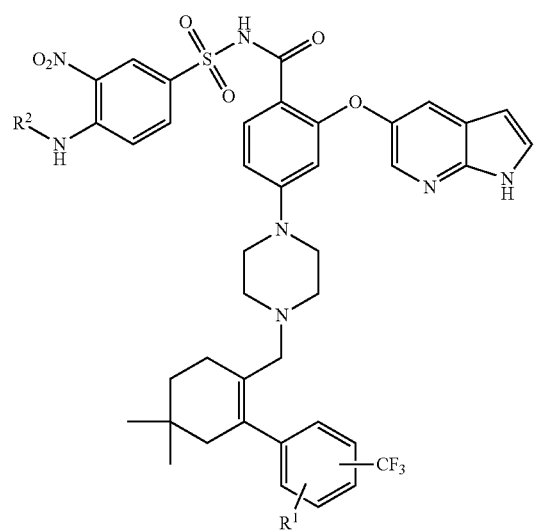

I wherein,

R$^1$ is selected from C$_{1-6}$ alkyl;

R$^2$ is selected from the group consisting of R$^3$ and —C$_{1-6}$ alkylene-R$^3$;

R$^3$ is selected from 5-6 membered heterocycloalkyl, wherein the 5-6 membered heterocycloalkyl is optionally substituted with one or two groups selected from the group consisting of 3-6 membered heterocycloalkyl, C$_{3-6}$ cycloalkyl, —COR$^a$, —SO$_2$R$^b$, and C$_{1-6}$ alkyl optionally substituted with halogen;

R$^a$ or R$^b$ is each independently selected from the group consisting of H, 3-6 membered heterocycloalkyl, C$_{3-6}$ cycloalkyl and C$_{1-6}$ alkyl, wherein the C$_{1-6}$ alkyl is optionally substituted with halogen, —CN, —N(C$_{1-6}$ alkyl)$_2$, —NHC$_{1-6}$ alkyl or —OC$_{1-6}$ alkyl.

2. The compound of formula I, the stereoisomer thereof or the pharmaceutically acceptable salt thereof according to claim 1, wherein the structural fragment

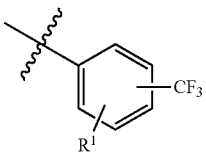

is selected from the group consisting of

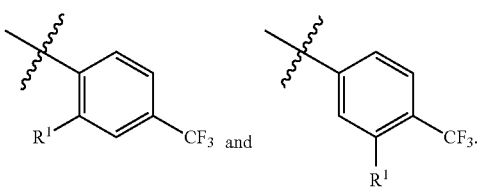

3. The compound of formula I, the stereoisomer thereof or the pharmaceutically acceptable salt thereof according to claim 1, wherein R$^1$ is selected from C$_{1-4}$ alkyl.

4. The compound of formula I, the stereoisomer thereof or the pharmaceutically acceptable salt thereof according to claim 1, wherein R$^2$ is selected from the group consisting of R$^3$ and —(CH$_2$)$_n$—R$^3$, wherein n is selected from the group consisting of 1, 2, 3 and 4.

5. The compound of formula I, the stereoisomer thereof or the pharmaceutically acceptable salt thereof according to claim 4, wherein n is selected from the group consisting of 1, 2 and 3.

6. The compound of formula I, the stereoisomer thereof or the pharmaceutically acceptable salt thereof according to claim 1, wherein R$^3$ is selected from 5-6 membered heterocycloalkyl, and wherein the 5-6 membered heterocycloalkyl is optionally substituted with one or two groups at the ring N atom.

7. The compound of formula I, the stereoisomer thereof or the pharmaceutically acceptable salt thereof according to claim 1, wherein R$^a$ or R$^b$ is each independently selected from the group consisting of H, 3-6 membered heterocycloalkyl, C$_{3-6}$ cycloalkyl and C$_{1-4}$ alkyl, wherein the C$_{1-4}$ alkyl is optionally substituted with halogen, —CN, —N(C$_{1-4}$ alkyl)$_2$, —NHC$_{1-4}$ alkyl or —OC$_{1-4}$ alkyl.

8. The compound of formula I, the stereoisomer thereof or the pharmaceutically acceptable salt thereof according to claim 1, wherein R$^3$ is selected from 5-6 membered heterocycloalkyl, wherein the 5-6 membered heterocycloalkyl is optionally substituted with —C(O)H, —COCH$_3$, —COCH(CH$_3$)$_2$, —COC(CH$_3$)$_3$, —COCF$_3$, —COCH$_2$CN, —COCH$_2$OCH$_3$, —COCH$_2$N(CH$_3$)$_2$, —SO$_2$CH$_3$, —SO$_2$CH$_2$CH$_3$, —SO$_2$CF$_3$, —SO$_2$C$_2$F$_5$, methyl, ethyl, —CF$_3$, —CH$_2$CH$_2$F, —C$_2$F$_5$, tetrahydropyran, monooxacyclobutane, —SO$_2$-cyclopropane, —CO-cyclopropane, —CO-monooxacyclobutane, —SO$_2$-monooxacyclobutane or —SO$_2$-cyclobutane.

9. The compound of formula I, the stereoisomer thereof or the pharmaceutically acceptable salt thereof according to claim 8, wherein R$^3$ is selected from the group consisting of

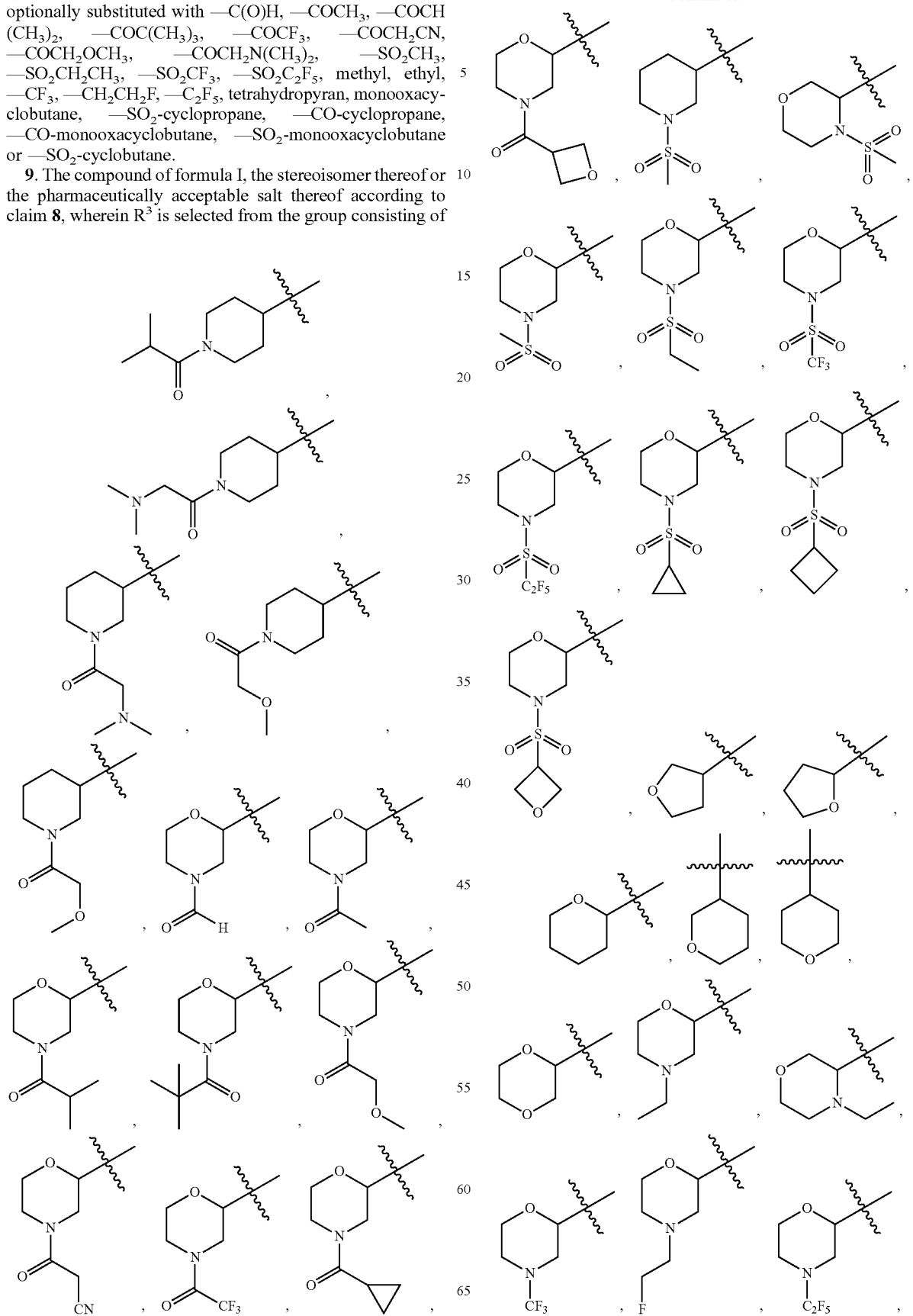

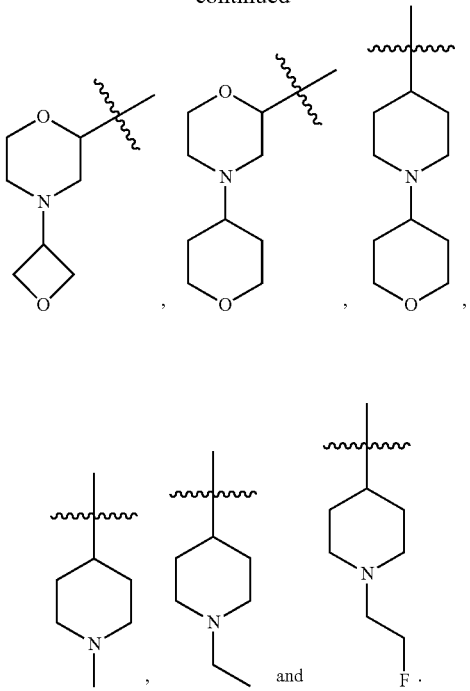

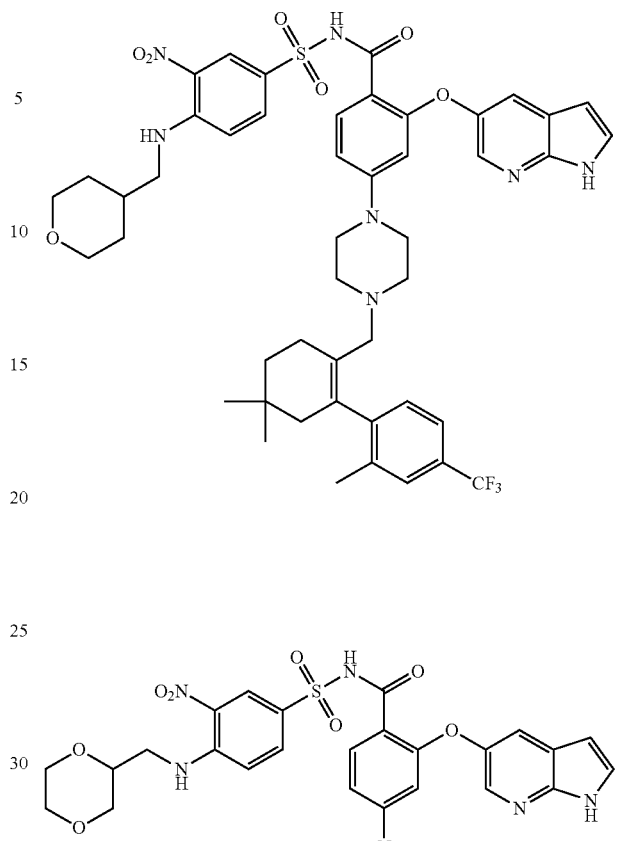

10. The compound of formula I, the stereoisomer thereof or the pharmaceutically acceptable salt thereof according to claim 1, wherein the compound of formula I, the stereoisomer thereof or the pharmaceutically acceptable salt thereof is selected from a compound of formula II, a stereoisomer thereof or a pharmaceutically acceptable salt thereof:

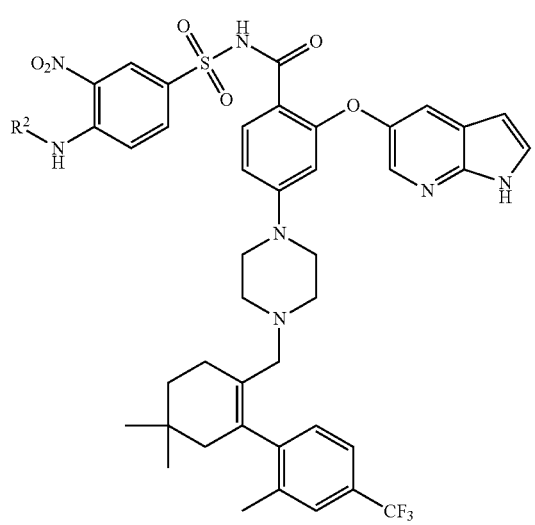

II wherein $R^2$ is as defined in claim 1.

11. The compound of formula I, the stereoisomer thereof or the pharmaceutically acceptable salt thereof according to claim 1, selected from a compound of the following formulas, a stereoisomer thereof or a pharmaceutically acceptable salt thereof:

127
-continued
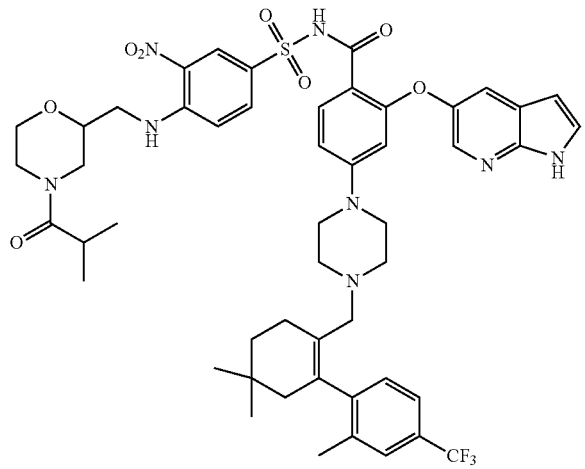
128
-continued
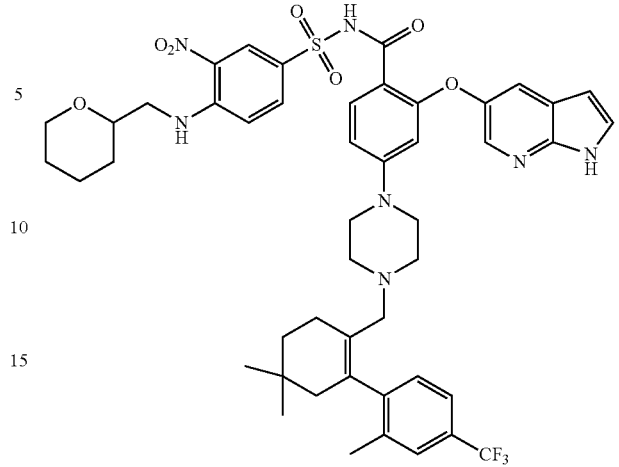
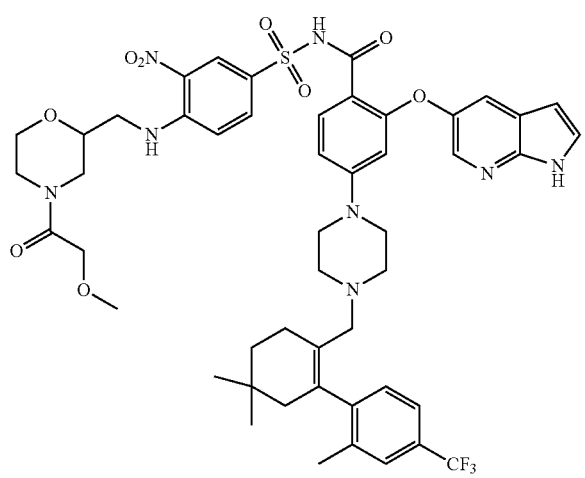
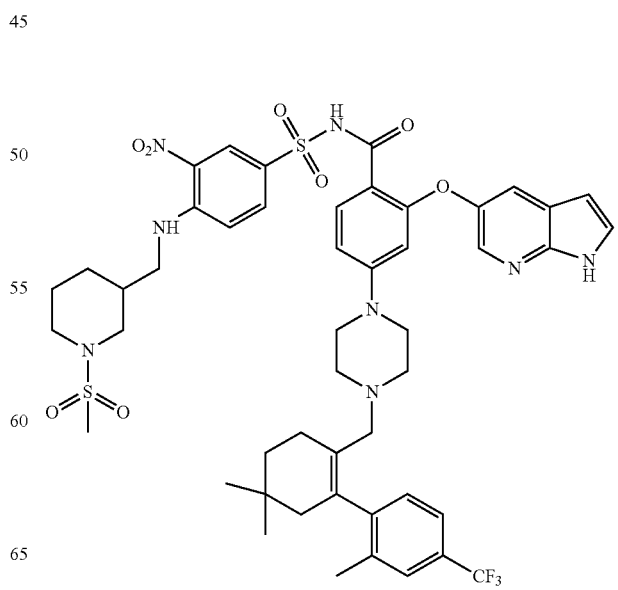

129
-continued
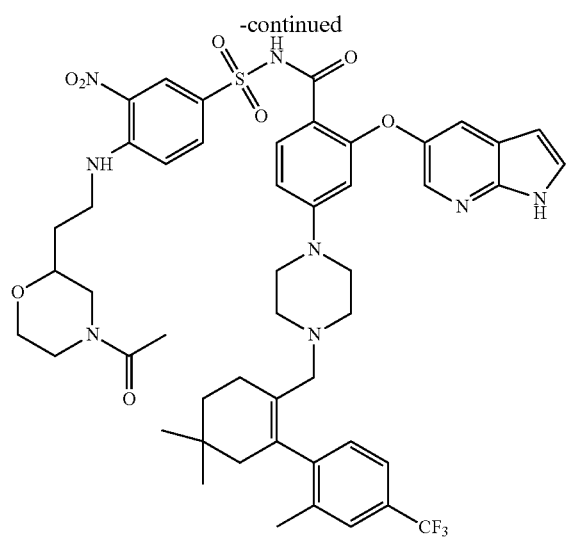
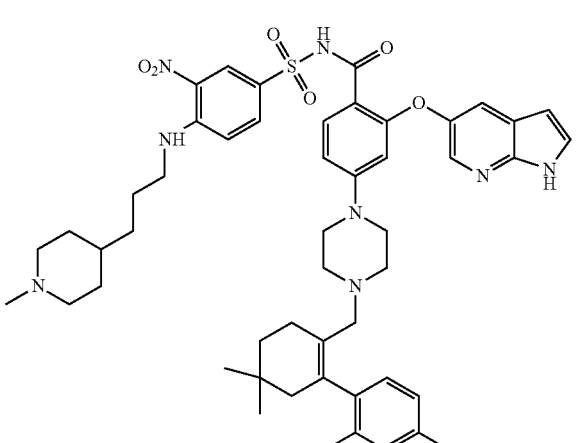
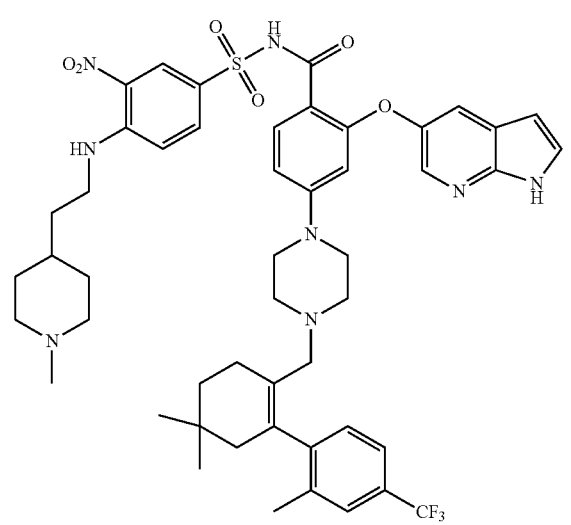
130
-continued
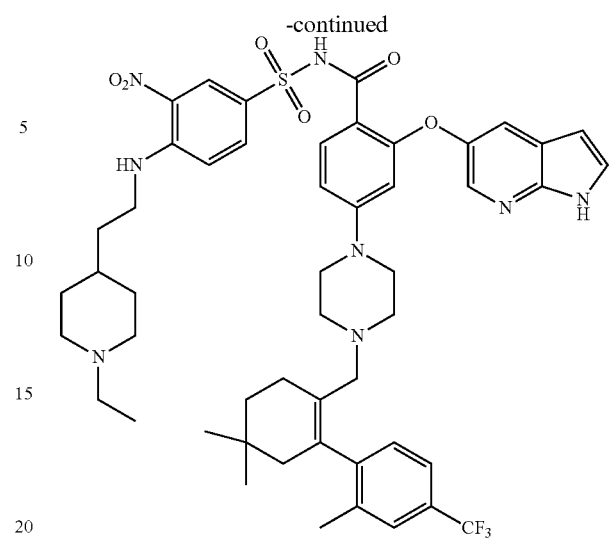
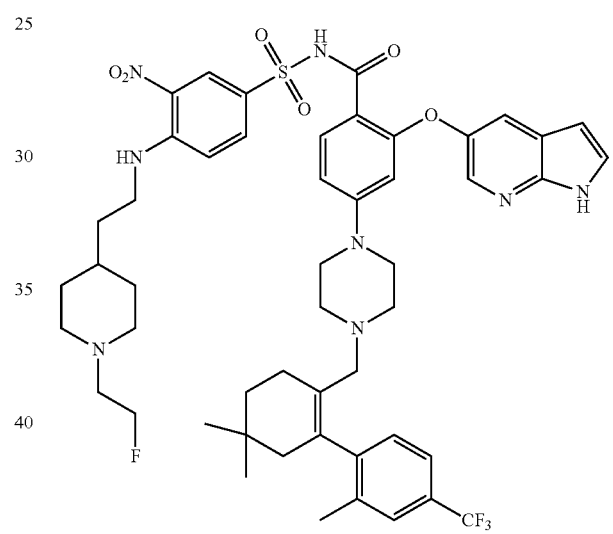
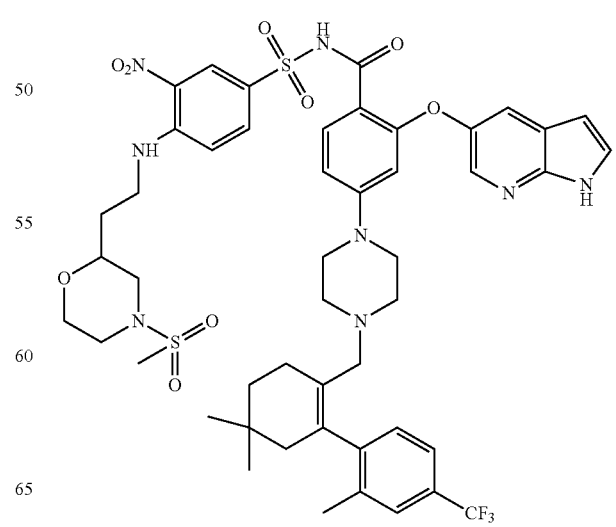

131
-continued
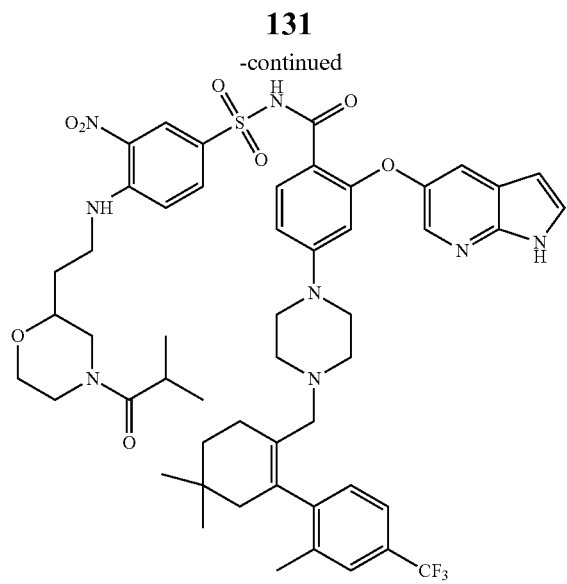
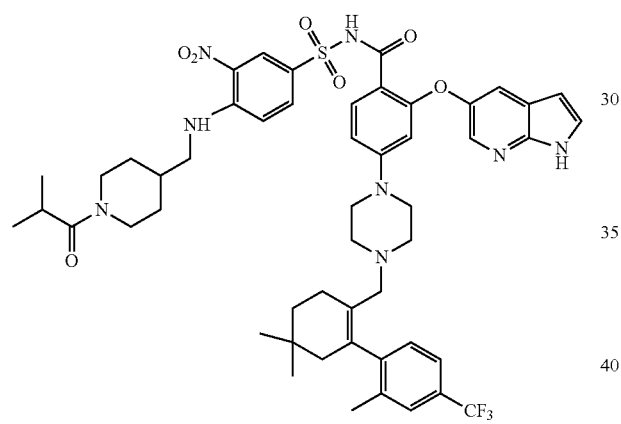
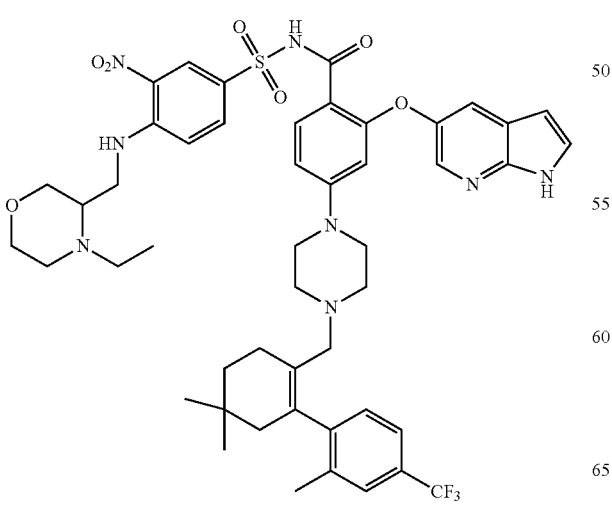
132
-continued
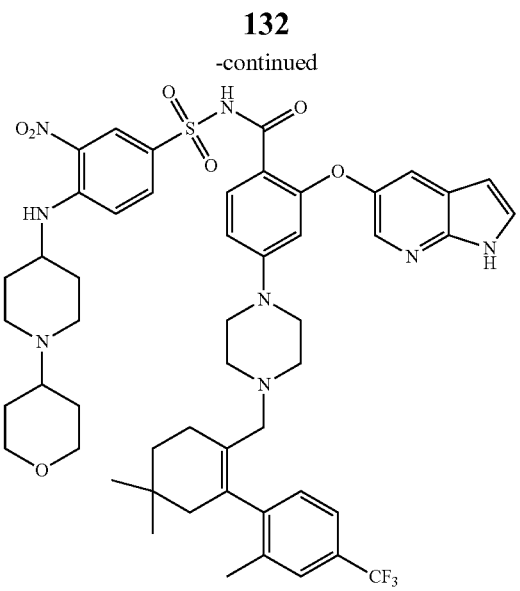
or a compound of the following formula, a stereoisomer thereof or a pharmaceutically acceptable salt thereof:
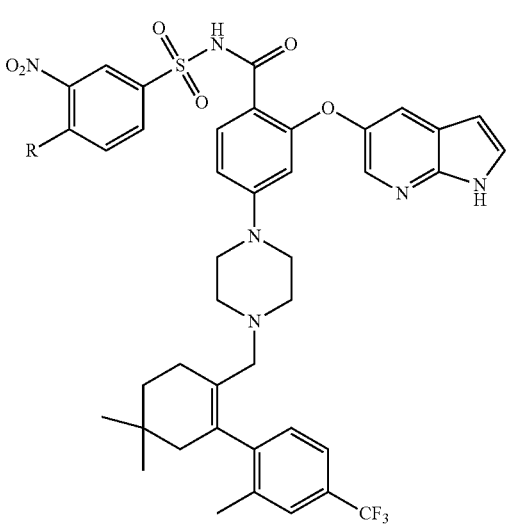
wherein R is independently selected from the group consisting of:
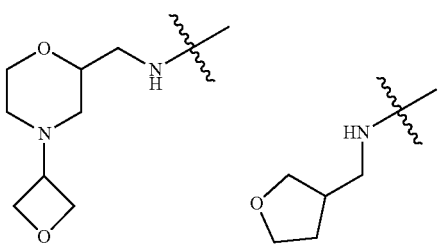

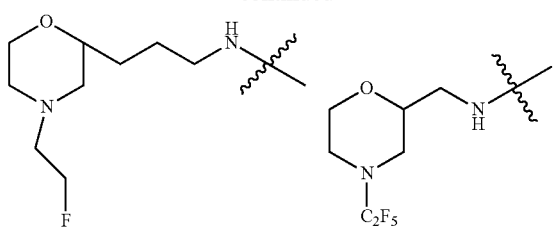
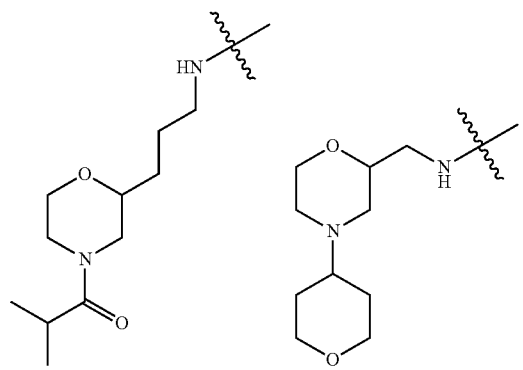
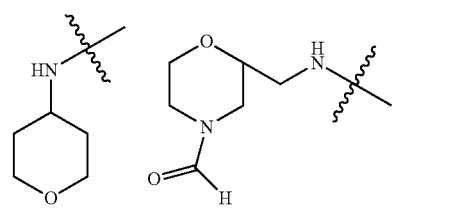
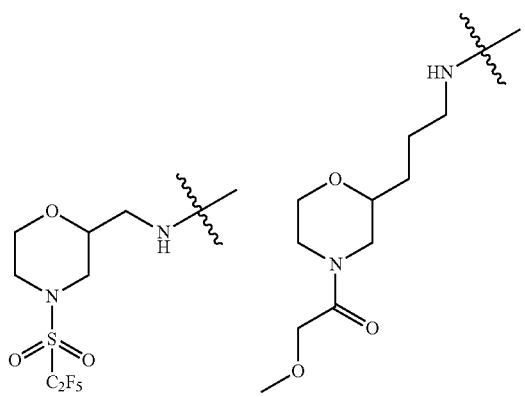
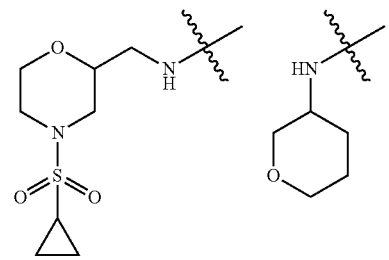
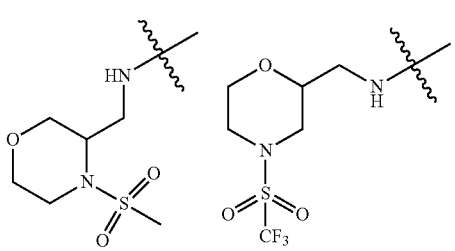
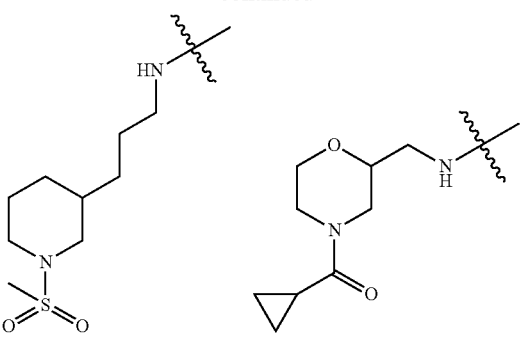
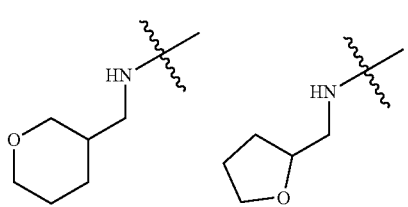
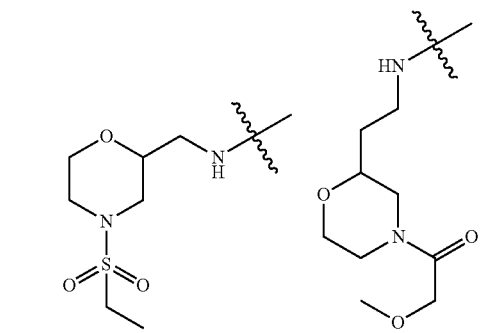
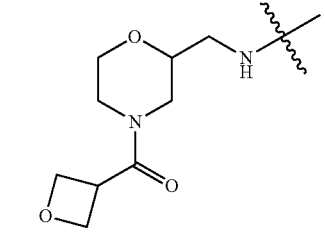
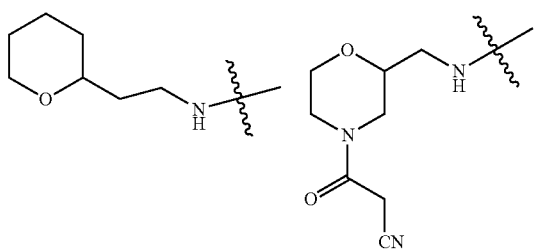
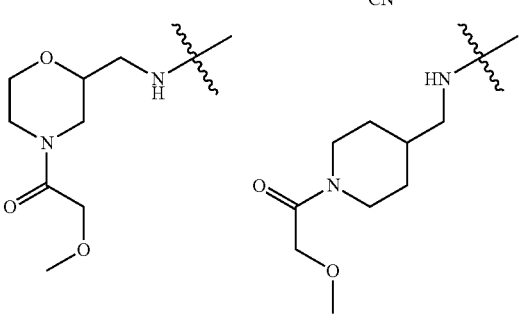

-continued
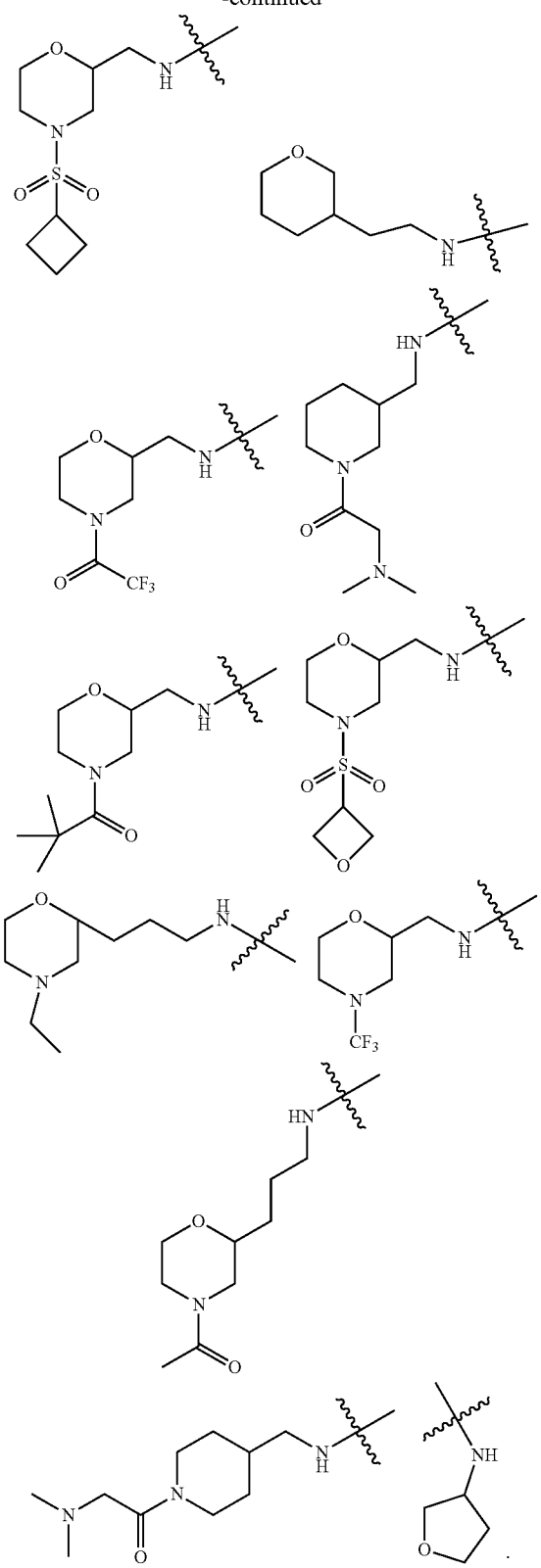
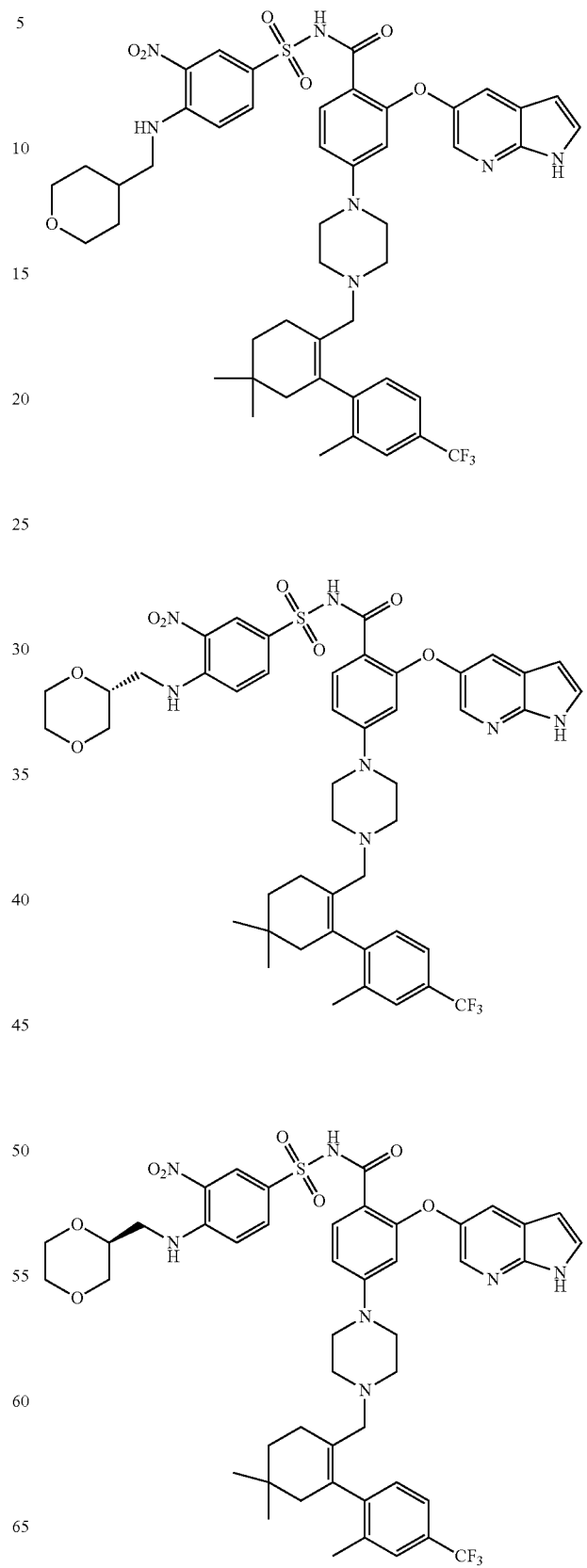
12. The compound, the stereoisomer thereof or the pharmaceutically acceptable salt thereof according to claim 11, wherein the compound, the stereoisomer thereof or the pharmaceutically acceptable salt thereof is selected from the group consisting of the following compounds or pharmaceutically acceptable salts thereof:

137
-continued

138
-continued

139
-continued
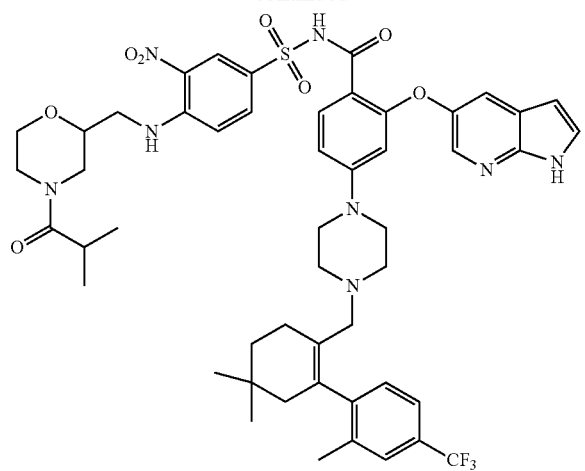
140
-continued
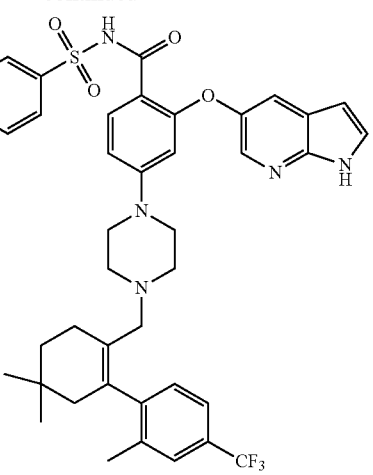
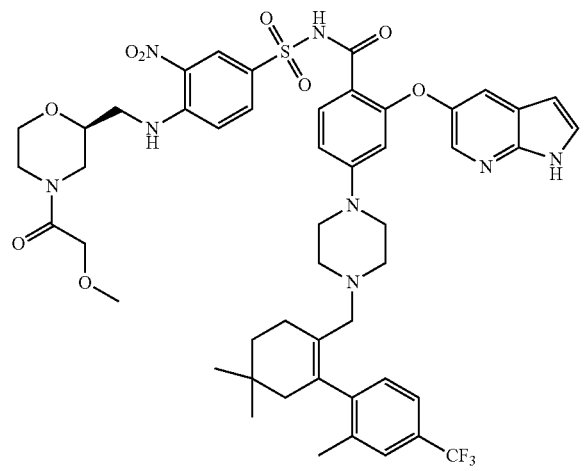
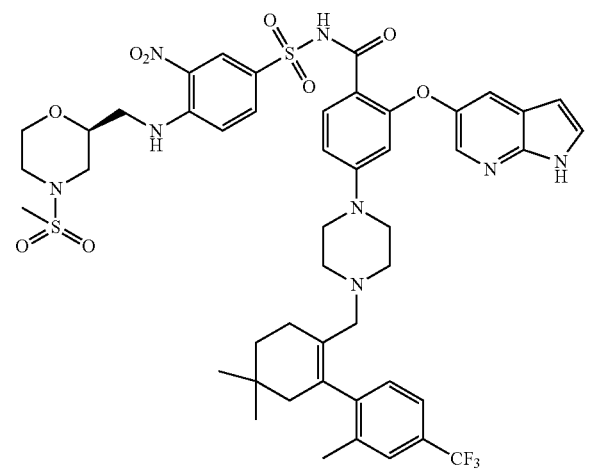

141
-continued
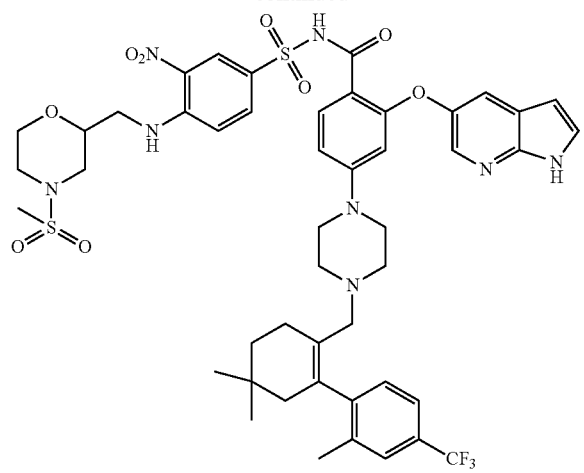
142
-continued
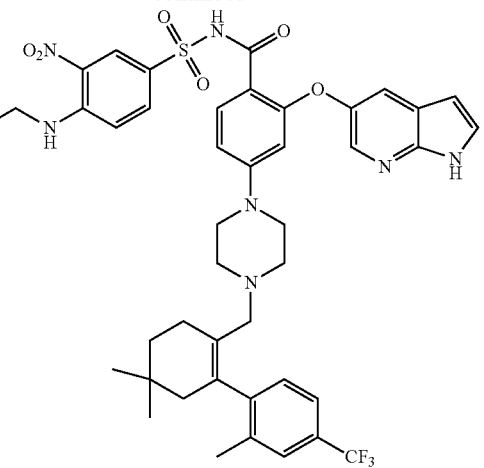
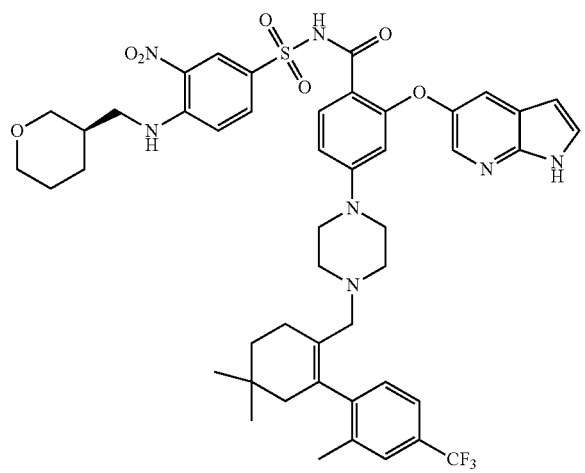
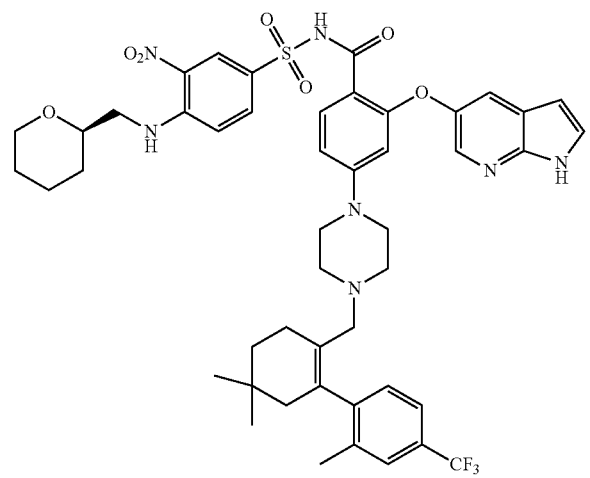

143
-continued
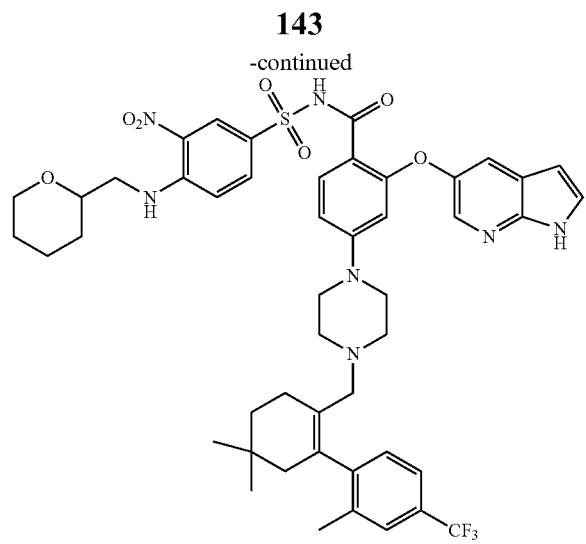
144
-continued
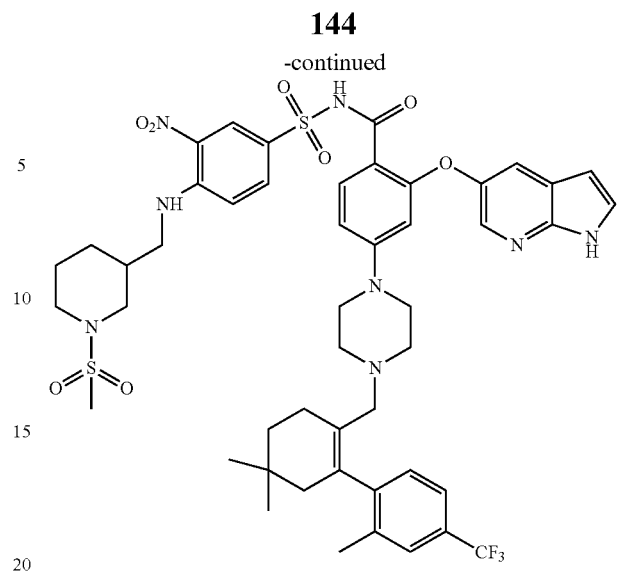
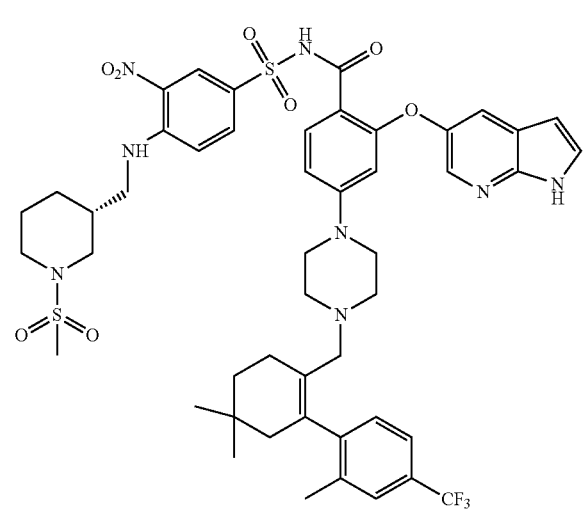
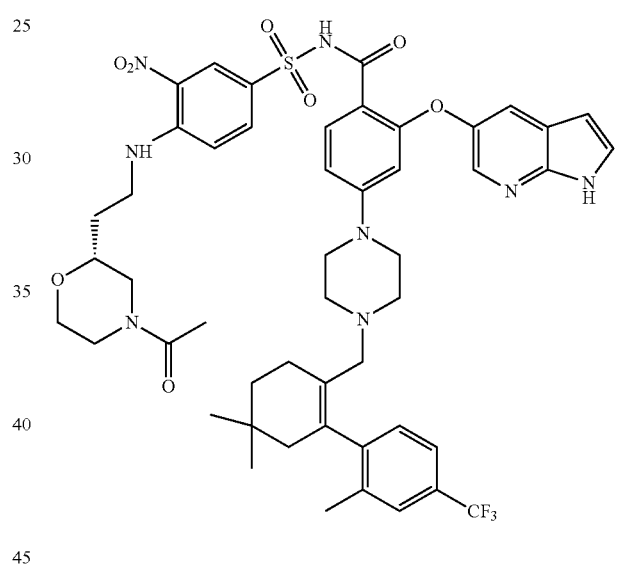
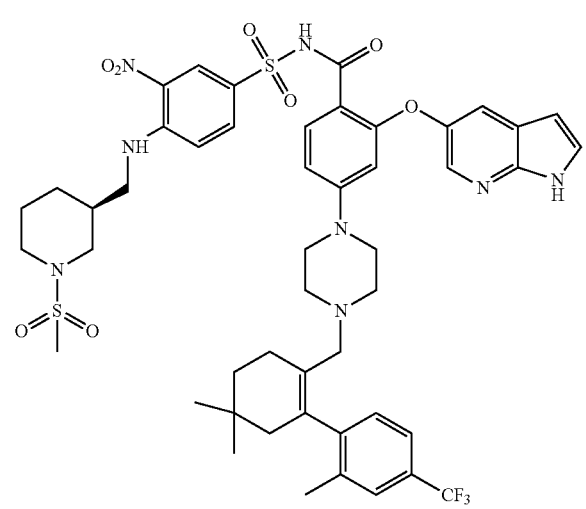
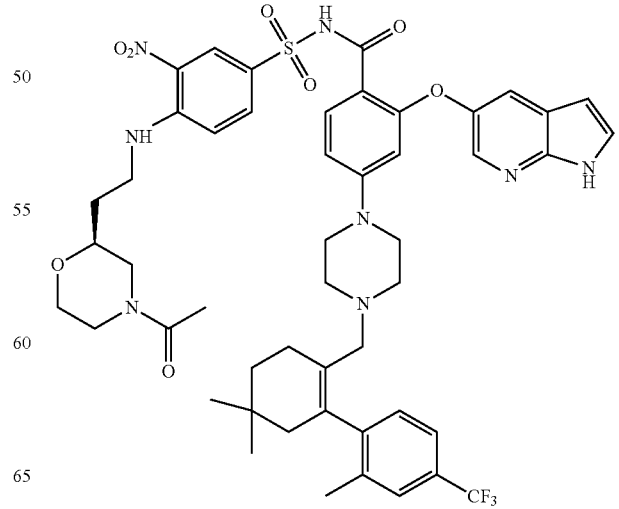

145
-continued
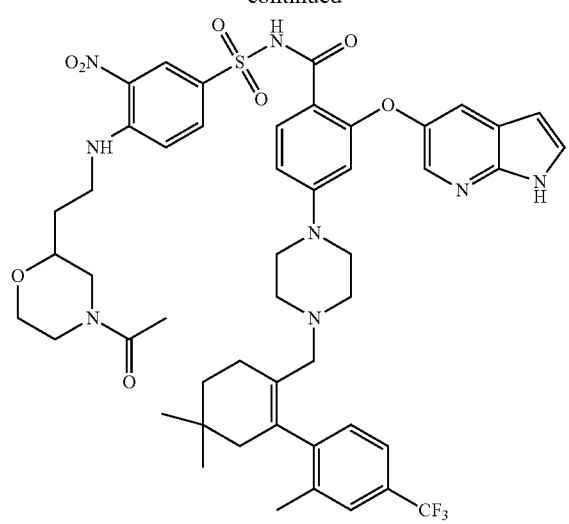
146
-continued
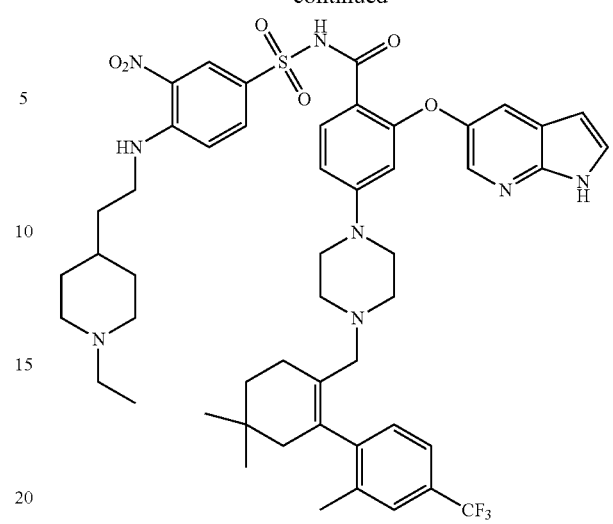
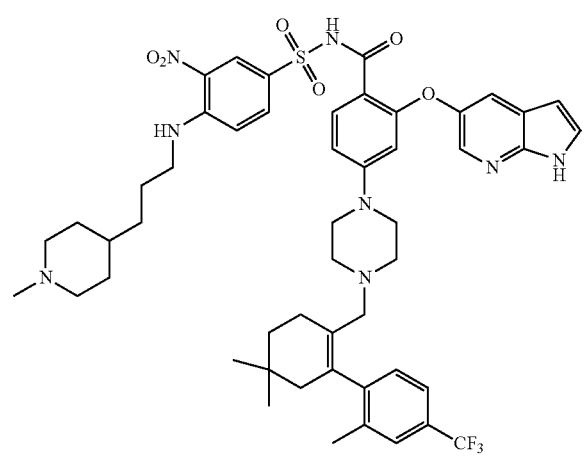
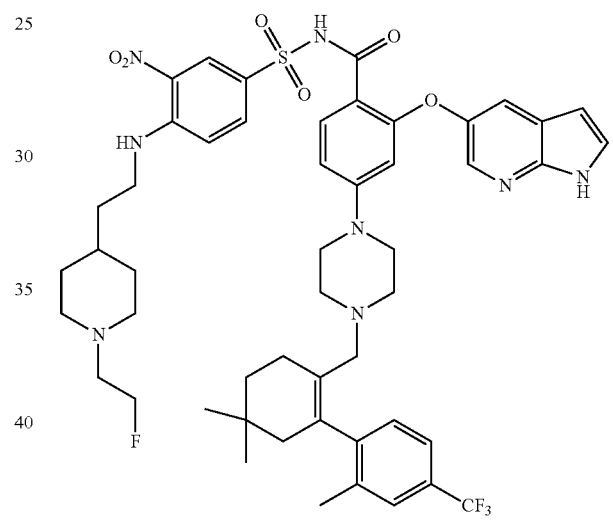
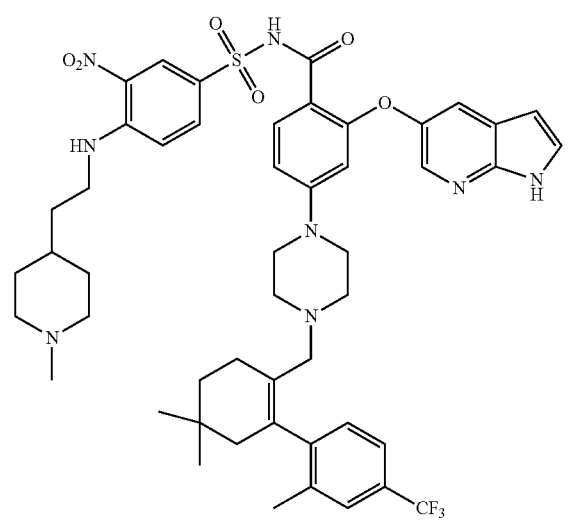
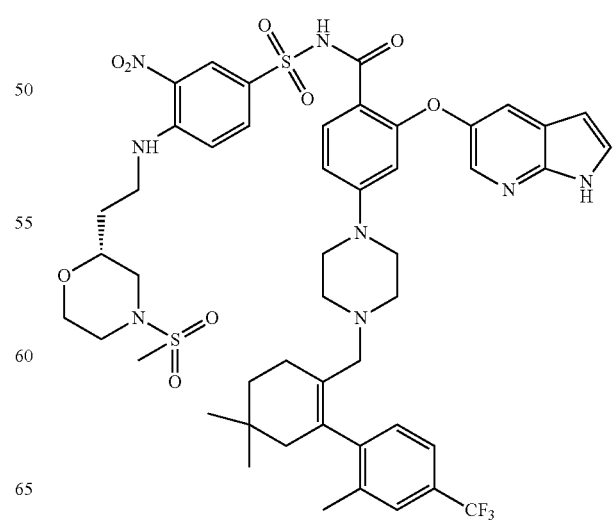

147
-continued
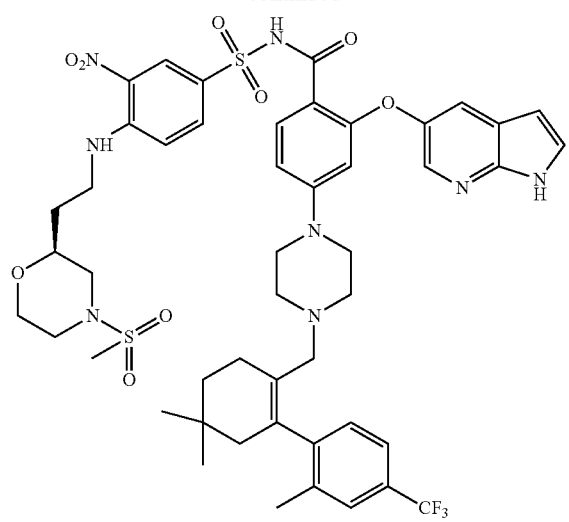
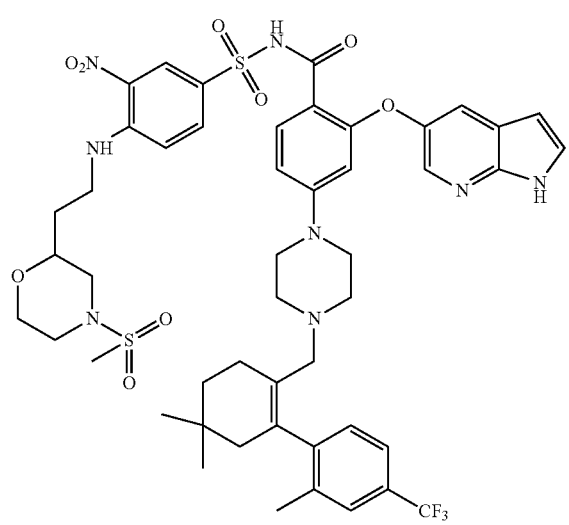
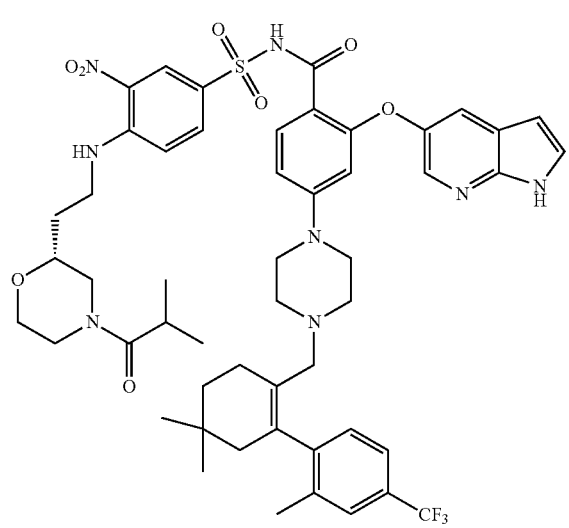
148
-continued
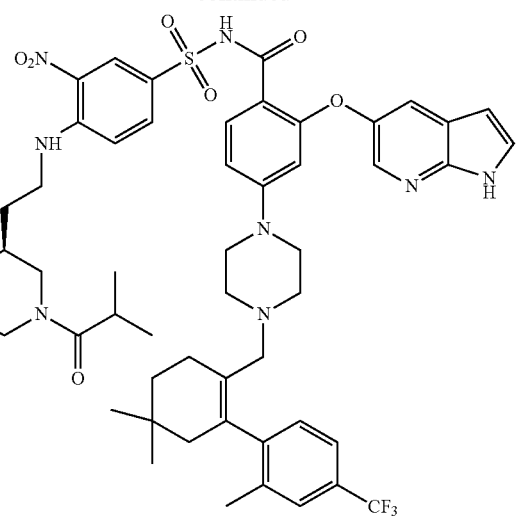
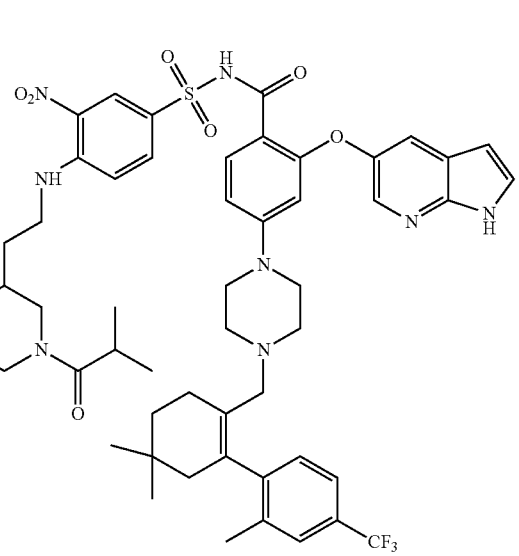
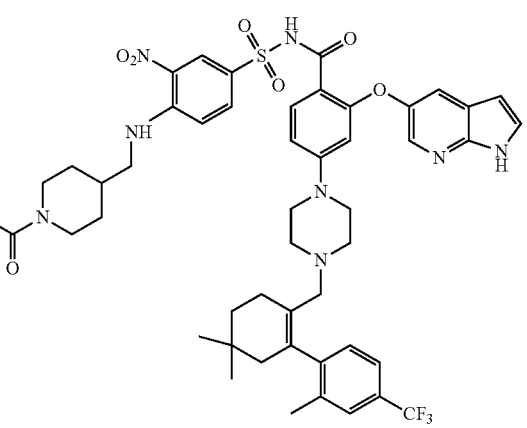

149
-continued
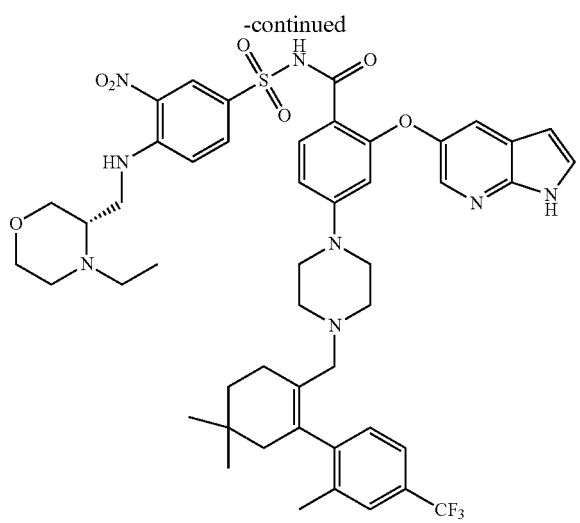
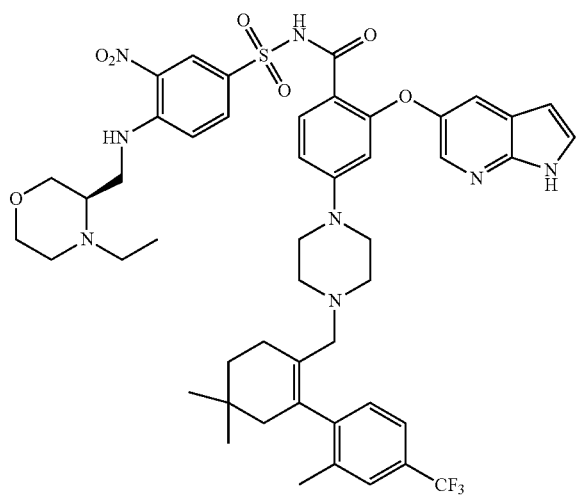
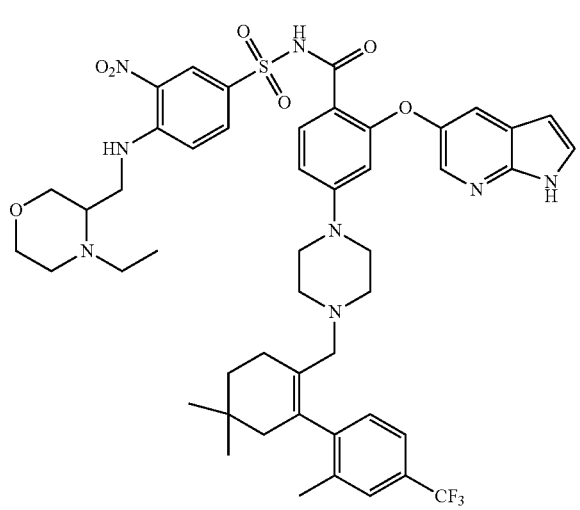
150
-continued
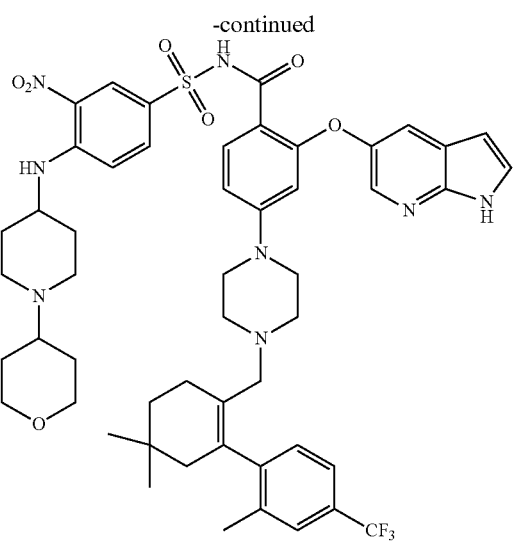
or the following compounds or pharmaceutically acceptable salts thereof:
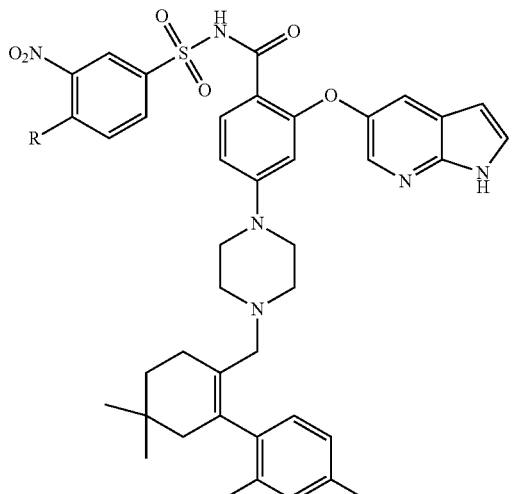
wherein R is independently selected from the group consisting of:
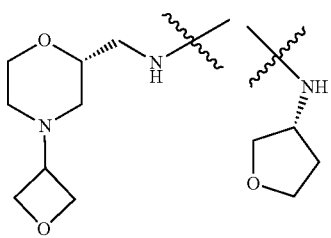

151
-continued
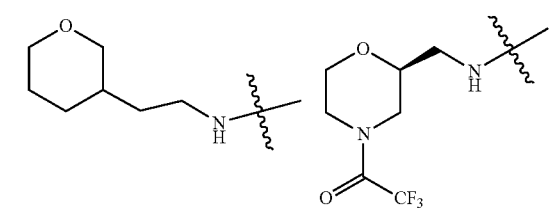
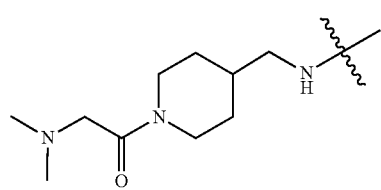
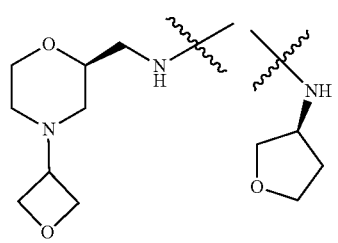
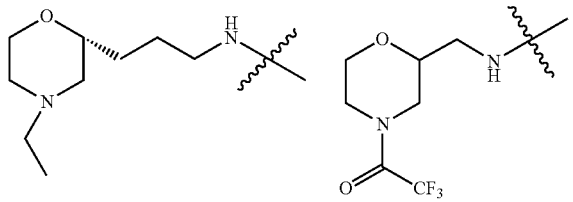
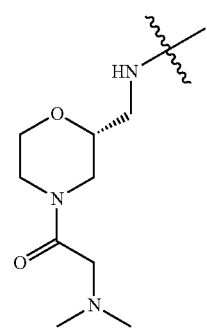
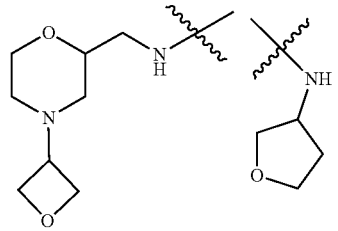
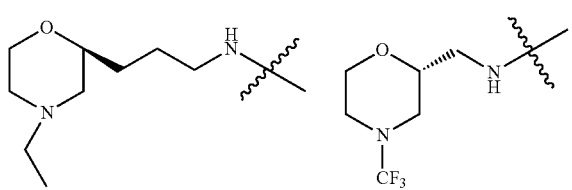
152
-continued
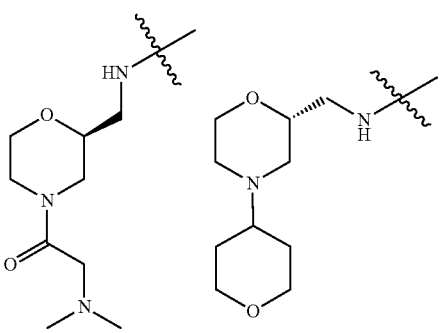
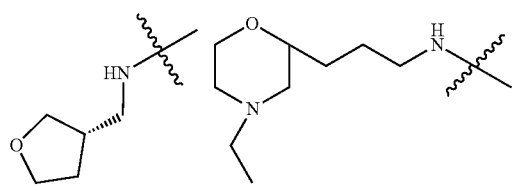
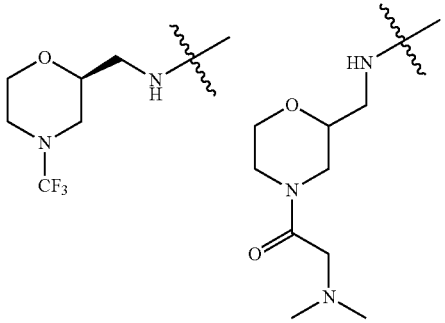
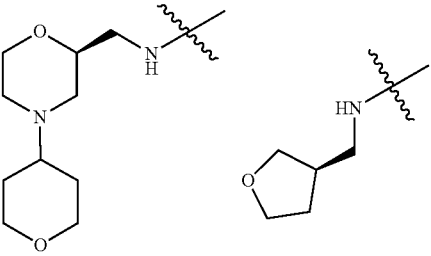
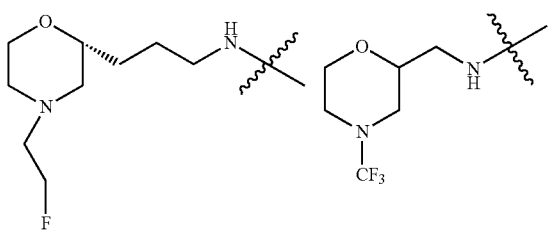
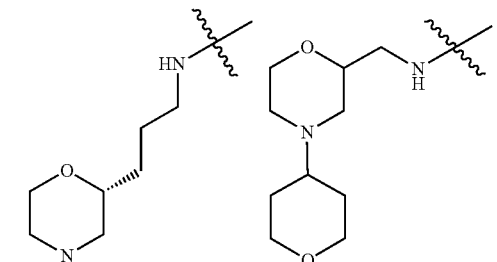

153
-continued
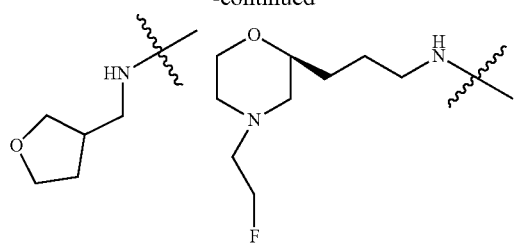
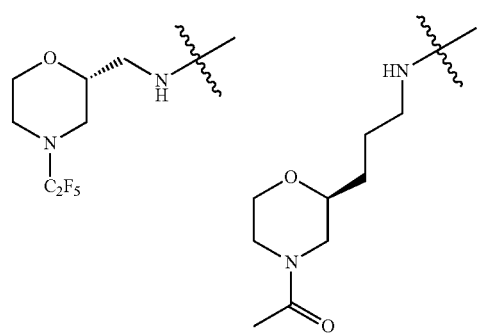
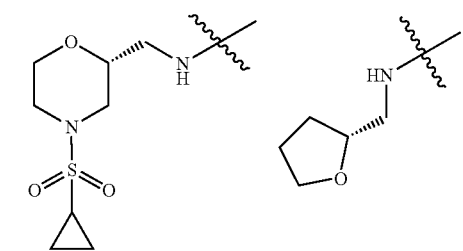
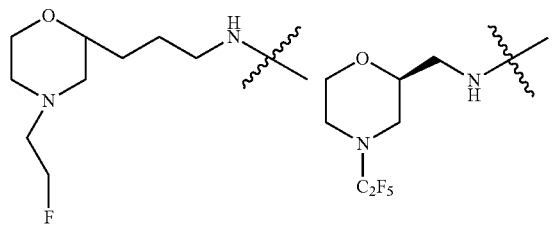
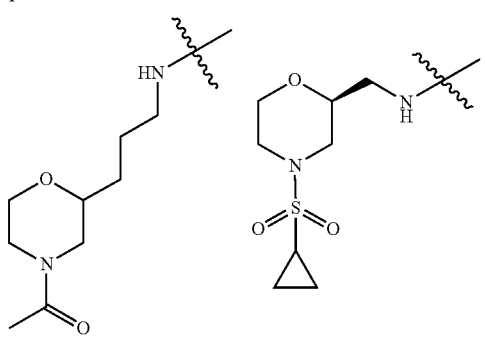
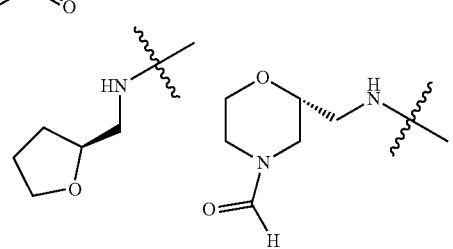
154
-continued
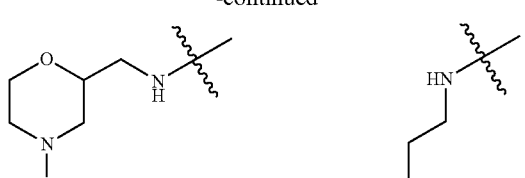
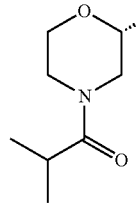
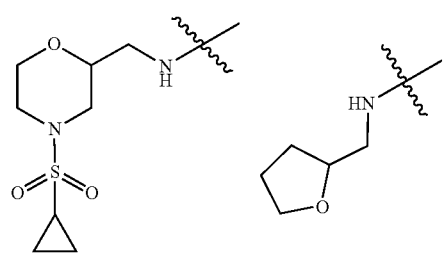
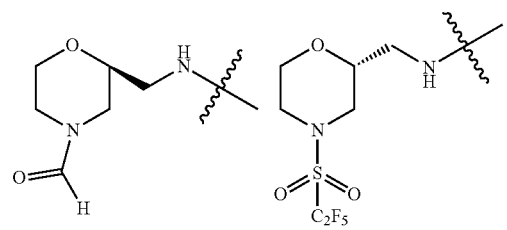
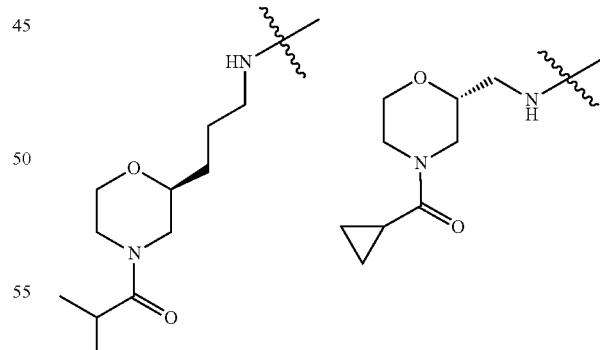
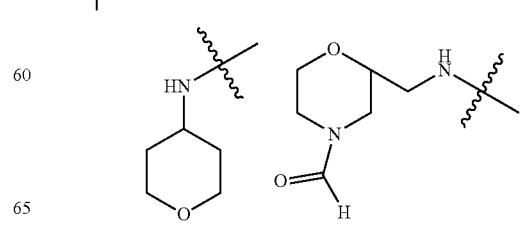

155
-continued
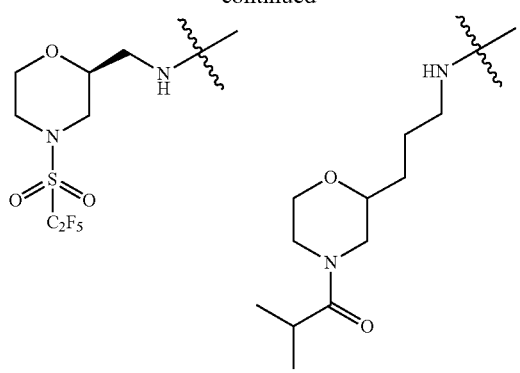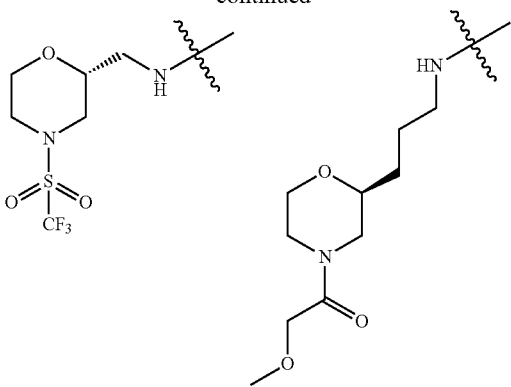
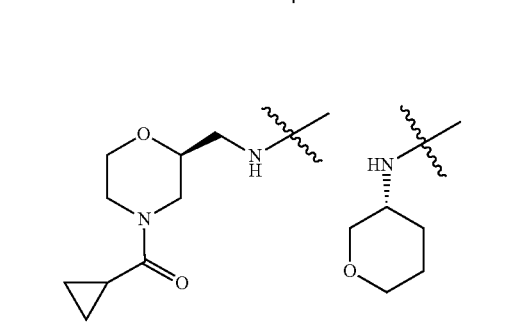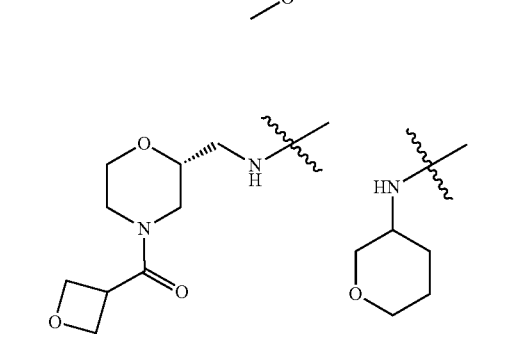
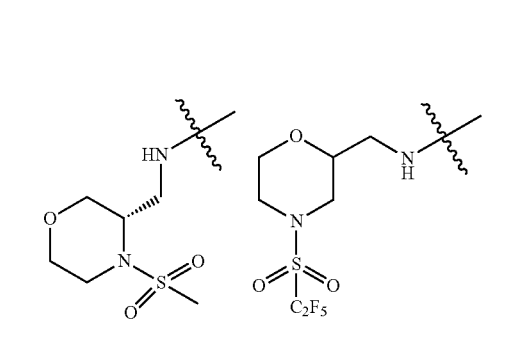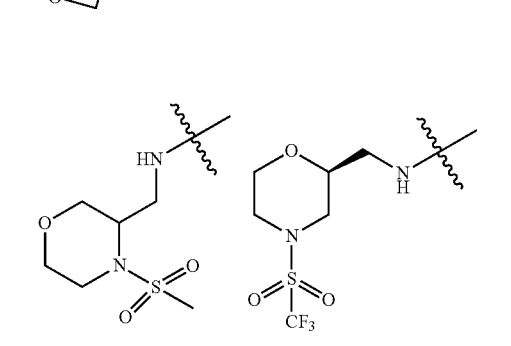
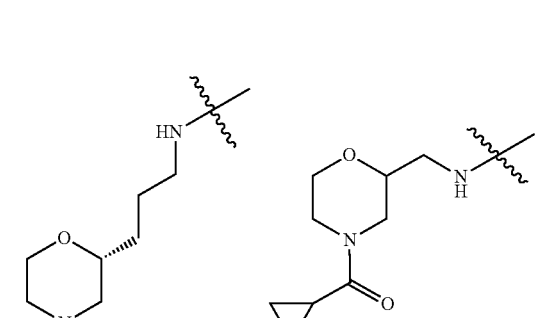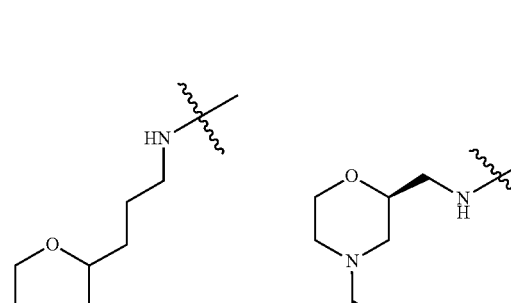
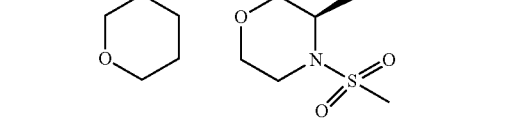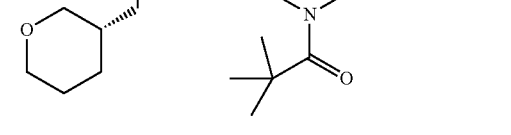
156
-continued 157
-continued
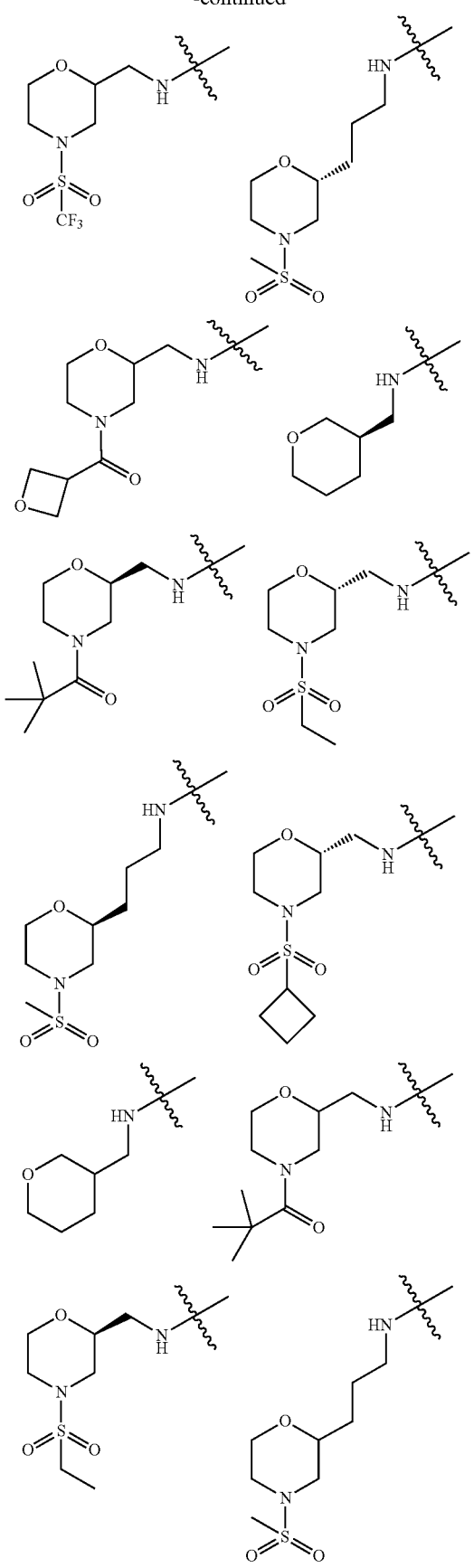
158
-continued
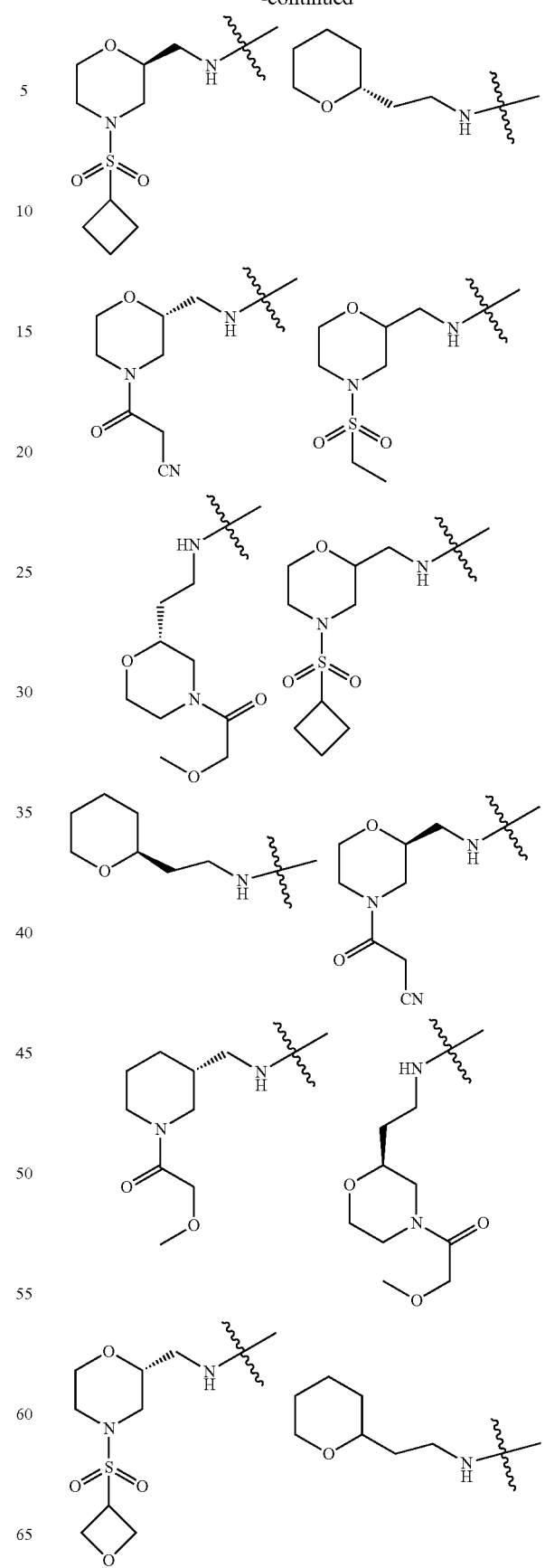

-continued

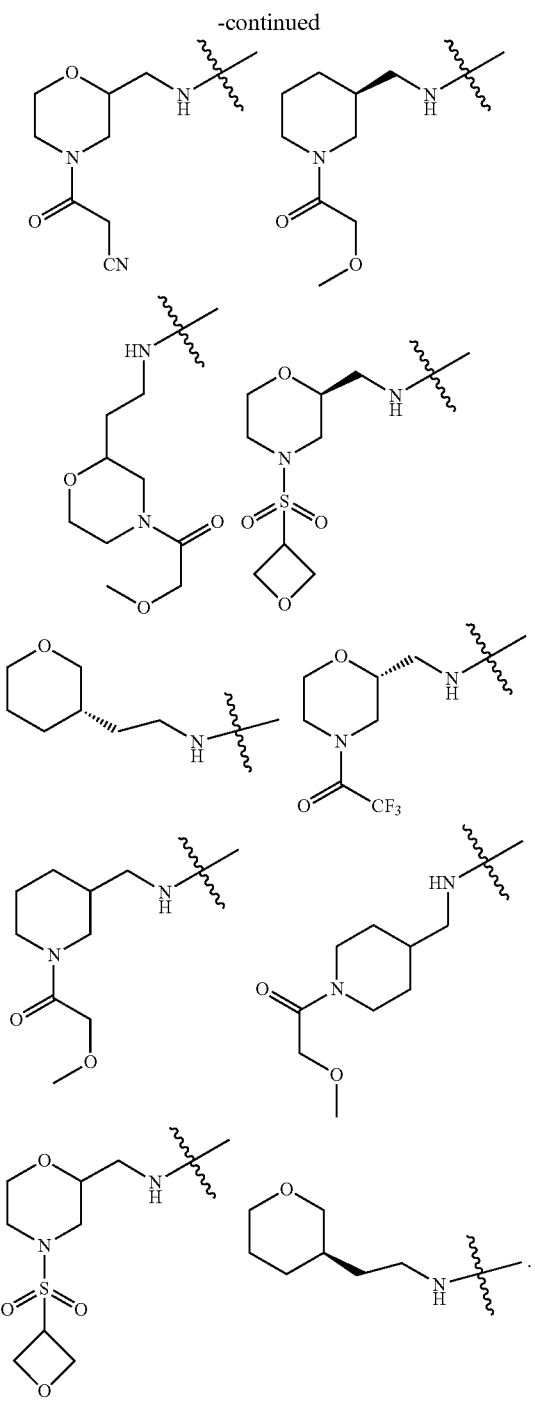

13. The compound, the stereoisomer thereof or the pharmaceutically acceptable salt thereof according to claim 3, wherein $R^1$ is selected from the group consisting of methyl, ethyl, n-propyl, isopropyl or tert-butyl.

14. The compound, the stereoisomer thereof or the pharmaceutically acceptable salt thereof according to claim 6, wherein $R^3$ is selected from 5-6 membered heterocycloalkyl, wherein the 5-6 membered heterocycloalkyl is optionally substituted with one or two groups selected from the group consisting of 3-6 membered heterocycloalkyl, —$COR^a$, —$SO_2R^b$, and $C_{1-6}$ alkyl optionally substituted with halogen.

15. The compound, the stereoisomer thereof or the pharmaceutically acceptable salt thereof according to claim 7, wherein $R^a$ or $R^b$ is each independently selected from the group consisting of H, methyl, ethyl, isopropyl, tert-butyl, cyclopropyl, cyclobutyl and monooxacyclobutyl, wherein the methyl or ethyl is optionally substituted with fluorine, —CN, —$OCH_3$ or —$N(CH_3)_2$.

16. The compound, the stereoisomer thereof or the pharmaceutically acceptable salt thereof according to claim 15, wherein $R^a$ or $R^b$ is each independently selected from the group consisting of H, methyl, ethyl, isopropyl, tert-butyl, trifluoromethyl, pentafluoroethyl, —$CH_2OCH_3$, —$CH_2CN$, —$CH_2N(CH_3)_2$, cyclopropyl, cyclobutyl and monooxacyclobutyl.

17. The compound, the stereoisomer thereof or the pharmaceutically acceptable salt thereof according to claim 8, wherein $R^3$ is selected from the group consisting of tetrahydropyran, piperidine, morpholine and dioxane, wherein the tetrahydropyran, piperidine, morpholine or dioxane is optionally substituted with —$COCH_3$, —$COCH(CH_3)_2$, —$COCH_2OCH_3$, —$SO_2CH_3$, methyl, ethyl or —$CH_2CH_2F$.

18. The compound, the stereoisomer thereof or the pharmaceutically acceptable salt thereof according to claim 9, wherein $R^3$ is selected from the group consisting of

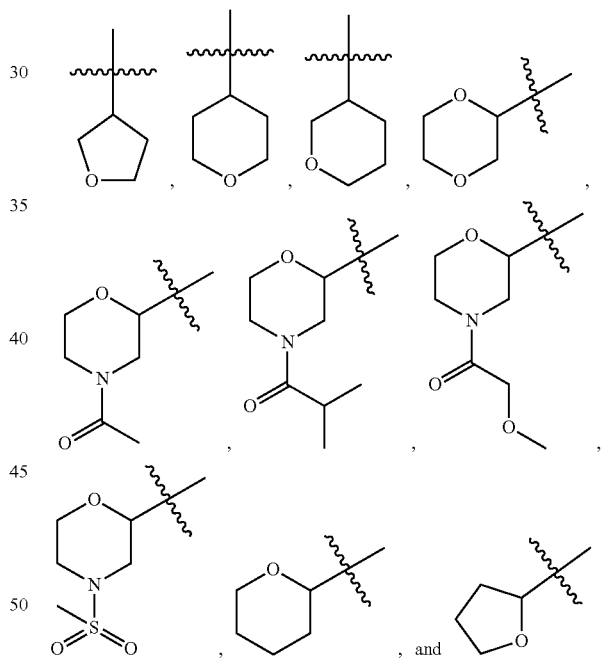

19. A pharmaceutical composition comprising the compound, the stereoisomer thereof or the pharmaceutically acceptable salt thereof according to claim 1, and optionally a pharmaceutically acceptable excipient.

20. A method of ameliorating or eliminating an anti-apoptotic protein BCL-2-related disease, comprising administering to a mammal in need of such treatment a therapeutically effective amount of the compound, the stereoisomer thereof or the pharmaceutically acceptable salt thereof according to claim 1, wherein the anti-apoptotic protein BCL-2-related disease is cancer.

* * * * *

UNITED STATES PATENT AND TRADEMARK OFFICE
CERTIFICATE OF CORRECTION

PATENT NO. : 12,319,689 B2
APPLICATION NO. : 17/613910
DATED : June 3, 2025
INVENTOR(S) : Fei Liu et al.

Page 1 of 5

It is certified that error appears in the above-identified patent and that said Letters Patent is hereby corrected as shown below:

In the Specification

Column 8, Line 30:

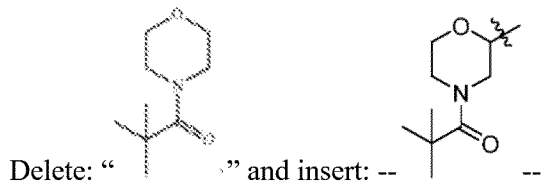

Delete: " " and insert: -- --

Column 9, Line 30:

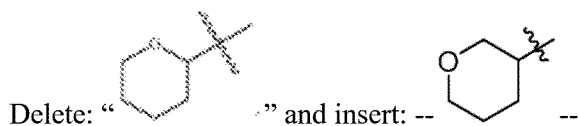

Delete: " " and insert: -- --

Column 37, Line 50:

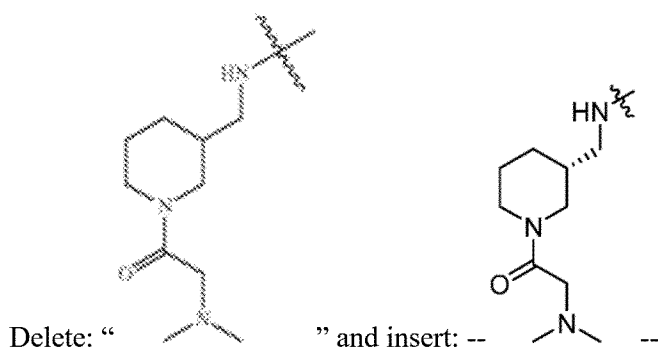

Delete: " " and insert: -- --

Signed and Sealed this
Fourteenth Day of October, 2025

John A. Squires
*Director of the United States Patent and Trademark Office*

Column 44, Line 40:
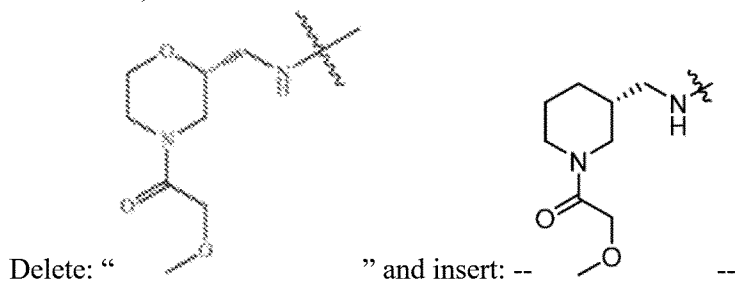
Column 45, Line 5:
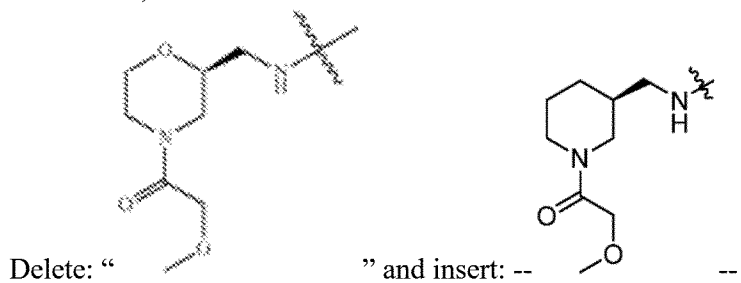
Column 45, Line 40:
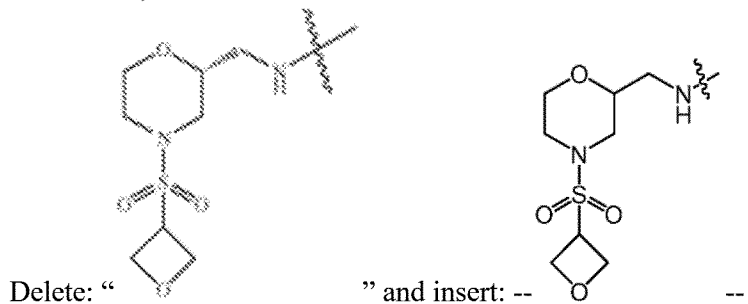
Column 55, Compound 1-i:
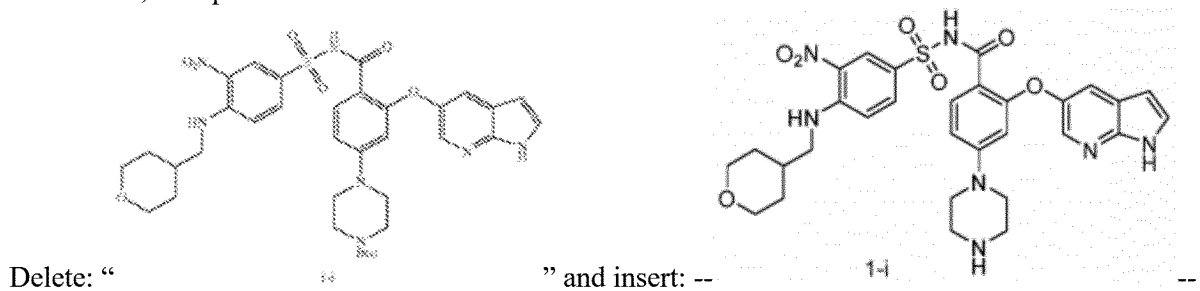
Column 60, Line 65:
Delete: "2-g" and insert: --2-h--

Column 66, Line 65:

Delete: " 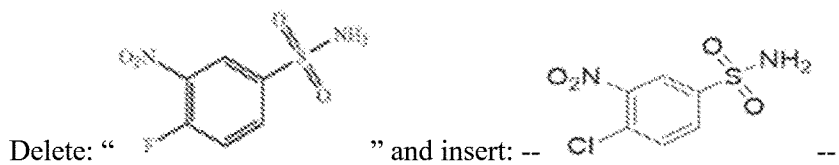 " and insert: -- --

Column 79, Line 30:

Delete: " 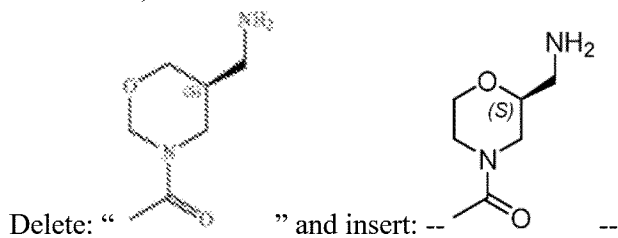 " and insert: -- --

In the Claims

In Claim 1, Column 121, Line 57:
Delete: "—COR$^a$, —SO$_2$R$^b$" and insert: -- -COR$^a$, -SO$_2$R$^b$--

In Claim 1, Column 121, Line 59:
Delete: "R$^a$ or R$^b$" and insert: --R$^a$ or R$^b$--

In Claim 4, Column 122, Line 56:
Delete: "—(CH$_2$)$_n$—R$^3$" and insert: -- -(CH$_2$)$_n$-R$^3$--

In Claim 7, Column 122, Line 60:
Delete: "R$^a$ or R$^b$" and insert: --R$^a$ or R$^b$--

In Claim 11, Column 134, Line 10:

Delete: " 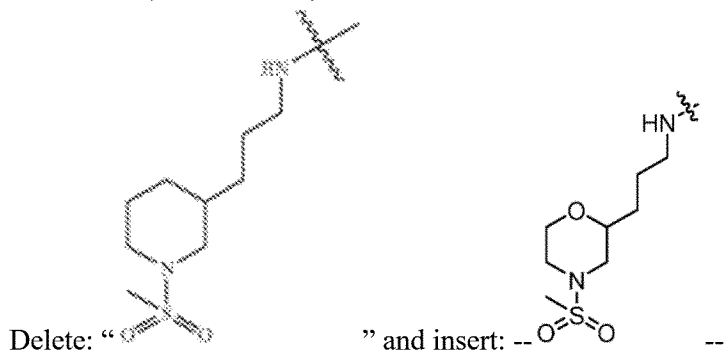 " and insert: -- --

In Claim 11, Column 134, Line 60:
Delete: " 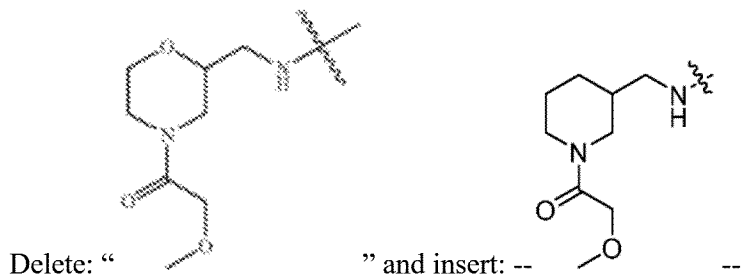 " and insert: -- --
In Claim 12, Column 151, Line 45:
Delete: " 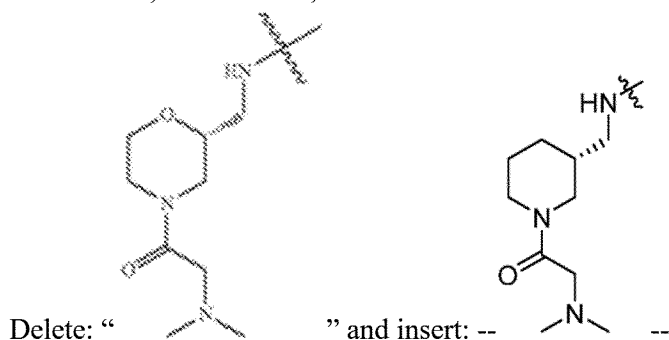 " and insert: -- --
In Claim 12, Column 152, Line 10:
Delete: " 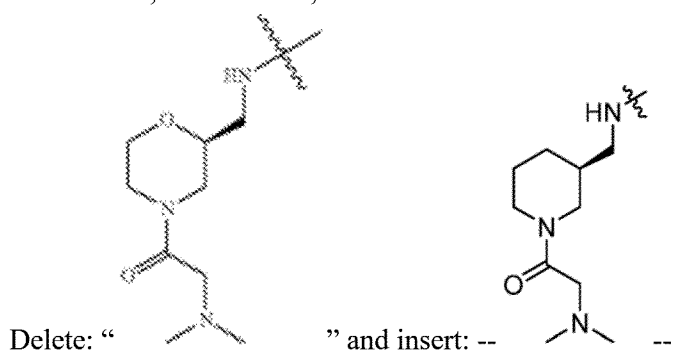 " and insert: -- --
In Claim 12, Column 152, Line 25:
Delete: " 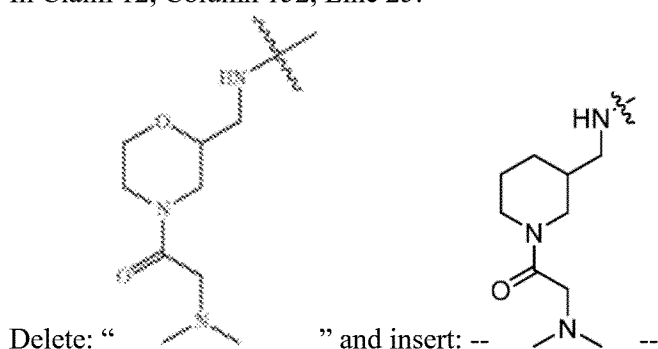 " and insert: -- --
In Claim 13, Column 159, Line 58:
Delete: "n-propyl" and insert: --*n*-propyl--

In Claim 13, Column 159, Line 58:
Delete: "tert-butyl" and insert: --*tert*-butyl--

In Claim 14, Column 159, Lines 64-65:
Delete: "—COR$^a$, —SO$_2$R$^b$" and insert: -- -COR$^a$, -SO$_2$R$^b$--

In Claim 15, Column 160, Line 3:
Delete: "R$^a$ or R$^b$" and insert: --R$^a$ or R$^b$--

In Claim 15, Column 160, Line 4:
Delete: "tert-butyl" and insert: --*tert*-butyl--

In Claim 16, Column 160, Line 10:
Delete: "R$^a$ or R$^b$" and insert: --R$^a$ or R$^b$--

In Claim 16, Column 160, Line 11:
Delete: "tert-butyl" and insert: --*tert*-butyl--